US008617556B2

(12) United States Patent
Beaumont et al.

(10) Patent No.: US 8,617,556 B2
(45) Date of Patent: Dec. 31, 2013

(54) GRAM-POSITIVE BACTERIA SPECIFIC BINDING COMPOUNDS

(75) Inventors: Tim Beaumont, Ouderkerk A/D Amstel (NL); Mark Jeroen Kwakkenbos, Amsterdam (NL); Eric J. Brown, San Francisco, CA (US); John Hiroshi Morisaki, San Francisco, CA (US); Wouter L. W. Hazenbos, San Francisco, CA (US); Sanjeev Mariathasan, Millbrae, CA (US); Kimberly Kajihara, San Francisco, CA (US); Yi Xia, Cupertino, CA (US)

(73) Assignees: Genentech, Inc., South San Francisco, CA (US); AIMM Therapeutics B.V., Amsterdam (NL)

( * ) Notice: Subject to any disclaimer, the term of this patent is extended or adjusted under 35 U.S.C. 154(b) by 0 days.

(21) Appl. No.: 13/305,659

(22) Filed: Nov. 28, 2011

(65) Prior Publication Data

US 2012/0157665 A1 Jun. 21, 2012

Related U.S. Application Data

(62) Division of application No. 12/837,358, filed on Jul. 15, 2010, now abandoned.

(60) Provisional application No. 61/225,878, filed on Jul. 15, 2009.

(30) Foreign Application Priority Data

Jul. 15, 2009 (EP) ..................................... 09165558

(51) Int. Cl.
*A61K 39/40* (2006.01)
(52) U.S. Cl.
USPC .................. 424/165.1; 424/130.1; 424/164.1; 424/178.1; 424/183.1; 530/387.1
(58) Field of Classification Search
None
See application file for complete search history.

(56) References Cited

U.S. PATENT DOCUMENTS

| 6,939,543 B2 | 9/2005 | Fischer et al. |
| 2011/0020323 A1 | 1/2011 | Beaumont et al. |

FOREIGN PATENT DOCUMENTS

| CN | 101460519 A | 6/2009 |
| WO | WO-96/23896 A1 | 8/1996 |
| WO | WO-2006/034488 A2 | 3/2006 |
| WO | WO-2007/141274 A2 | 12/2007 |
| WO | WO-2007/141274 A3 | 12/2007 |
| WO | WO-2008/121616 A2 | 10/2008 |
| WO | WO-2008/121616 A3 | 10/2008 |
| WO | WO-2008/141044 A2 | 11/2008 |
| WO | WO-2008/141044 A3 | 11/2008 |
| WO | WO-2009/012256 A1 | 1/2009 |
| WO | WO-2009/012268 A1 | 1/2009 |
| WO | WO-2009/052249 A1 | 4/2009 |
| WO | WO-2009/099728 A1 | 8/2009 |

OTHER PUBLICATIONS

Rudikoff et al (Proc Natl Acad Sci USA 1982 vol. 79 p. 1979).*
MacCallum et al. J. Mol. Biol. (1996) 262,732-745.*
De Pascalis et al. The Journal of Immunology (2002) 169, 3076-3084.*
Casset et al. (2003) BBRC 307, 198-205.*
Vajdos et al. (2002) 320, 415-428.*
Holm et al. (2007) 44, 1075-1084.*
Chen et al. J. Mol. Bio. (1999) 293, 865-881.*
Wu et al. J. Mol. Biol. (1999) 294, 151-162.*
Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Greenspan et al (Nature Biotechnology 7: 936-937, 1999).*
Chothia et al (The EMBO Journal, 1986, 5/4:823-26).*
Davies, J. et al. (Sep. 1, 1996). "Affinity Improvement of Single AntibodyVH Domains: Residues in all Three Hypervariable Regions Affect Antigen Binding," *Immunotechnology* 2(3):169-179.
Diehl, S.A. et al. (2008). "STAT3-Mediated Up-Regulation of BLIMP1 is Coordinated With BCL6 Down-Regulation to Control Human Plasma Cell Differentiation," *J Immunol* 180:4805-4815.
Elliott, T. et al. (Dec. 14, 2002). "Antibody Response to Staphylococcal Slime and Lipoteichoic Acid," *The Lancet* 360(9349):1977.
Gaudreau, M-C. et al. (Dec. 8, 2006, e-pub. Sep. 22, 2006). "Protective Immune Responses to a Multi-Gene DNA Vaccine Against *Staphylococcus aureus*," *Vaccine* 25:814-824.
Greenberg, J.W. et al. (Aug. 1996). "Influence of Lipoteichoic Acid Structure on Recognition by the Macrophage Scavenger Receptor," *Infection and Immunity* 64(8):3318-3325.
Hammonds, S.J. et al. (Jul. 15, 1991, e-pub. Mar. 27, 2006). "Differentiation of Enterococci From Other Group D Streptococci by Means of a Specific Monoclonal Antibody," *FEMS Microbiology Letters* 82(1):91-94.
Hetherington, S. et al. (Oct. 2006). "Phase I Dose Escalation Study to Evaluate the Safety and Pharmacokinetic Profile of Tefibazumab in Subjects with End-Stage Renal Disease Requiring Hemodialysis," *Antimicrobial Agents and Chemotherapy* 50(10):3499-3500.
Holt, L.J. et al. (Nov. 1, 2003). "Domain Antibodies: Proteins for Therapy," *TRENDS in Biotechnology* 21(11):484-490.
International Search Report mailed on Apr. 1, 2011, for PCT Application No. PCT/NL2010/050456, filed on Jul. 15, 2010, ten pages.
Jaleco, A.C. et al. (Oct. 15, 1999). "Genetic Modification of Human B-Cell Development: B Cell Development is Inhibited by the Dominant Negative Helix Loop Helix Factor Id3," *Blood* 94(8):2637-2646.
John, J.F., Jr. (Oct. 1, 2006). "Drug Evaluation:Tefibazumab-A Monoclonal Antibody Against Staphylococcal Infection," *Current Opinion in Molecular Therapeutics* 8(5):455-460.

(Continued)

*Primary Examiner* — Jennifer Graser
(74) *Attorney, Agent, or Firm* — Morrison & Foerster LLP

(57) ABSTRACT

The present invention provides improved binding compounds capable of specifically binding Gram-positive bacteria. Binding compounds are provided that are fully human, enabling therapeutic applications in human individuals.

74 Claims, 32 Drawing Sheets

(56) References Cited

OTHER PUBLICATIONS

Kabat, E.A. et al. (1991). *Sequences of Proteins of Immunological Interest*, 5$^{th}$ Ed. Public Health Service National Institute of Health, Bethesda, MD, p. xiii-xcvi.

Keller, R. et al. (Sep. 1992). "Macrophage Response to Bacteria: Induction of Marked Secretory and Cellular Activities by Lipoteichoic Acids," *Infect. Immun.* 60(9):3664-3672.

Kwakkenbos, M.J. et al. (Jan. 2010, e-pub. Dec. 20, 2009). "Generation of Stable Monoclonal Antibody-Producing B Cell Receptor-Positive Human Memory B Cells by Genetic Programming," *Nat. Med.* 16(1):123-128.

McCrea, K.W. et al. (Jul. 1, 2000). "The Serine-Aspartate Repeat (Sdr) Protein Family in *Staphylococcus epidermidis*," *Microbiology* 146:1535-1546.

Moran, G.J. et al. (Aug. 17, 2006). "Methicillin-Resistant *S. aureus* Infections Among Patients in the Emergency Department," *NEMJ* 355(7):666-674.

Polotsky, V.Y. et al. (Jan. 1996). "Interaction of Human Mannose-Binding Protein with Lipoteichoic Acids," *Infection and Immunity* 64(1):380-383.

Reilley, S. et al. (Mar. 2005). "Open-Label, Dose Escalation Study of the Safety and Pharmacokinetic Profile of Tefibazumab in Healthy Volunteers," *Antimicrobial Agents and Chemotherapy* 49(3):959-962.

Scheeren, F.A. et al. (Mar. 2005, e-pub. Feb. 13, 2005). "STAT5 Regulates the Self-Renewal Capacity and Differentiation of Human Memory B Cells and Controls Bcl-6 Expression," *Nat. Immunol.* 6(3):303-313.

Schaffer, A. et al. (Apr. 2006). "Immunization with *Staphylococcus aureus* Clumping Factor 8, A Major Determinant in Nasal Carriage, Reduces Nasal Colonization in a Murine Model," *Infection and Immunity* 74(4):2145-2153.

Shvarts, A. et al. (2002). "A Senescence Rescue Screen Identifies BCL6 as an Inhibitor of Anti-Proliferative p19$^{ARF}$-p53 Signaling," *Genes Dev.* 16:681-686.

Tuchscherr, L.P.N. et al. (Dec. 2008, e-pub. Sep. 22, 2008). "Antibodies to Capsular Polysaccharide and Clumping Factor A Prevent Mastitis and the Emergence of Unencapsulated and Small-Colony Variants of *Staphyloccus aureus* in Mice," *Infection and Immunity* 76(12):5738-5744.

Yin, R-L. et al. (Dec. 15, 2009). "Construction and Immunogenicity of a DNA Vaccine Containing Clumping Factor A of *Staphylococcus aureus* and Bovine IL18," *Veterinary Immunology and Immunopathology* 132:270-274.

Weidenmaier, C. et al. (Apr. 2008, e-pub. Mar. 10, 2008). "Teichoic Acids and Related Cell-Wall Glycopolymers in Gram-Positive Physiology and Host Interactions," *Nat Rev. Microbiol.* 6(4):276-287.

Wergeland, H.I. et al. (Jun. 1, 1989). "Antibodies to Staphylococcal Peptidoglycan and its Peptide Epitopes, Teichoic Acid, and Lipotechoic Acid in Sera From Blood Donors and Patients with Staphylococcal Infections," *Journal of Clinical Microbiology* 27(6):1286-1291.

\* cited by examiner

Figure 1 aMRSA F1 clone

NB: CDR numbering according to Kabat et al (1991)

Heavy chain

Recombined from gene segments:
IGHV3-23*01
IGHD6-19*01
IGHJ4*02

AMINO ACID:
Fw1 EVQLLESGGGLVQPGGSLRLSCAASGFTLS
CDR1 RFAMS
Fw2 WVRQAPGRGLEWVA
CDR2 SINNGNNPYYARSVQY
Fw3 RFTVSRDVSQNTVSLQMNNLRAEDSATYFCAK
CDR3 DHPSSGWPTFDS
Fw4 WGPGTLVTVSS

NUCLEOTIDE:
Fw1 gag gtg caa ctg ttg gag tcg ggg ggg ggc ttg gtg cag ccg ggg ggg tcc ctg aga ctc tcc tgt gca gcc tct gga ttc acc ctt agc CDR1 cgc ttt gcc atg agc Fw2 tgg gtc cgc cag gct cca gga agg gga ctg gaa tgg gtc gca CDR2 tcg atc aat aat ggg aat aac cca tac tac gca cgg tcg gta caa tac

Figure 1 (Continued)

Fw3 cgc ttc acc gtc tcc agg gac gtc tcc cag aac acg gtg tct ctg cag atg aac aac ctg aga gcc gaa gac tcg gcc aca tat ttc tgt gct aaa CDR3 gat cac cct agt agt ggc tgg ccc acc ttt gac tcc Fw4 tgg ggc ccg gga acc ctg gtc acc gtc tcc tcg

Light chain

Recombined from gene segments:
IGKV1-5*03
IGKJ2*01

AMINO ACID:
Fw1 DIQLTQSPSALPASVGDRVSITC
CDR1 RASENVGDWLA
Fw2 WYRQKPGKAPNLLIY
CDR2 KTSILES
Fw3 GVPSRFSGSGSGTEFTLTISSLQPDDFATYYC
CDR3 QHYIRFPYT
Fw4 FGQGTKLEIKRTV

NUCLEOTIDE:
Fw1 gac atc cag ttg acc cag tct cct tcc gcc ctg cct gca tct gtg gga gac aga gtc agc atc act tgt CDR1 cgg gcc agt gaa aac gtt ggt gac tgg ttg gcc Fw2 tgg tat cgg cag aaa ccg ggg aaa gcc cct aat ctt ctc atc tat CDR2 aag aca tct att cta gaa agt

Figure 1 (Continued)

Fw3 ggg gtc cca tca agg ttc agc ggc agt ggg tct ggg aca gaa ttc act ctc acc atc agc agc ctg cag cct gat gat ttt gca act tat tac tgt CDR3 caa cac tat ata cgt ttc ccg tac act Fw4 ttt ggc cag ggg acc aag ctg gag atc aaa cga act gtg Figure 4A1
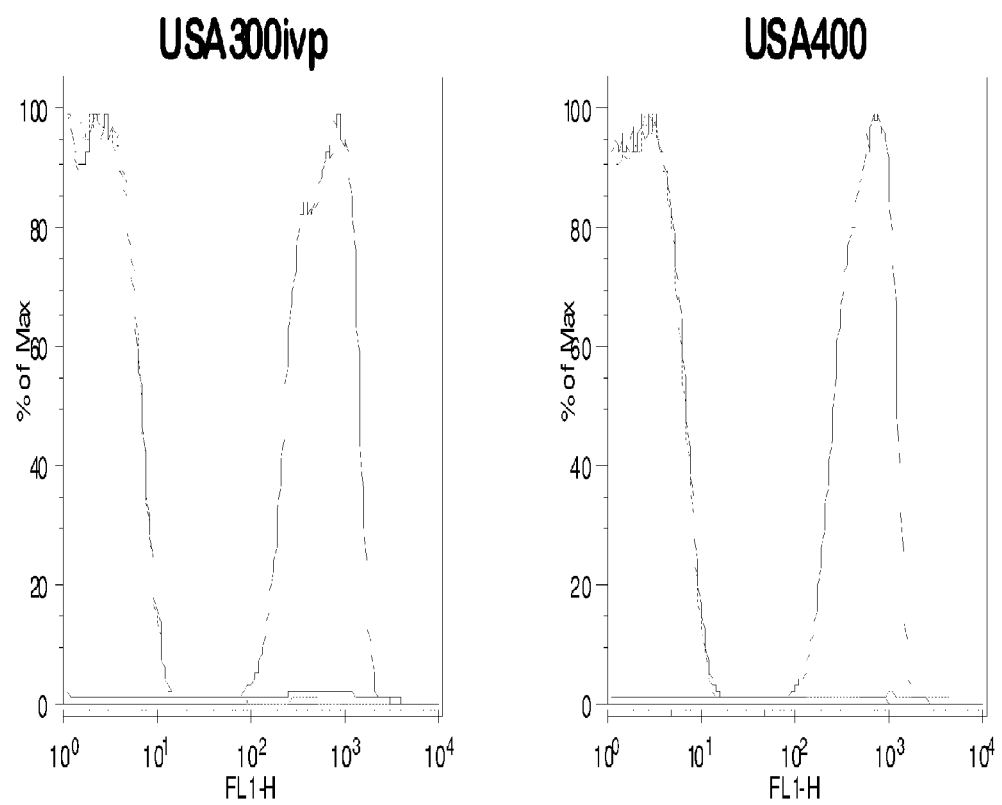

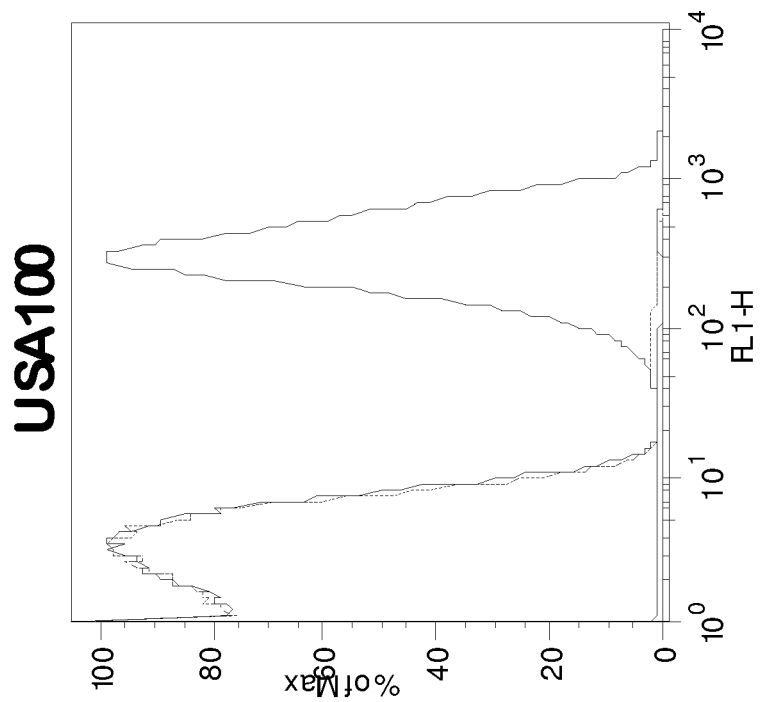
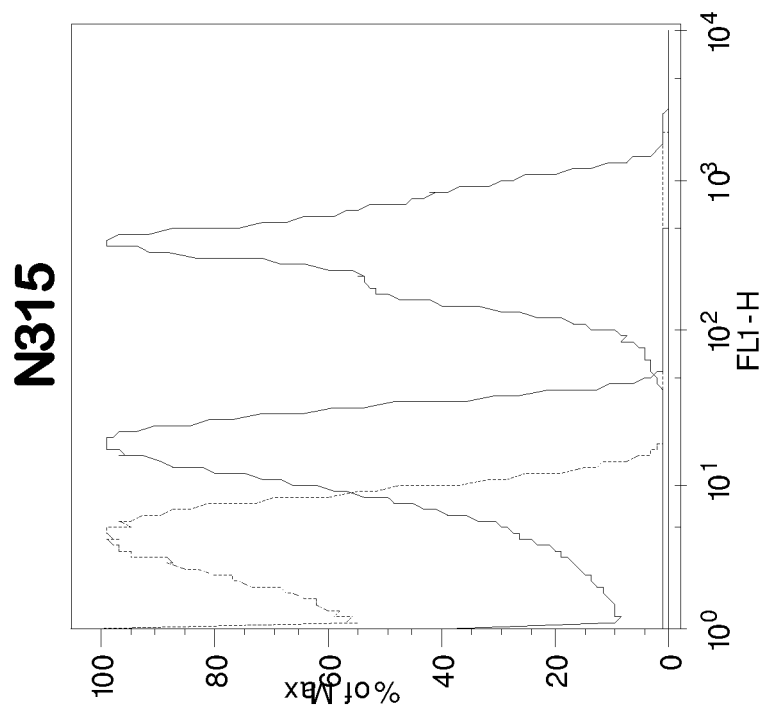
Figure 4A2

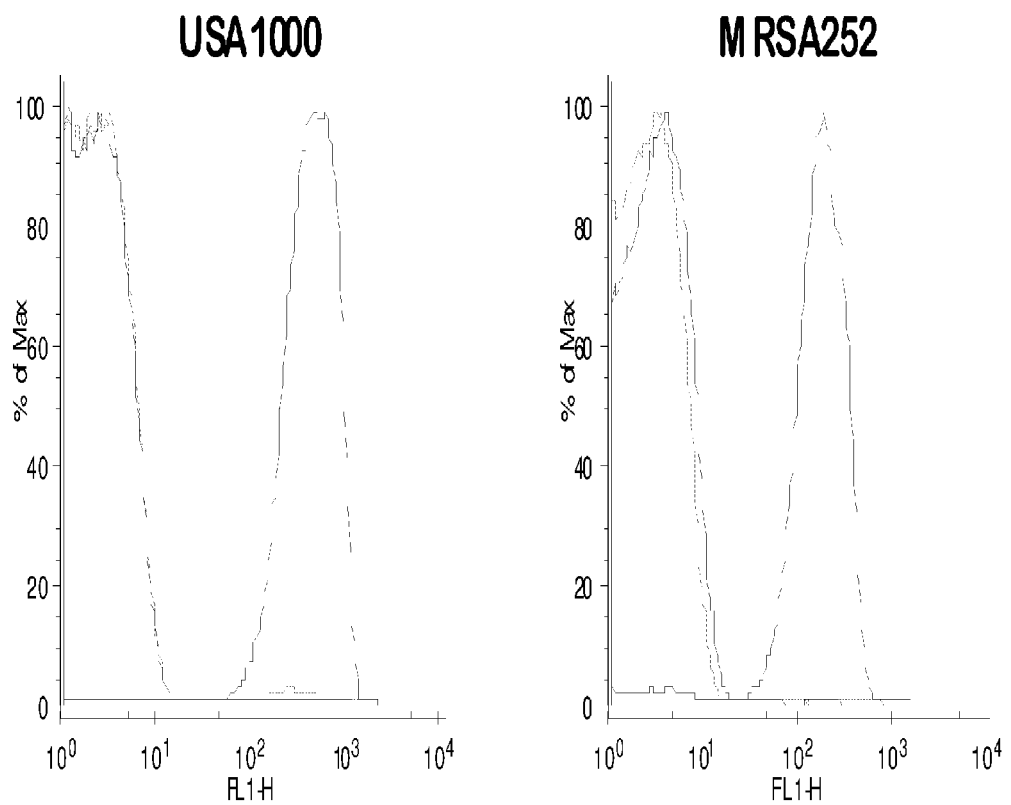
Figure 4A3

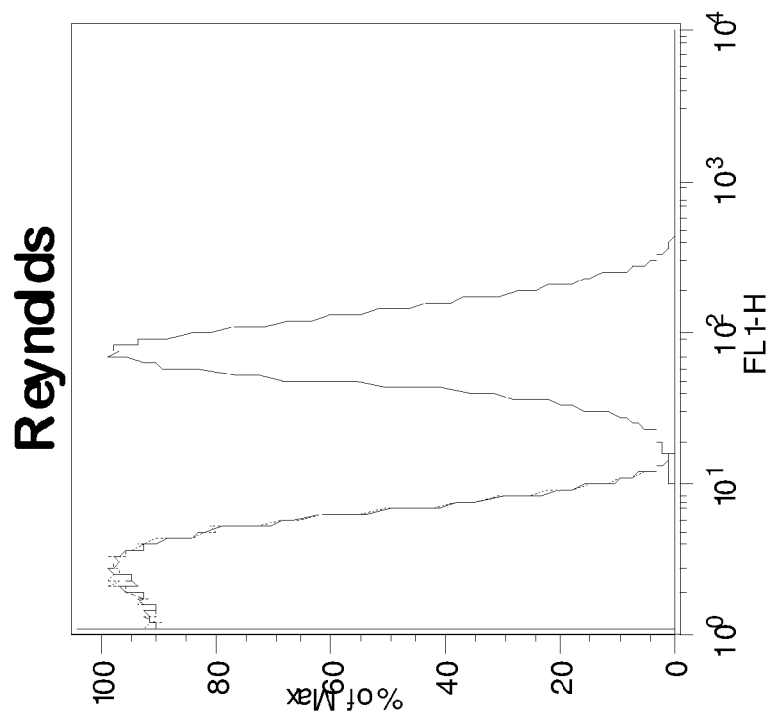
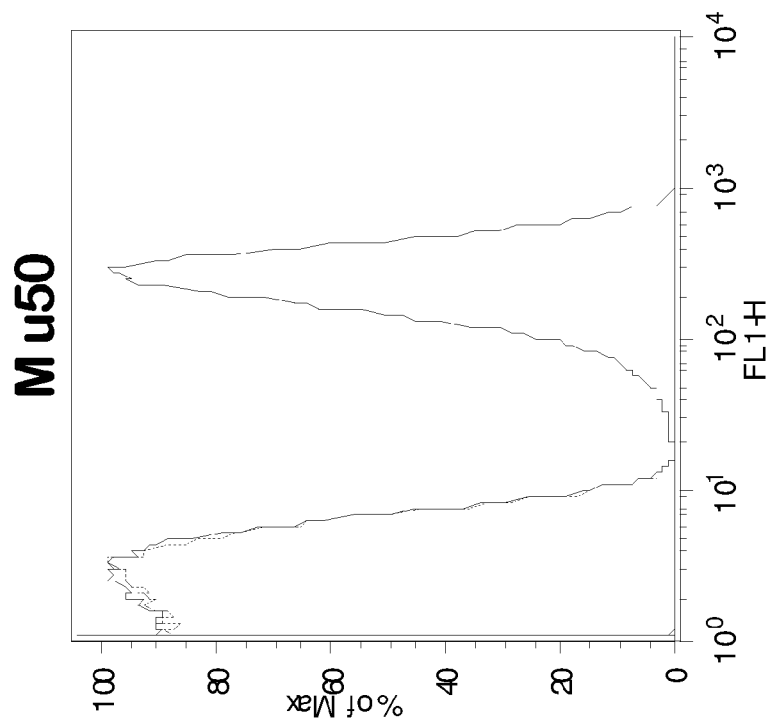
Figure 4A4

Figure 4A5
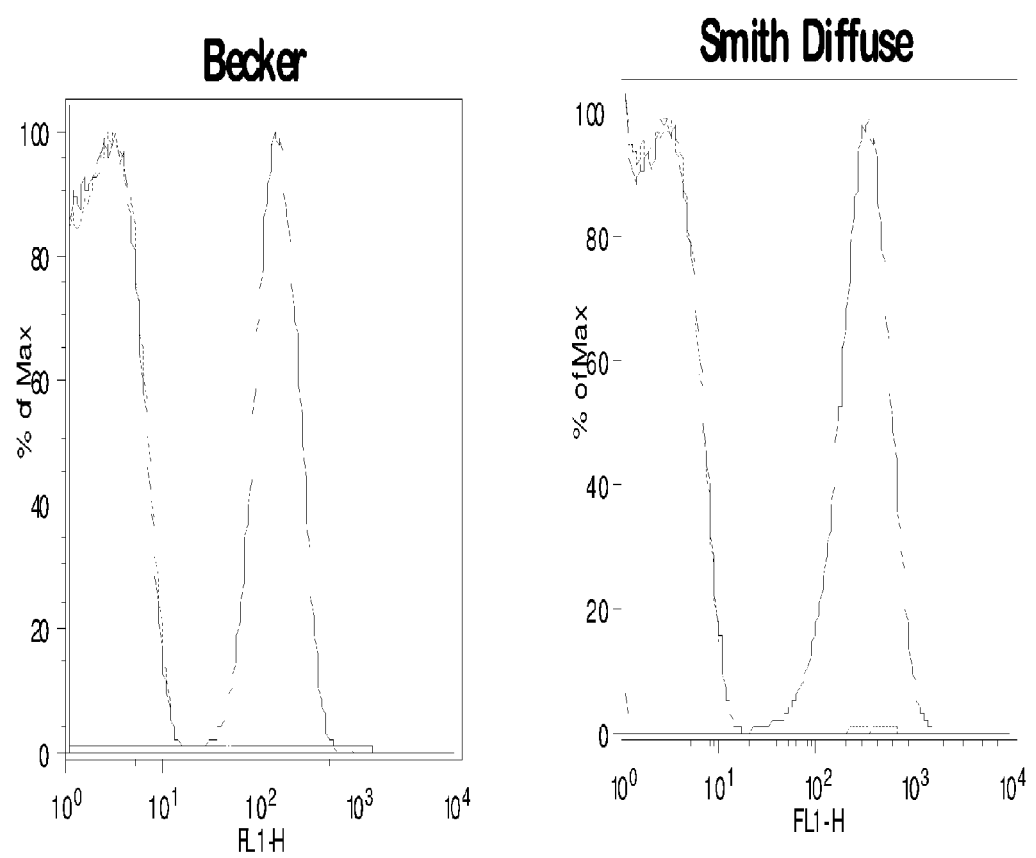

Figure 4A6
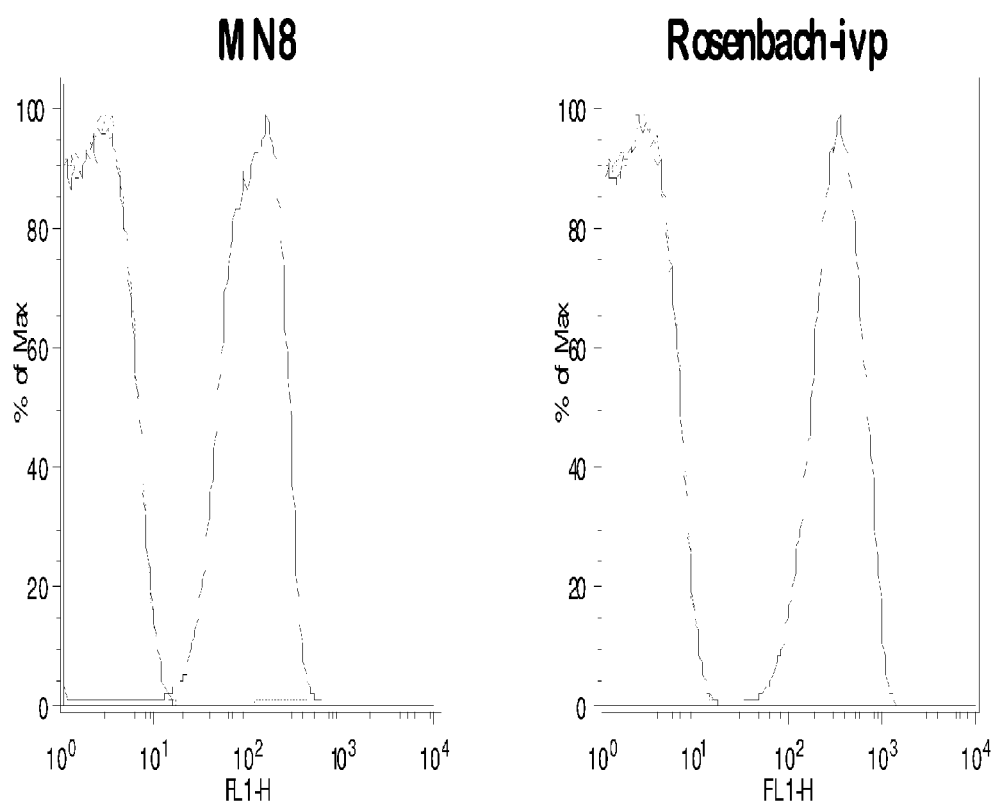

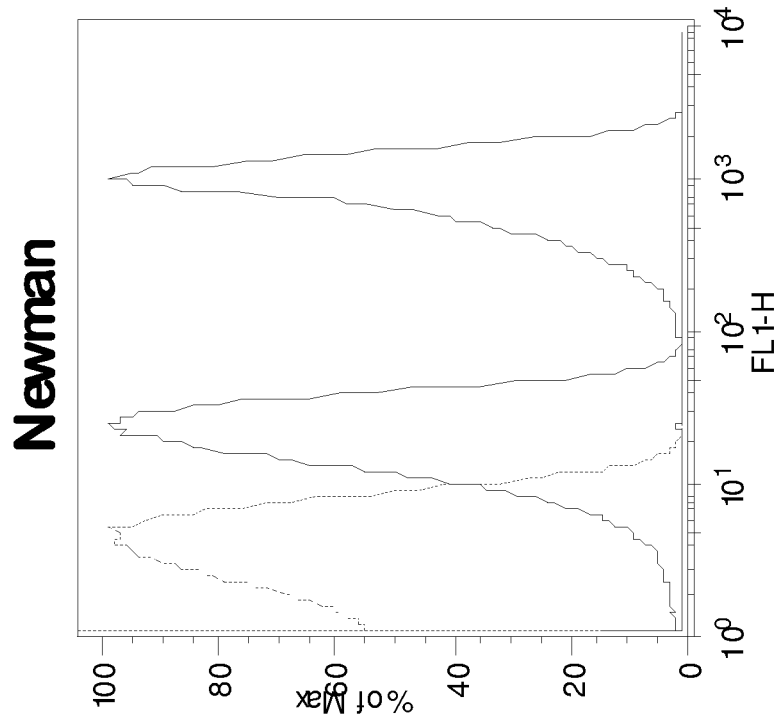
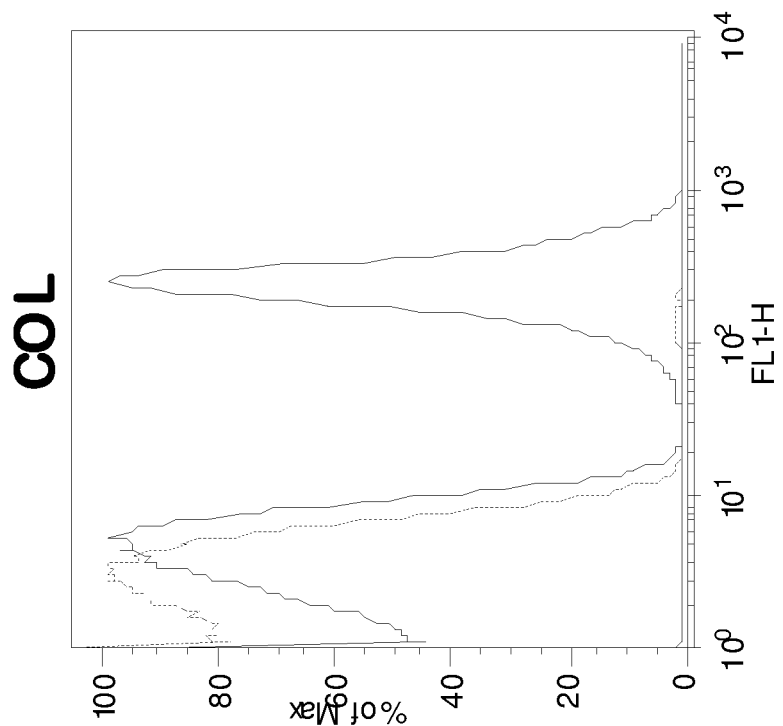
Figure 4A7

Figure 4B1
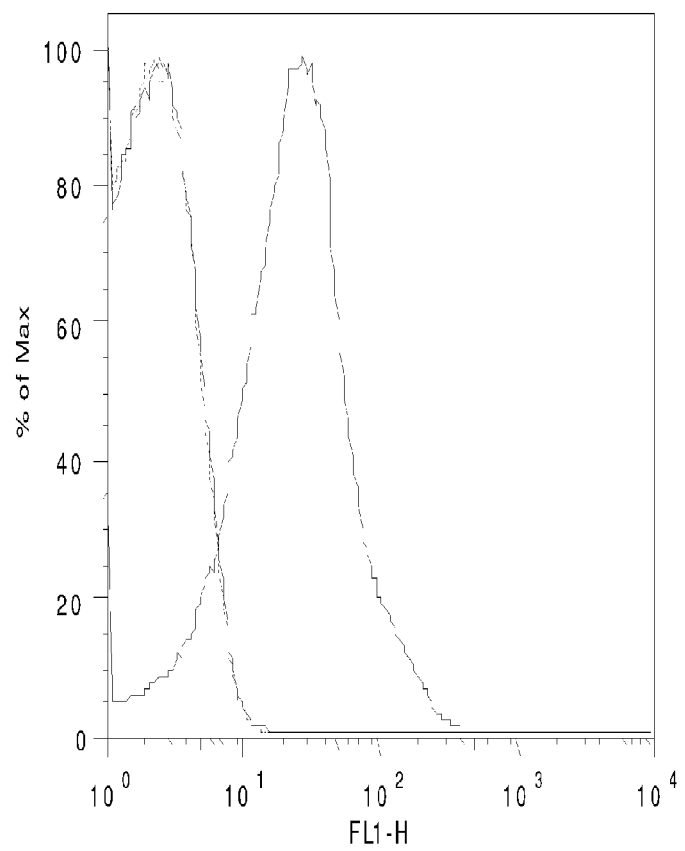

Figure 4B2
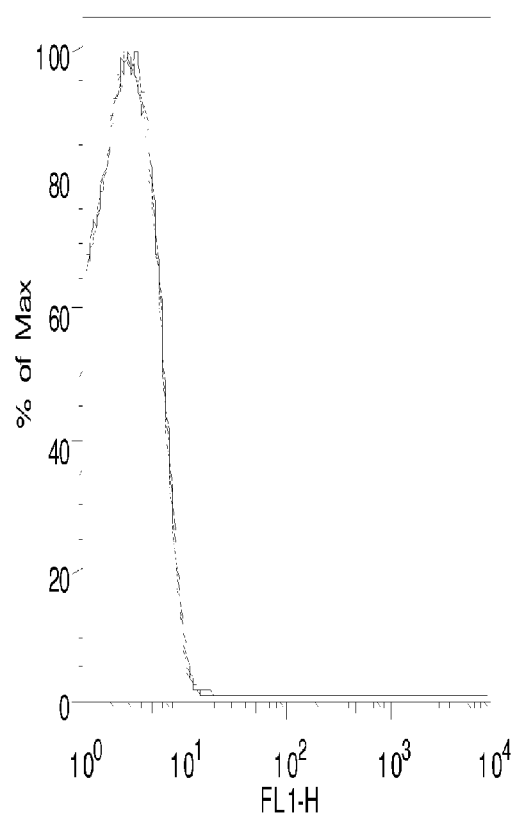
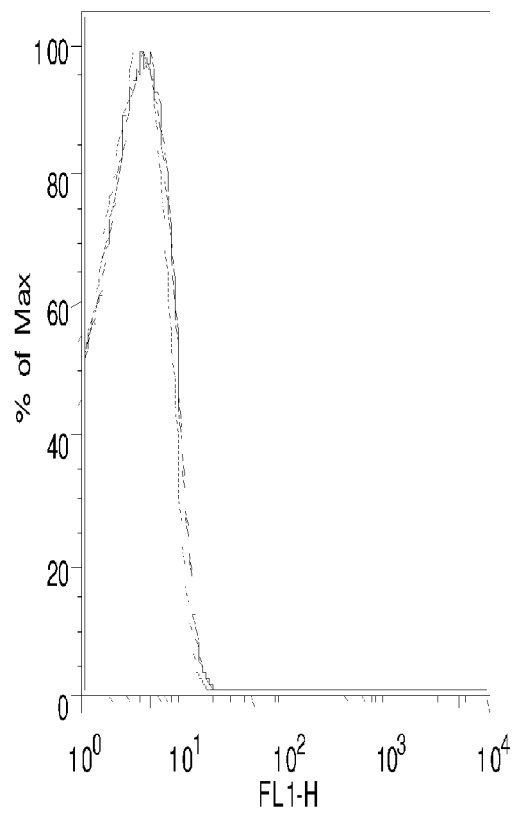

Figure 4B3
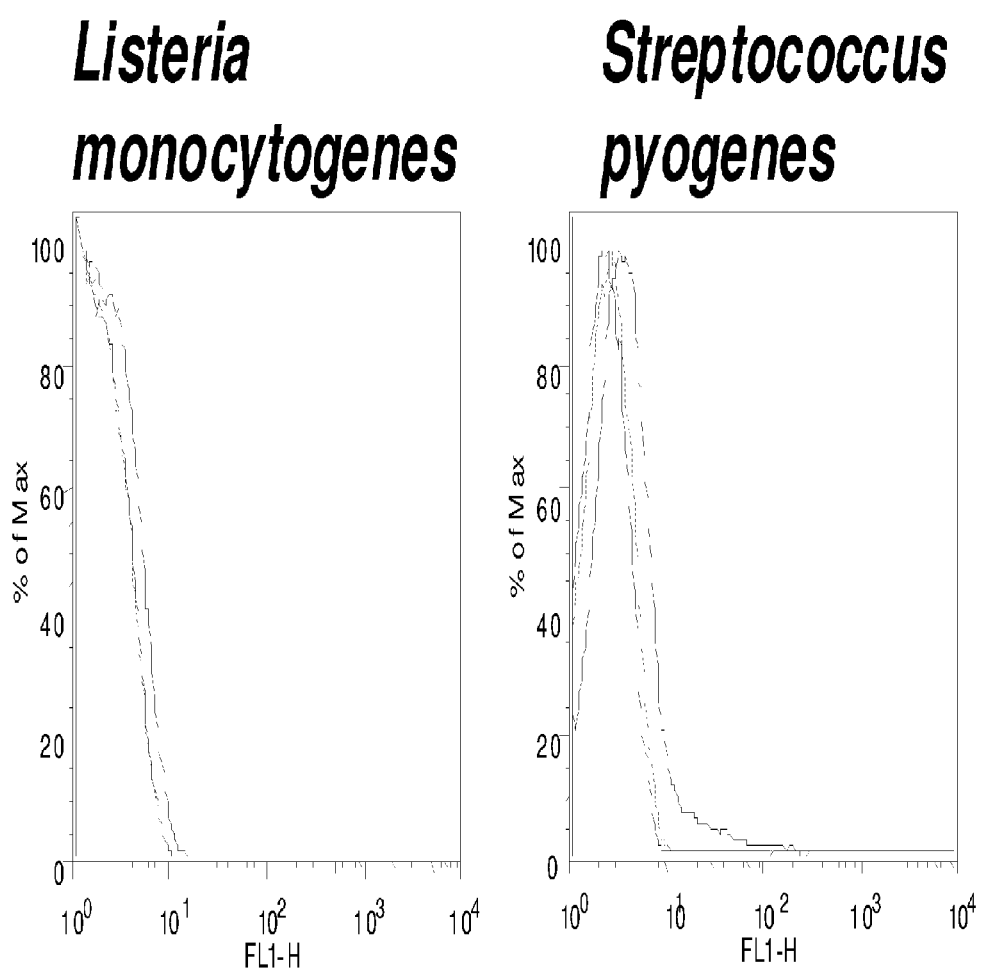

A

Figure 5A1
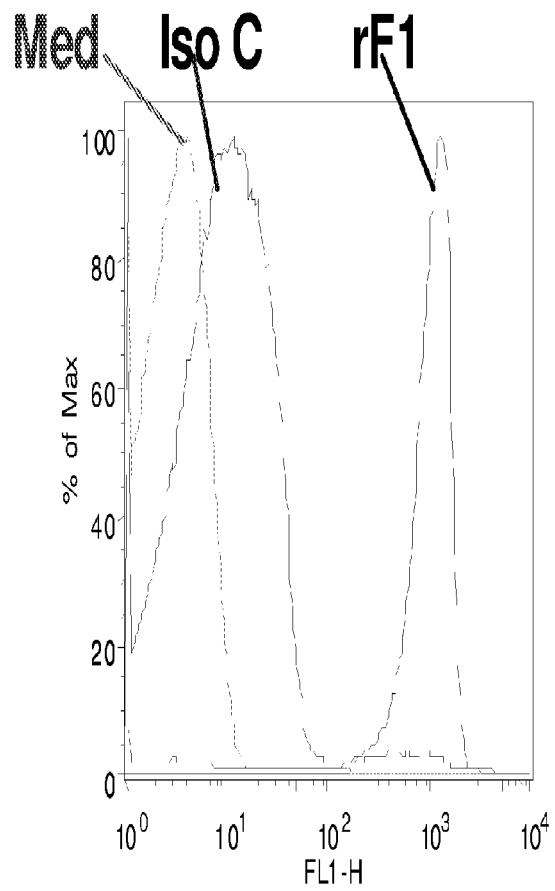

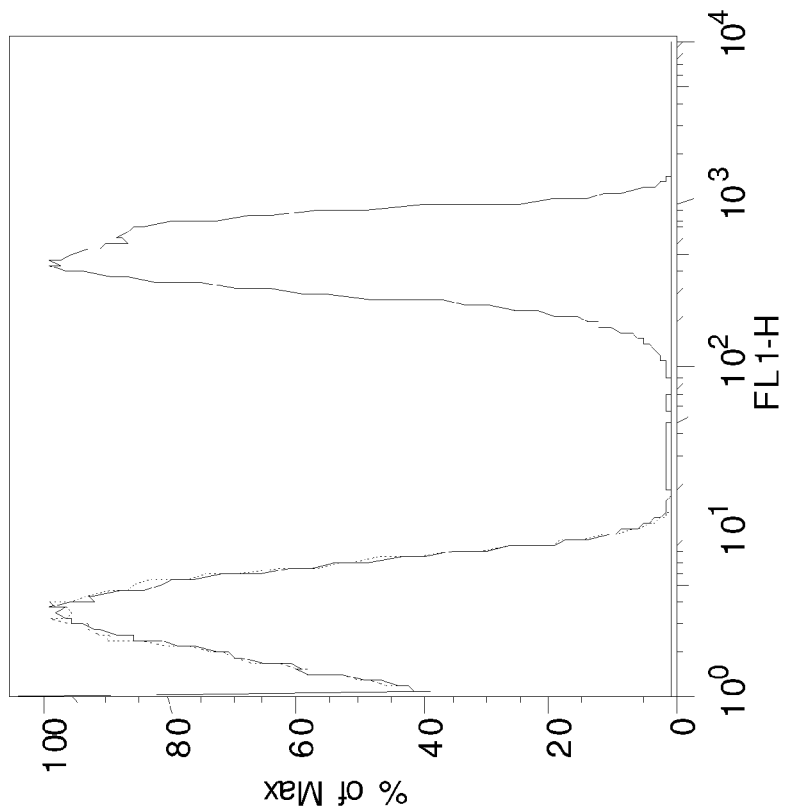
Figure 5A2

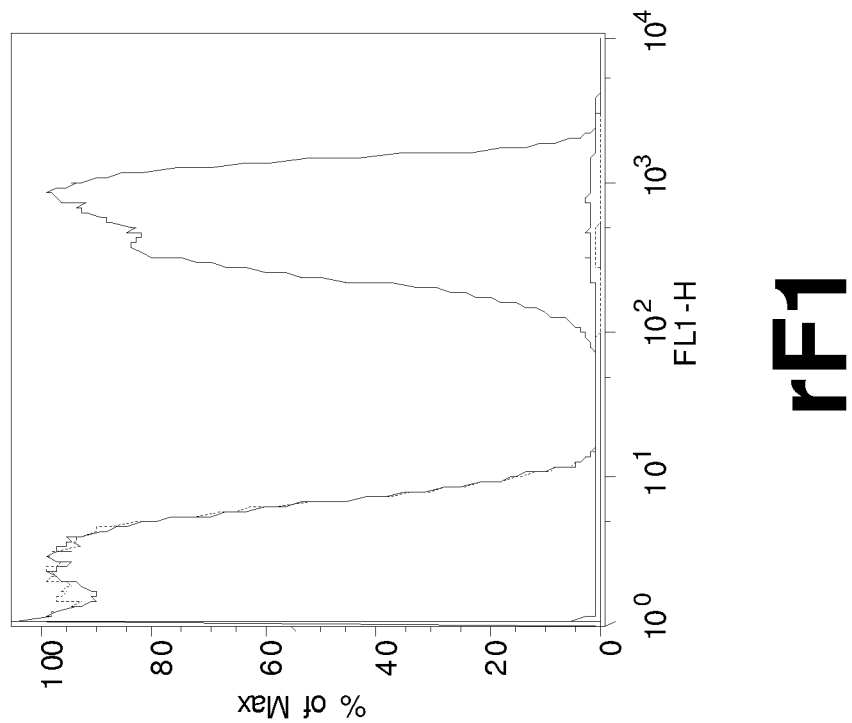
Figure 5A3

Figure 9A

|  | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 |
|---|---|---|---|---|---|---|---|---|---|---|---|---|---|---|---|---|---|---|---|---|---|---|---|---|---|---|---|---|---|---|---|---|---|---|
| rF1 heavy chain | E | V | Q | L | V | E | S | G | G | G | L | V | Q | P | G | G | S | L | R | L | S | C | A | A | S | G | F | T | L | S | R | F | A | M |
| rF1 A114C       | E | V | Q | L | V | E | S | G | G | G | L | V | Q | P | G | G | S | L | R | L | S | C | A | A | S | G | F | T | L | S | R | F | A | M |

|  | 35 | B | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 |
|---|----|---|----|----|----|----|----|----|----|----|----|----|----|----|----|----|----|----|----|----|----|----|----|----|----|----|----|----|----|----|
| rF1 heavy chain | S |   | W | V | R | Q | A | P | G | R | G | L | E | W | V | A | S | I | N | N | G | N | N | P | Y | Y | A | R | S | V |
| rF1 A114C       | S |   | W | V | R | Q | A | P | G | R | G | L | E | W | V | A | S | I | N | S | G | N | N | P | Y | Y | A | R | S | V |

|  | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 |
|---|----|----|----|----|----|----|----|----|----|----|----|----|----|----|----|----|----|----|----|----|----|----|----|----|----|----|----|----|----|----|----|
| rF1 heavy chain | Q | Y | R | F | T | V | S | R | D | D | S | Q | N | T | V | S | L | Q | M | R | A | E | D | S | A | T | Y | F | C | A | K |
| rF1 A114C       | Q | Y | R | F | T | V | S | R | D | D | S | Q | N | T | V | S | L | Q | M | R | A | E | D | S | A | T | Y | F | C | A | K |

|  | 95 | 96 | 97 | 98 | 99 | 100 | 101 | 102 | C | D | E | F | G | H | I | J | 103 | 104 | 105 | 106 | 107 | 108 | 109 | 110 | 111 | 112 | 113 |
|---|----|----|----|----|----|-----|-----|-----|---|---|---|---|---|---|---|---|-----|-----|-----|-----|-----|-----|-----|-----|-----|-----|-----|
| rF1 heavy chain | D | H | P | S | S | G | F | D | B | C | A | E | G | H | I | J | W | G | P | G | T | L | V | T | V | S | S |
| rF1 A114C       | D | H | P | S | S | G | F | D | B | C | A | E | G | H | I | J | W | G | P | G | T | L | V | T | V | S | S |

|  | 114 | 115 | 116 | 117 | 118 | 119 | 120 | 121 | 122 | 123 | 124 | 125 | 126 | 127 | 128 | 129 | 130 | 131 | 132 | 133 | 134 | 135 | 136 | 137 | 138 | 139 | 140 | 141 | 142 | 143 | 144 | 145 | 146 | 147 |
|---|-----|-----|-----|-----|-----|-----|-----|-----|-----|-----|-----|-----|-----|-----|-----|-----|-----|-----|-----|-----|-----|-----|-----|-----|-----|-----|-----|-----|-----|-----|-----|-----|-----|-----|
| rF1 heavy chain | A | S | T | K | G | P | S | V | F | P | L | A | P | S | S | K | S | . | . | T | S | G | G | T | A | A | L | G | C | L | V | K | D | Y |
| rF1 A114C       | C | S | T | K | G | P | S | V | F | P | L | A | P | S | S | K | S | . | . | T | S | G | G | T | A | A | L | G | C | L | V | K | D | Y |

|  | 148 | 149 | 150 | 151 | 152 | 153 | 154 | 155 | 156 | 157 | 158 | 159 | 160 | 161 | 162 | 163 | 164 | 165 | 166 | 167 | 168 | 169 | 170 | 171 | 172 | 173 | 174 | 175 | 176 | 177 | 178 | 179 | 180 | 181 |
|---|-----|-----|-----|-----|-----|-----|-----|-----|-----|-----|-----|-----|-----|-----|-----|-----|-----|-----|-----|-----|-----|-----|-----|-----|-----|-----|-----|-----|-----|-----|-----|-----|-----|-----|
| rF1 heavy chain | F | P | E | P | V | T | V | S | S | W | . | V | N | S | S | G | A | L | T | S | G | V | H | T | F | P | A | V | L | Q | S | S |   |   |
| rF1 A114C       | F | P | E | P | V | T | V | S | S | W | . | V | N | S | S | G | A | L | T | S | G | V | H | T | F | P | A | V | L | Q | S | S |   |   |

|  | 182 | 183 | 184 | 185 | 186 | 187 | 188 | 189 | 190 | 191 | 192 | 193 | 194 | 195 | 196 | 197 | 198 | 199 | 200 | 201 | 202 | 203 | 204 | 205 | 206 | 207 | 208 | 209 | 210 | 211 | 212 | 213 | 214 | 215 |
|---|-----|-----|-----|-----|-----|-----|-----|-----|-----|-----|-----|-----|-----|-----|-----|-----|-----|-----|-----|-----|-----|-----|-----|-----|-----|-----|-----|-----|-----|-----|-----|-----|-----|-----|
| rF1 heavy chain | S | G | L | Y | S | L | S | S | V | V | T | V | P | S | S | S | L | G | T | T | . | . | . | T | Y | I | C | N | V | N | H | K | P | S |
| rF1 A114C       | S | G | L | Y | S | L | S | S | V | V | T | V | P | S | S | S | L | G | T | T | . | . | . | T | Y | I | C | N | V | N | H | K | P | S |

|  | 216 | 217 | 218 | 219 | 220 | 221 | 222 | 223 | 224 | 225 | 226 | 227 | 228 | 229 | 230 | 231 | 232 | 233 | 234 | 235 | 236 | 237 | 238 | 239 | 240 |
|---|-----|-----|-----|-----|-----|-----|-----|-----|-----|-----|-----|-----|-----|-----|-----|-----|-----|-----|-----|-----|-----|-----|-----|-----|-----|
| rF1 heavy chain | N | T | K | V | . | D | R | . | . | V | E | P | K | S | C | D | . | . | . | K | T | H | T | C | P |
| rF1 A114C       | N | T | K | V | . | D | K | . | . | V | E | P | K | S | C | D | . | . | . | K | T | H | T | C | P |

Figure 9B

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|---|---|---|---|---|---|---|---|---|---|---|---|---|---|---|---|---|
| rF1 light chain | D | I | Q | L | T | Q | S | P | S | A | L | P | A | S | V | G | D | R | V | S | I | T | C | R | A | S | E | N | V | G | D | W |
| rF1 V205C | D | I | Q | L | T | Q | S | P | S | A | L | P | A | S | V | G | D | R | V | S | I | T | C | R | A | S | E | N | V | G | D | W |

| | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 |
|---|---|---|---|---|---|---|---|---|---|---|---|---|---|---|---|---|---|---|---|---|---|---|---|---|---|---|---|---|---|---|---|---|---|---|---|---|---|---|
| rF1 light chain | L | A | W | Y | R | Q | K | P | G | K | A | P | N | L | L | I | Y | K | T | S | I | L | E | S | G | V | P | S | R | F | S | G | S | G | S | G | T | E |
| rF1 V205C | L | A | W | Y | R | Q | K | P | G | K | A | P | N | L | L | I | Y | K | T | S | I | L | E | S | G | V | P | S | R | F | S | G | S | G | S | G | T | E |

| | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 |
|---|---|---|---|---|---|---|---|---|---|---|---|---|---|---|---|---|---|---|---|---|---|---|---|---|---|---|---|---|---|---|---|---|
| rF1 light chain | F | T | L | T | I | S | S | L | Q | P | D | D | F | A | T | Y | Y | C | Q | H | Y | M | R | F | P | Y | T | F | G | Q | G | T |
| rF1 V205C | F | T | L | T | I | S | S | L | Q | P | D | D | F | A | T | Y | Y | C | Q | H | Y | M | R | F | P | Y | T | F | G | Q | G | T |

| | 103 | 104 | 105 | 106 | 107 | 107a | 108 | 109 | 110 | 111 | 112 | 113 | 114 | 115 | 116 | 117 | 118 | 119 | 120 | 121 | 122 | 123 | 124 | 125 | 126 | 127 | 128 | 129 | 130 | 131 | 132 | 133 | 134 | 135 | 136 | 137 |
|---|---|---|---|---|---|---|---|---|---|---|---|---|---|---|---|---|---|---|---|---|---|---|---|---|---|---|---|---|---|---|---|---|---|---|---|---|
| rF1 light chain | K | L | E | I | K | . | R | T | A | A | A | P | S | V | F | I | F | P | P | S | D | E | Q | L | K | S | G | T | A | S | V | V | C | L | L | N |
| rF1 V205C | K | V | E | I | K | . | R | T | V | A | A | P | S | V | F | I | F | P | P | S | D | E | Q | L | K | S | G | T | A | S | V | V | C | L | L | N |

| | 138 | 139 | 140 | 141 | 142 | 143 | 144 | 145 | 146 | 147 | 148 | 149 | 150 | 151 | 152 | 153 | 154 | 155 | 156 | 157 | 158 | 159 | 160 | 161 | 162 | 163 | 164 | 165 | 166 | 167 | 168 | 169 | 170 | 171 | 172 | 173 | 174 | 175 |
|---|---|---|---|---|---|---|---|---|---|---|---|---|---|---|---|---|---|---|---|---|---|---|---|---|---|---|---|---|---|---|---|---|---|---|---|---|---|---|
| rF1 light chain | N | F | Y | P | R | E | A | K | V | Q | W | K | V | D | N | A | L | Q | S | G | N | S | Q | E | S | V | T | E | Q | D | S | K | D | S | T | Y | S | L |
| rF1 V205C | N | F | Y | P | R | E | A | K | V | Q | W | K | V | D | N | A | L | Q | S | G | N | S | Q | E | S | V | T | E | Q | D | S | K | D | S | T | Y | S | L |

| | 176 | 177 | 178 | 179 | 180 | 181 | 182 | 183 | 184 | 185 | 186 | 187 | 188 | 189 | 190 | 191 | 192 | 193 | 194 | 195 | 196 | 197 | 198 | 199 | 200 | 201 | 202 | 203 | 204 | 205 | 206 | 207 | 208 | 209 | 210 | 211 | 212 |
|---|---|---|---|---|---|---|---|---|---|---|---|---|---|---|---|---|---|---|---|---|---|---|---|---|---|---|---|---|---|---|---|---|---|---|---|---|---|
| rF1 light chain | S | S | T | L | T | L | S | K | A | D | Y | E | K | H | K | V | Y | A | C | E | V | T | H | Q | G | L | S | S | P | V | T | K | S | F | N | R | G |
| rF1 V205C | S | S | T | L | T | L | S | K | A | D | Y | E | K | H | K | V | Y | A | C | E | V | T | H | Q | G | L | S | S | P | C | T | K | S | F | N | R | G |

| | 213 | 214 | 215 | 216 |
|---|---|---|---|---|
| rF1 light chain | E | C | . | . |
| rF1 V205C | E | C | . | . |

US 8,617,556 B2

GRAM-POSITIVE BACTERIA SPECIFIC BINDING COMPOUNDS

CROSS-REFERENCE TO RELATED APPLICATIONS

This application is a divisional of U.S. patent application Ser. No. 12/837,358, filed Jul. 15, 2010 and claims priority to European Patent Application No. 09165558.9, filed Jul. 15, 2009, and U.S. Provisional Patent Application No. 61/225,878, filed Jul. 15, 2009, the disclosures of which are incorporated herein by reference in their entirety.

TECHNICAL FIELD

The invention relates to the fields of biology, immunology and medicine.

BACKGROUND OF THE INVENTION

Gram-positive microorganisms cause the majority of systemic infections. One important member of these Gram-positive pathogens is Staphylococcus aureus (S. aureus). About 20% of the population is a long-term carrier of S. aureus. S. aureus can cause a range of illnesses from minor skin infections, such as pimples, impetigo (may also be caused by Streptococcus pyogenes), boils, cellulitis folliculitis, furuncles, carbuncles, scalded skin syndrome and abscesses, to life-threatening diseases such as pneumonia, meningitis, osteomyelitis, endocarditis, Toxic shock syndrome (TSS), and septicemia. S. aureus is capable of infecting all kinds of organs and tissues. S. aureus infections occur in immunocompetent as well as immune compromised people. About 50% of the infections in US intensive care units are caused by this pathogen. Three hundred thousand S. aureus infections per year, resulting in 12,000 deaths, are reported in the US (see also Moran et al. NEMJ 355, 666-674 (2006)).

A major problem is the increasing antibiotic resistance of S. aureus. Methicillin-resistant S. aureus (MRSA) emerged in the 1960s. It was initially identified in health care settings. However, MRSA appears to be present among persons in the community which have not been hospitalized. Treatment of MRSA is difficult and expensive, due to the limited sensitivity of MRSA to antibiotics. However, very few alternatives of antibiotics are available. Vancomycin is often used to treat penicillin-resistant MRSA. U.S. Pat. No. 6,939,543 describes a murine antibody against lipoteichoic acid (LTA) which is capable of binding S. aureus. Based on this murine antibody, a recombinant chimeric mouse/human antibody was produced which contains human heavy and light chain constant domains. However, such chimeric mouse/human antibody has the disadvantage that murine sequences are present, which involves the risk of serious side effects when administered to humans.

SUMMARY OF THE INVENTION

Provided herein are antibodies or functional parts thereof or immunoglobulin chains or functional equivalents thereof, which comprise: (a) a heavy chain CDR1 sequence comprising a sequence which has at least 70% sequence identity to the sequence RFAMS (SEQ ID NO:1), and/or (b) a heavy chain CDR2 sequence comprising a sequence which has at least 70% sequence identity to the sequence SINNGNNPYYARSVQY (SEQ ID NO:2), and/or (c) a heavy chain CDR3 sequence comprising a sequence which has at least 70% sequence identity to the sequence DHPSSGWPTFDS (SEQ ID NO:3), and/or (d) a light chain CDR1 sequence comprising a sequence which has at least 70% sequence identity to the sequence RASENVGDWLA (SEQ ID NO:4), and/or, (e) a light chain CDR2 sequence comprising a sequence which has at least 70% sequence identity to the sequence KTSILES (SEQ ID NO:5), and/or (f) a light chain CDR3 sequence comprising a sequence which has at least 70% sequence identity to the sequence QHYXRFPYT, wherein X is I or M (SEQ ID NO:6). In some embodiments, the antibody or functional part thereof or immunoglobulin chain or functional equivalent thereof, which comprises: (a) a heavy chain CDR1 sequence comprising a sequence which has the sequence RFAMS (SEQ ID NO:1), and/or (b) a heavy chain CDR2 sequence comprising a sequence which has the sequence SINNGNNPYYARSVQY (SEQ ID NO:2), and/or (c) a heavy chain CDR3 sequence comprising a sequence which has the sequence DHPSSGWPTFDS (SEQ ID NO:3), and/or (d) a light chain CDR1 sequence comprising a sequence which has the sequence RASENVGDWLA (SEQ ID NO:4), and/or, (e) a light chain CDR2 sequence comprising a sequence which has the sequence KTSILES (SEQ ID NO:5), and/or (f) a light chain CDR3 sequence comprising a sequence which has the sequence QHYXRFPYT, wherein X is I or M (SEQ ID NO:6).

In some embodiments, the antibody or functional part or immunoglobulin chain or functional equivalent has a heavy chain sequence comprising a sequence which has at least 70% sequence identity to the sequence EVQLLESGGGLVQPGGSLRLSCAASG-FTLSRFAMSWVRQAPGRGLEWVASIN-NGNNPYYARSVQYRFTVSRDVSQNTVS-LQMNNLRAEDSATYFCAKDHPSSGWPTFDSWGPGT-LVTVSS (SEQ ID NO:7) and/or having a light chain sequence which has at least 70% sequence identity to the sequence DIQLTQSPSALPASVGDRVSITCRASEN-VGDWLAWYRQKPGKAPNLLIYKTSILES-GVPSRFSGSGSGTEFTLTISSLQPDDFA-TYYCQHYXRFPYTFGQGTKLEIKRTV, wherein X is I of M (SEQ ID NO:8).

In some embodiments, the antibody or functional part or immunoglobulin chain or functional equivalent has a heavy chain sequence comprising a sequence which has at least 70% sequence identity to the sequence EVQLLESGGGLVQPGGSLRLSCAASG-FTLSRFAMSWVRQAPGRGLEWVASIN-NGNNPYYARSVQYRFTVSRDVSQNTVS-LQMNNLRAEDSATYFCAKDHPSSGWPTFDSWGPGT-LVTVSS (SEQ ID NO:7) and/or having a light chain sequence which has at least 70% sequence identity to the sequence DIQLTQSPSALPASVGDRVSITCRASEN-VGDWLAWYRQKPGKAPNLLIYKTSILES-GVPSRFSGSGSGTEFTLTISSLQPDDFA-TYYCQHYXRFPYTFGQGTKLEIKRA, wherein X is I of M (SEQ ID NO:10).

In some embodiments, the antibody or functional part or immunoglobulin chain or functional equivalent has a heavy chain sequence comprising a sequence which has at least 70% sequence identity to the sequence EVQLLESGGGLVQPGGSLRLSCAASG-FTLSRFAMSWVRQAPGRGLEWVASIN-NGNNPYYARSVQYRFTVSRDVSQNTVS-LQMNNLRAEDSATYFCAKDHPSSGWPTFDSWGPGT-LVTVSS (SEQ ID NO:7) and/or having a light chain sequence which has at least 70% sequence identity to the sequence DIQLTQSPSALPASVGDRVSITCRASEN-VGDWLAWYRQKPGKAPNLLIYKTSILES- GVPSRFSGSGSGTEFTLTISSLQPDDFATYYCQHYX-RFPYTFGQGTKVEIKRTV, wherein X is I of M (SEQ ID NO:11).

In some embodiments, the antibody or functional part or immunoglobulin chain or functional equivalent has a heavy chain sequence comprising a sequence which has at least 70% sequence identity to the sequence EVQLVESGGGLVQPGGSLRLSCAASG-FTLSRFAMSWVRQAPGRGLEWVASIN-NGNNPYYARSVQYRFTVSRDVSQNTVS-LQMNNLRAEDSATYFCAKDHPSSGWPTFDSWGPGT-LVTVSS (SEQ ID NO:9) and/or having a light chain sequence which has at least 70% sequence identity to the sequence DIQLTQSPSALPASVGDRVSITCRASEN-VGDWLAWYRQKPGKAPNLLIYKTSILES-GVPSRFSGSGSGTEFTLTISSLQPDDFA-TYYCQHYXRFPYTFGQGTKLEIKRTV, wherein X is I of M (SEQ ID NO:8).

In some embodiments, the antibody or functional part or immunoglobulin chain or functional equivalent has a heavy chain sequence comprising a sequence which has at least 70% sequence identity to the sequence EVQLVESGGGLVQPGGSLRLSCAASG-FTLSRFAMSWVRQAPGRGLEWVASIN-NGNNPYYARSVQYRFTVSRDVSQNTVS-LQMNNLRAEDSATYFCAKDHPSSGWPTFDSWGPGT-LVTVSS (SEQ ID NO:9) and/or having a light chain sequence which has at least 70% sequence identity to the sequence DIQLTQSPSALPASVGDRVSITCRASEN-VGDWLAWYRQKPGKAPNLLIYKTSILES-GVPSRFSGSGSGTEFTLTISSLQPDDFA-TYYCQHYXRFPYTFGQGTKLEIKRA, wherein X is I of M (SEQ ID NO:10).

In some embodiments, the antibody or functional part or immunoglobulin chain or functional equivalent has a heavy chain sequence comprising a sequence which has at least 70% sequence identity to the sequence EVQLVESGGGLVQPGGSLRLSCAASG-FTLSRFAMSWVRQAPGRGLEWVASIN-NGNNPYYARSVQYRFTVSRDVSQNTVS-LQMNNLRAEDSATYFCAKDHPSSGWPTFDSWGPGT-LVTVSS (SEQ ID NO:9) and/or having a light chain sequence which has at least 70% sequence identity to the sequence DIQLTQSPSALPASVGDRVSITCRASEN-VGDWLAWYRQKPGKAPNLLIYKTSILES-GVPSRFSGSGSGTEFTLTISSLQPDDFA-TYYCQHYXRFPYTFGQGTKVEIKRTV, wherein X is I of M (SEQ ID NO:11).

In some embodiments of any of the antibodies or functional parts or immunoglobulin chains or functional equivalents, an asparagine has been replaced by another amino acid. In some embodiments, the asparagine is an asparagine at position 53 of the heavy chain, whereby the amino acid numbering is according to Kabat (1991). In some embodiments, the other amino acid is serine.

In some embodiments of any of the antibodies or functional parts or immunoglobulin chains or functional equivalents, at least one amino acid other than cysteine has been replaced with cysteine. In some embodiments, the at least one amino acid other than cysteine is valine at light chain position 205 and/or valine at light chain position 110, and/or alanine at heavy chain position 114, whereby the amino acid numbering is according to Kabat (1991).

The invention provides isolated antibodies that bind to in vivo-grown *S. aureus*. In some embodiments, the antibody is human.

The invention also provides antibodies or functional parts or immunoglobulin chains or functional equivalents capable of binding an SD-repeat dependent epitope.

Also provided herein are antibodies or functional parts or immunoglobulin chains or functional equivalents capable of binding to *S. aureus* ClfA, ClfB, SdrC, SdrD and SdrE.

Provided herein are antibodies or functional parts or immunoglobulin chains or functional equivalents which are capable of competing with any antibody or functional part or immunoglobulin chain or functional equivalent described herein for binding to a *Staphylococcus* species.

In some embodiments of any of the antibodies or functional parts or immunoglobulin chains or functional equivalents, the antibody or functional part or immunoglobulin chain or functional equivalent is a human antibody.

Provided herein are further isolated, synthetic or recombinant nucleic acid sequences with a length of at least 15 nucleotides, or functional equivalents thereof, encoding at least one CDR sequence of any of the antibodies or functional parts or immunoglobulin chains or functional equivalents described herein.

The invention provides isolated, synthetic or recombinant nucleic acid sequences, or functional equivalents thereof, comprising a sequence which has at least 70% sequence identity to a sequence selected from the group consisting of cgctttgccatgagc (SEQ ID NO:12), tcgatcaataatgggaataac-ccatactacgcacggtcggtacaatac (SEQ ID NO:13), gatcaccctag-tagtggctggcccaccttgactcc (SEQ ID NO:14), cgggccagt-gaaaacgttggtgactggttggcc (SEQ ID NO:15), aagacatctattctagaaagt (SEQ ID NO:16) and caacac-tatatacgtttcccgtacact (SEQ ID NO:17). In some embodiment, the nucleic acid sequence or functional equivalent comprises a sequence which has at least 70% sequence identity to at least part of a nucleotide sequence as depicted in FIG. 1, said part having at least 15 nucleotides and encoding at least one CDR region.

Also provided herein are isolated, synthetic or recombinant nucleic acid sequences, or functional equivalents thereof, comprising a sequence encoding an amino acid sequence which has at least 70% sequence identity to the sequence RFAMS (SEQ ID NO:1), and/or at least 70% sequence identity to the sequence SINNGNNPYYARSVQY (SEQ ID NO:2), and/or at least 70% sequence identity to the sequence DHPSSGWPTFDS (SEQ ID NO:3), and/or at least 70% sequence identity to the sequence RASENVGDWLA (SEQ ID NO:4), and/or at least 70% sequence identity to the sequence KTSILES (SEQ ID NO:5), and/or at least 70% sequence identity to the sequence QHYXRFPYT, wherein X is I or M (SEQ ID NO:6), and/or at least 70% sequence identity to the sequence EVQLLESGGGLVQPGGSL-RLSCAASGFTLSRFAMSWVRQAPGR-GLEWVASINNGNNPYYARSVQYRFTVS-RDVSQNTVSLQMNNLRAEDSATYFCAKDHPSSGWP-TFDSWGPGTLVTVSS (SEQ ID NO:7), and/or at least 70% sequence identity to the sequence DIQLTQSPSALPAS-VGDRVSITCRASENVGDWLAWYRQK-PGKAPNLLIYKTSILESGVPSRFSGSGS-GTEFTLTISSLQPDDFATYYCQHYXRFPYTFGQGTK-LEIKRTV, wherein X is I or M (SEQ ID NO:8).

Provided herein are any antibodies or functional parts or an immunoglobulin chains or functional equivalents thereof or any nucleic acid sequence or functional equivalents thereof described herein for use as a medicament and/or prophylactic agent.

Provided herein are also any antibodies or functional parts or an immunoglobulin chains or functional equivalents thereof or any nucleic acid sequences or functional equivalents thereof described herein for use as a medicament and/or prophylactic agent for at least in part treating and/or preventing a Gram-positive bacterium-related disorder. Methods of treating and/or preventing a Gram-positive bacterium-related disorder comprising administering an effective amount of any antibodies or functional parts or an immunoglobulin chains or functional equivalents thereof or any nucleic acid sequences or functional equivalents thereof described herein are further provided herein. Provided are uses of any antibodies or functional parts or an immunoglobulin chains or functional equivalents thereof or any nucleic acid sequences or functional equivalents thereof described herein for the preparation of a medicament and/or prophylactic agent for at least in part treating and/or preventing a Gram-positive bacterium-related disorder.

Provided herein are pharmaceutical compositions comprising any antibodies or functional parts or an immunoglobulin chains or functional equivalents thereof or any nucleic acid sequences or functional equivalents thereof described herein and a pharmaceutical acceptable carrier, diluent or excipient.

Also provided herein are isolated or recombinant antibodies producing cell capable of producing any antibodies or functional parts or immunoglobulin chains or functional equivalents described herein. Provided are methods for producing any antibodies or functional parts or immunoglobulin chains or functional equivalents described herein, comprising providing a cell with any nucleic acid sequences or functional equivalents described herein and allowing said cell to translate the nucleic acid sequences or functional equivalents described herein, thereby producing any of the antibodies or functional parts or immunoglobulin chains or functional equivalents described herein. In some embodiments, the method further comprises harvesting, purifying and/or isolating any of the antibodies or functional parts or immunoglobulin chains or functional equivalents described herein.

Provided herein are uses of any antibodies or functional parts or an immunoglobulin chains or functional equivalents thereof or any nucleic acid sequences or functional equivalents thereof described herein for diagnosis of a *Staphylococcus* infection. Methods for diagnosing a *Staphylococcus* infection comprising contacting a sample with any antibodies or functional parts or an immunoglobulin chains or functional equivalents thereof or any nucleic acid sequences or functional equivalents thereof described herein are also provided. Provided are also antibodies or functional parts thereof or an immunoglobulin chains or functional equivalents thereof described herein for use in the diagnosis of a *Staphylococcus* infection.

The invention also provides use of any antibodies or functional parts or an immunoglobulin chains or functional equivalents thereof or any nucleic acid sequences or functional equivalents thereof described herein for detecting *S. aureus* and/or *S. epidermidis*. Methods for detecting *S. aureus* and/or *S. epidermidis* comprising contacting a sample with any antibodies or functional parts or an immunoglobulin chains or functional equivalents thereof or any nucleic acid sequences or functional equivalents thereof described herein are also provided.

Provided are also methods for isolating *S. aureus* and/or *S. epidermidis* bacteria comprising contacting a sample (e.g. solution) with any antibodies or functional parts or an immunoglobulin chains or functional equivalents thereof described herein.

BRIEF DESCRIPTION OF THE DRAWINGS

FIG. 1: Heavy chain and light chain sequences of antibody F1. Heavy chain: Fw1 amino acid sequence (SEQ ID NO:37); CDR1 amino acid sequence (SEQ ID NO:1); Fw2 amino acid sequence (SEQ ID NO:39); CDR2 amino acid sequence (SEQ ID NO:2); Fw3 amino acid sequence (SEQ ID NO:41); CDR3 amino acid sequence (SEQ ID NO:3); Fw4 amino acid sequence (SEQ ID NO:43). Fw1 nucleotide sequence (SEQ ID NO:37); CDR1 nucleotide sequence (SEQ ID NO:12); Fw2 nucleotide sequence (SEQ ID NO:39); CDR2 nucleotide sequence (SEQ ID NO:13); Fw3 nucleotide sequence (SEQ ID NO:41); CDR3 nucleotide sequence (SEQ ID NO:14); Fw4 nucleic acid sequence (SEQ ID NO:43). Light chain: Fw1 amino acid sequence (SEQ ID NO:47); CDR1 amino acid sequence (SEQ ID NO:4); Fw2 amino acid sequence (SEQ ID NO:49); CDR2 amino acid sequence (SEQ ID NO:5); Fw3 amino acid sequence (SEQ ID NO:51); CDR3 amino acid sequence (SEQ ID NO:6); Fw4 amino acid sequence (SEQ ID NO:53). Fw1 nucleotide sequence (SEQ ID NO:47); CDR1 nucleotide sequence (SEQ ID NO:15); Fw2 nucleotide sequence (SEQ ID NO:49); CDR2 nucleotide sequence (SEQ ID NO:16); Fw3 nucleotide sequence (SEQ ID NO:51); CDR3 nucleotide sequence (SEQ ID NO:17); Fw4 nucleic acid sequence (SEQ ID NO:53).

FIG. 9: Sequences of heavy chain rF1 (SEQ ID NO:55) and heavy chain A114C (SEQ ID NO:56) (a) and light chain rF1 (SEQ ID NO:57) and light chain V205C (SEQ ID NO:58) (b) variants of rF1. Numbering according to Kabat (1991), boxes: CDRs.

DETAILED DESCRIPTION OF THE INVENTION

Figure 2A:
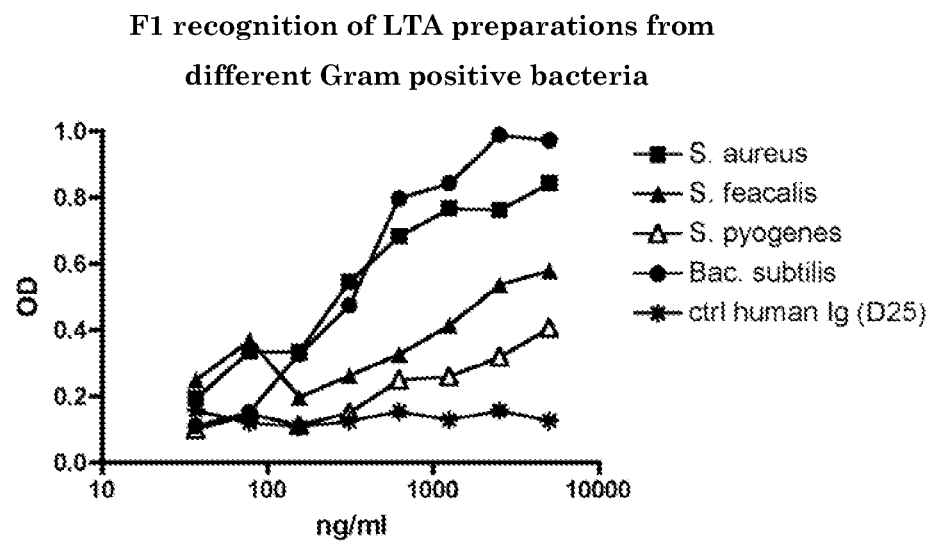
FIG. 2: F1 antibody binds to LTA preparations from several Gram-positive bacteria. (a) LTA preparations were derived from Sigma and tested in a capture ELISA with a mouse polyclonal anti-LTA or (b) a highly purified set of LTA preparations derived from W. Fischer. D25, a human anti-RSV antibody was used as non-specific negative control and a mouse monoclonal anti-LTA antibody as a positive control.

It is an object of the present invention to provide means and methods for counteracting and/or preventing Gram-positive bacteria-related diseases. It is a further object of the invention to provide alternative and/or improved binding compounds against various Gram-positive bacteria, preferably *Staphylococcus* species, more preferably MRSA. It is a further object of the invention to provide human binding compounds against various Gram-positive bacteria, preferably *Staphylococcus* species, more preferably MRSA.

The present invention provides antibodies, functional parts thereof or immunoglobulin chains or functional equivalents thereof capable of specifically binding *Staphylococcus* species in their natural context. Therefore, they are useful for counteracting and/or preventing and/or diagnosing disorders related to the presence of *Staphylococcus* species. Preferably, *S. aureus* is counteracted. In a particularly preferred embodiment, MRSA is counteracted. Another preferred *Staphylococcus* species which is counteracted is *Staphylococcus epidermidis*.

*Staphylococcus epidermidis* is usually non-pathogenic, but patients with a compromised immune system are often at risk for developing an infection. Infections can be both hospital and community acquired, but they are more of a threat to hospital patients. Most susceptible to infection with *S. epidermidis* are intravenous drug users, newborns, elderly, and those using catheters or other artificial appliances. Infections are associated with intravascular devices (prosthetic heart valves, shunts, etc.) but also commonly occur in prosthetic joints, catheters, and large wounds. Symptoms include fever, headache, fatigue, anorexia and dyspnea.

In a preferred embodiment, the present invention provides isolated or recombinant human antibodies, functional parts thereof or immunoglobulin chains or functional equivalents thereof capable of specifically binding *Staphylococcus* species. Human antibodies and functional parts according to the invention are capable of binding *Staphylococcus* species in its natural context, so that various *Staphylococcus* species are counteracted upon administration of said antibodies, functional parts thereof or immunoglobulin chains or functional equivalents thereof. Said human antibodies, functional parts thereof or immunoglobulin chains or functional equivalents thereof are therefore particularly suitable for treatment or prevention of infection by such *Staphylococcus* species. Said human antibodies, functional parts thereof or immunoglobulin chains or functional equivalents thereof according to the invention are more suitable for therapeutic and/or prophylactic use for human individuals, as compared to chimeric antibodies, because of the absence of non-human sequences. This significantly reduces the risk of adverse side effects.

One particularly preferred antibody according to the present invention is the antibody designated "F1", which has heavy chain and light chain variable domain sequences as depicted in FIG. 1. The term "F1" as used herein encompasses all F1 antibodies, for instance isolated or recombinantly produced F1. Recombinantly produced F1 is herein also called "rF1". The CDR sequences of F1, which in particular contribute to the antigen-binding properties of F1, are also depicted in FIG. 1. Antibody F1 is fully human, is capable of specifically binding *Staphylococcus* species such as *S. aureus* and *S. epidermidis* and is therefore preferred for therapeutic use for human individuals.

Importantly, antibody F1 is capable of binding whole bacteria in vivo as well as in vitro. Further provided is therefore an isolated or recombinant human antibody or a functional part thereof, which is capable of specifically binding *S. aureus* and/or *S. epidermidis*. Furthermore, antibody F1 is capable of binding to bacteria that have been grown in infected tissue of, for example, an animal. Provided is therefore an isolated antibody that binds to in vivo-grown *S. aureus*, wherein "in vivo-grown" is defined as grown in infected tissue of an animal during infection with *S. aureus*. Also provided is an isolated, recombinant or synthetic immunoglobulin chain or functional equivalent thereof comprising at least one CDR sequence of a human immunoglobulin variable region which is specific for *S. aureus* and/or *S. epidermidis*.

A functional part of an antibody is defined as a part which has at least one shared property as said antibody in kind, not necessarily in amount. Said functional part is capable of binding the same antigen as said antibody, albeit not necessarily to the same extent. A functional part of an antibody preferably comprises a single domain antibody, a single chain antibody, a nanobody, an unibody, a single chain variable fragment (scFv), a Fab fragment or a F(ab')$_2$ fragment.

A functional part of an antibody is also produced by altering an antibody such that at least one property—preferably an antigen-binding property—of the resulting compound is essentially the same in kind, not necessarily in amount. This is done in many ways, for instance through conservative amino acid substitution, whereby an amino acid residue is substituted by another residue with generally similar properties (size, hydrophobicity, etc), such that the overall functioning is likely not to be seriously affected.

As is well known by the skilled person, a heavy chain of an antibody is the larger of the two types of chains making up an immunoglobulin molecule. A heavy chain comprises constant domains and a variable domain, which variable domain is involved in antigen binding. A light chain of an antibody is the smaller of the two types of chains making up an immunoglobulin molecule. A light chain comprises a constant domain and a variable domain. The variable domain is, together with the variable domain of the heavy chain, involved in antigen binding.

Complementary-determining regions (CDRs) are the hypervariable regions present in heavy chain variable domains and light chain variable domains. The CDRs of a heavy chain and the connected light chain of an antibody together form the antigen-binding site.

A functional equivalent of an immunoglobulin chain is defined herein as an artificial binding compound, comprising at least one CDR sequence of an immunoglobulin chain.

Now that the present invention provides the insight that the CDR sequences depicted in FIG. 1 provide desired binding characteristics, a skilled person is well capable of generating variants comprising at least one altered CDR sequence. For instance, conservative amino acid substitution is applied. It is also possible to alter at least one CDR sequence depicted in FIG. 1 in order to generate a variant antibody, or a functional part thereof, with at least one altered property as compared to F1. Preferably, an antibody or functional part is provided comprising a CDR sequence which is at least 70% identical to a CDR sequence as depicted in FIG. 1, so that the favorable binding characteristics of F1 are at least in part maintained or even improved. A CDR sequence as depicted in FIG. 1 is preferably altered such that the resulting antibody or functional part comprises at least one improved property, such as for instance an improved binding affinity, selectivity and/or stability, as compared to F1. Variant antibodies or functional parts thereof comprising an amino acid sequence which is at least 70% identical to a CDR sequence as depicted in FIG. 1 are therefore also within the scope of the present invention. Various methods are available in the art for altering an amino acid sequence. For instance, a heavy chain or light chain sequence with a desired CDR sequence is artificially synthesized. Preferably, a nucleic acid sequence encoding a CDR sequence is mutated, for instance using random—or site-directed—mutagenesis.

In one embodiment the invention therefore provides an antibody or functional part thereof or immunoglobulin chain or functional equivalent thereof, which comprises:
 a heavy chain CDR1 sequence comprising a sequence which has at least 70% sequence identity to the sequence RFAMS (SEQ ID NO:1), and/or
 a heavy chain CDR2 sequence comprising a sequence which has at least 70% sequence identity to the sequence SINNGNNPYYARSVQY (SEQ ID NO:2), and/or
 a heavy chain CDR3 sequence comprising a sequence which has at least 70% sequence identity to the sequence DHPSSGWPTFDS (SEQ ID NO:3).

Further provided is an antibody or functional part thereof or immunoglobulin chain or functional equivalent thereof, which comprises:
 a light chain CDR1 sequence comprising a sequence which has at least 70% sequence identity to the sequence RASENVGDWLA (SEQ ID NO:4), and/or
 a light chain CDR2 sequence comprising a sequence which has at least 70% sequence identity to the sequence KTSILES (SEQ ID NO:5), and/or
 a light chain CDR3 sequence comprising a sequence which has at least 70% sequence identity to the sequence QHYXRFPYT, wherein X is I or M (SEQ ID NO:6).

The above mentioned CDR sequences are the CDR sequences of antibody F1; VH IgHV3-23 and VL IgKV1-5, and variants thereof. Binding compounds comprising CDR sequences with at least 70% sequence identity to F1 CDRs are particularly suitable for counteracting and/or preventing (the effects of) infections by *S. aureus* and/or *S. epidermidis*. It was found that a variant of F1, comprising VH IgHV3-23 and VL IgKV1-5, in which the isoleucine in light chain CDR3 of the light chain was altered to a methionine, was still capable of specifically binding *Staphylococcus* species such as *S. aureus* and *S. epidermidis*.

Preferably, a binding compound according to the invention comprises a CDR sequence which is at least 75%, more preferably at least 80%, more preferably at least 85%, more preferably at least 86%, more preferably at least 87%, more preferably at least 88%, more preferably at least 89%, more preferably at least 90% identical to at least one of the CDR sequences depicted in FIG. 1. Most preferably, a binding compound according to the invention comprises a CDR sequence which is at least 91%, more preferably at least 92%, more preferably at least 93%, more preferably at least 94%, more preferably at least 95% identical to at least one of the CDR sequences depicted in FIG. 1. The particularly preferred antibody F1, described above, comprises CDR sequences which consist of the CDR sequences depicted in FIG. 1. A particularly preferred embodiment according to the invention thus provides an isolated, synthetic or recombinant antibody or a functional equivalent thereof which is capable of specifically binding *S. aureus* and/or *S. epidermidis* and which comprises:
 a heavy chain CDR1 sequence comprising the sequence RFAMS (SEQ ID NO:1), and/or
 a heavy chain CDR2 sequence comprising the sequence SINNGNNPYYARSVQY (SEQ ID NO:2), and/or
 a heavy chain CDR3 sequence comprising the sequence DHPSSGWPTFDS (SEQ ID NO:3), and/or
 a light chain CDR1 sequence comprising the sequence RASENVGDWLA (SEQ ID NO:4), and/or
 a light chain CDR2 sequence comprising the sequence KTSILES (SEQ ID NO:5), and/or
 a light chain CDR3 sequence comprising the sequence QHYXRFPYT, wherein X is I or M (SEQ ID NO:6).

In one embodiment a binding compound is provided which comprises the heavy chain CDR1 and CDR2 sequences and the light chain CDR1 and CDR2 sequences as depicted in FIG. 1, or sequences that are at least 70%, preferably at least 75%, more preferably at least 80%, more preferably at least 81%, more preferably at least 82%, more preferably at least 83%, more preferably at least 84%, more preferably at least 85% identical thereto. Further provided is therefore an isolated, synthetic or recombinant antibody or a functional part thereof or an immunoglobulin chain or a functional equivalent thereof which comprises a heavy chain CDR1 sequence comprising a sequence which is at least 70% identical to the sequence RFAMS (SEQ ID NO:1) and a heavy chain CDR2 sequence comprising a sequence which is at least 70% identical to the sequence SINNGNNPYYARSVQY (SEQ ID NO:2) and a light chain CDR1 sequence comprising a sequence which is at least 70% identical to the sequence RASENVGDWLA (SEQ ID NO:4) and a light chain CDR2 sequence comprising a sequence which is at least 70% identical to the sequence KTSILES (SEQ ID NO:5). Said binding compound preferably comprises CDR sequences which are at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, most preferably at least 95% identical to the above mentioned heavy chain CDR sequences and light chain CDR sequences. Preferably, said binding compound also comprises a heavy chain CDR3 sequence comprising a sequence which is at least 70% identical to the sequence DHPSSGWPTFDS (SEQ ID NO:3), and/or a light chain CDR3 sequence comprising a sequence which is at least 70% identical to the sequence QHYXRFPYT, wherein X is I or M (SEQ ID NO:6). A binding compound comprising the above mentioned heavy chain CDR1, CDR2 and CDR3 sequences as well as the above mentioned light chain CDR1, CDR2 and CDR3 sequences is also provided.

Now that a human antibody capable of specifically binding *Staphylococcus* species has been provided by the present invention, it has become possible to produce an immunoglobulin chain or functional equivalent thereof comprising at least one CDR sequence of a human immunoglobulin variable domain which is specific for *Staphylococcus* species. Further provided is thus an isolated, recombinant or synthetic immunoglobulin chain or functional equivalent thereof comprising at least one CDR sequence of a human immunoglobulin variable region which is specific for *Staphylococcus* species. In a preferred embodiment, a human antibody is provided. Optionally, said at least one human CDR sequence or at least one sequence in at least one of the framework regions is optimized, preferably in order to improve binding efficacy or stability. This is for instance done by mutagenesis experiments where after the stability and/or binding efficacy of the resulting compounds are preferably tested and an improved binding compound is selected.

Besides optimizing CDR sequences in order to improve binding efficacy or stability, it is often advantageous to optimize at least one sequence in at least one of the framework regions. This is preferably done in order to improve binding efficacy or stability. Framework sequences are for instance optimized by mutating a nucleic acid molecule encoding such framework sequence where after the characteristics of the resulting antibody—or functional part—are preferably tested. This way, it is possible to obtain improved antibodies or functional parts. In a preferred embodiment, human germline sequences are used for framework regions in antibodies or functional parts thereof or immunoglobulin chains or functional equivalents according to the invention. The use of germline sequences preferably minimizes the risk of immunogenicity of said antibodies, immunoglobulin chains or functional equivalents or parts, because these sequences are less likely to contain somatic alterations which are unique to individuals from which the framework regions are derived, and may cause an immunogenic response when applied to another human individual.

Antibodies or functional parts thereof or immunoglobulin chains or functional equivalents thereof comprising a heavy chain amino acid sequence which has at least 70% sequence identity to the heavy chain sequence as depicted in FIG. 1 are also provided. Such heavy chain sequence provides desired binding properties, as evidenced by antibody F1. Moreover, light chain amino acid sequences which have at least 70% sequence identity to the light chain sequence as depicted in FIG. 1, and a light chain sequence in which an isoleucine in CDR3 is altered to methionine, also provide desired binding properties, as evidenced by antibody F1, and a variant of antibody F1 comprising said alteration. Further provided is therefore an antibody or functional part or immunoglobulin chain or functional equivalent according to the invention, having a heavy chain sequence comprising a sequence which has at least 70% sequence identity to the sequence EVQLLESGGGLVQPGGSLRLSCAASG-FTLSRFAMSWVRQAPGRGLEWVASIN-NGNNPYYARSVQYRFTVSRDVSQNTVS-LQMNNLRAEDSATYFCAKDHPSSGWPTFDSWGPGT-LVTVSS (SEQ ID NO:7) and/or having a light chain sequence which has at least 70% sequence identity to the sequence DIQLTQSPSALPASVGDRVSITCRASEN-VGDWLAWYRQKPGKAPNLLIYKTSILES-GVPSRFSGSGSGTEFTLTISSLQPDDFA-TYYCQHYXRFPYTFGQGTKLEIKRTV, wherein in X is I or M (SEQ ID NO:8).

Several variants of the F1 antibody have been developed, besides the variant indicated herein above in which an isoleucine in light chain CDR3 is altered to methionine. These variants are capable of binding to Staphylococcus species. Examples of such antibody variants include antibodies or functional parts or immunoglobulin chains or functional equivalents according to the invention, having a heavy chain sequence comprising the sequence EVQLVESGGGLVQPGGSLRLSCAASG-FTLSRFAMSWVRQAPGRGLEWVASIN-NGNNPYYARSVQYRFTVSRDVSQNTVS-LQMNNLRAEDSATYFCAKDHPSSGWPTFDSWGPGT-LVTVSS (SEQ ID NO:9), and/or the sequence EVQLLESGGGLVQPGGSLRLSCAASG-FTLSRFAMSWVRQAPGRGLEWVASIN-NGNNPYYARSVQYRFTVSRDVSQNTVS-LQMNNLRAEDSATYFCAKDHPSSGWPTFDSWGPGT-LVTVSS (SEQ ID NO:7), and a light chain sequence comprising the sequence DIQLTQSPSALPASVGDRVSITCRA-SENVGDWLAWYRQKPGKAPN-LLIYKTSILESGVPSRFSGSGSGTEFTLTISSLQPDDFA-TYYCQHYXRFPYTFGQGTKLEIKRA, wherein X is I of M (SEQ ID NO:10), and/or the sequence DIQLTQSPSAL-PASVGDRVSITCRASENVGDWLAWYRQK-PGKAPNLLIYKTSILESGVPSRFSGSGS-GTEFTLTISSLQPDDFATYYCQHYXRFPYTFGQGTKV-EIKRTV, wherein X is I of M (SEQ ID NO:11), and/or the sequence DIQLTQSPSALPASVGDRVSITCRASEN-VGDWLAWYRQKPGKAPNLLIYKTSILES-GVPSRFSGSGSGTEFTLTISSLQPDDFA-TYYCQHYXRFPYTFGQGTKLEIKRTV, wherein X is I of M (SEQ ID NO:8).

An antibody or functional part or immunoglobulin chain or functional equivalent thereof according to the invention specifically binds to proteins comprising a serine-aspartate (SD) repeat. SD repeat (Sdr) proteins are cell-surface-associated proteins that are present in several bacteria such as *Staphylococcus* species. Sdr proteins in general comprise an amino-terminal signal sequence, a functional domain called the A region, an SD repeat region, a cell wall-spanning region, a LPXTG motif, a hydrophobic membrane-spanning domain, and a series of positively charged residues. The LPXTG motif is the target of a transpeptidase that cleaves the motif between threonine and glycine residues and anchors the protein to the peptidoglycan of the cell wall of gram-positive bacteria. Sdr proteins are thought to interact with host molecules. Known Sdr proteins include ClfA (SdrA), ClfB (SdrB), SdrC, SdrD and SdrE of *S. aureus*, SdrF, SdrG and SdrH of *S. epidermidis*, SdrI of *S. saprophyticus*, SdrX of *S. capitis*, and SdrY and SdrZ of *S. caprae*.

Therefore, a preferred antibody or functional part thereof or immunoglobulin chain or functional equivalent according to the invention specifically binds *S. aureus, S. epidermidis, S. saprophyticus, S. capitis*, and *S. caprae*. It is preferred that said antibody, immunoglobulin chain or functional equivalent or part thereof binds to ClfA (SdrA), ClfB (SdrB), SdrC, SdrD and SdrE of *S. aureus*, SdrF, SdrG and SdrH of *S. epidermidis*, SdrI of *S. saprophyticus*, SdrX of *S. capitis*, and SdrY and SdrZ of *S. caprae*. The epitope of the antibody, immunoglobulin chain or functional equivalent or part thereof according to the invention comprises an SD repeat-dependent epitope in Sdr proteins, for instance SD repeat-dependent epitopes as present in *S. aureus* ClfA, ClfB, SdrC, SdrD and SdrE. An SD repeat-dependent epitope is herein defined as an epitope recognized by antibody F1, which epitope require the presence of at least part of an SD repeat region as present in, but not limited to, *S. aureus* ClfA, ClfB, SdrC, SdrD and SdrE and *S. epidermidis* SdrF, SdrG and SdrH. In one embodiment said epitope may comprise at least part of a molecule that binds to, or is associated with an Sdr protein. Examples of such molecules include, but are not limited to, amino acids, peptides, proteins, sugars and sugar residues. In another embodiment, said epitope comprises modifications of the SD repeat region. Said modifications comprise, for example, but are not limited to, glycosylation, amidation and/or phosphorylation. It will be clear to a skilled person that combination of these two embodiments is also possible.

Therefore, the invention provides an antibody or functional part or immunoglobulin chain or functional equivalent according to the invention capable of binding an SD repeat-dependent epitope. Also provided is an antibody or functional part or immunoglobulin chain or functional equivalent capable of binding to *S. aureus* ClfA, ClfB, SdrC, SdrD and SdrE. Further provided is an antibody or functional part or immunoglobulin chain or functional equivalent which is capable of competing with an antibody or functional part or immunoglobulin chain or functional equivalent according to the present invention for binding to a *Staphylococcus* species, preferably *S. aureus* and/or *S. epidermidis* and/or *S. saprophyticus* and/or *S. capitis* and/or *S. caprae*, more preferably MRSA.

A disadvantage of antibodies is that their stability may be reduced, for example under harsh conditions. For instance deamidation, the removal of a functional amide group, may occur. Deamidation is a protein degradation pathway that may affect the biological functions of proteins, and which occurs mainly at asparagine residues, and to a lower extent at glutamine residues. In one embodiment, therefore, deamidation of an antibody or functional part thereof or immunoglobulin chain or functional equivalent thereof according to the invention is prevented by replacing an asparagine or glutamine by another amino acid. An asparagine is preferably replaced by an amino acid other than glutamine, because deamidation may also occur at a glutamine residue. Replacement of an asparagine preferably does not substantially affect binding affinity of an antibody according to the invention to an antigen. In one embodiment deamidation of an asparagine at position 53 of the heavy chain (numbering according to Kabat, 1991) is prevented by replacing said asparagine by another amino acid. By preventing deamidation of an asparagine at position 53 the stability of an antibody or functional part thereof or immunoglobulin chain or functional equivalent thereof according to the invention is preferably increased. As is shown in the examples, despite the fact that said asparagine is located in a CDR, replacing an asparagine at said position does not substantially affect the binding affinity for an antigen of an antibody or functional part thereof or immunoglobulin chain or functional equivalent thereof according to the invention. An asparagine at position 53 of the heavy chain is preferably replaced by an amino acid other than glutamine, more preferably an asparagine at said position is replaced by serine. Therefore, also provided by the invention is therefore an antibody or functional part or immunoglobulin chain or functional equivalent according to the invention, wherein an asparagine, preferably an asparagine at position 53 of the heavy chain, is replaced by another amino acid, preferably serine.

In one embodiment, an antibody or functional part thereof or immunoglobulin chain or functional equivalent thereof according to the invention is coupled to another moiety to form antibody-drug conjugates. An antibody or functional part thereof or immunoglobulin chain or functional equivalent thereof according to the invention is for instance coupled to a cytotoxic agent, such as an antibiotic. The term "cytotoxic agent" as used herein refers to a substance that reduces or blocks the function, or growth, of bacteria and/or causes destruction of bacteria. Said other moiety, for example a cytotoxic agent, is preferably coupled to said antibody or functional part thereof through a thiol group. Therefore, preferably one or more cysteines are incorporated into said antibody or functional part thereof or immunoglobulin chain or functional equivalent thereof. Cysteines contain a thiol group and therefore, incorporation of one or more cysteines into, or replacement of one or more amino acids by one or more cysteines of an antibody or functional part thereof according to the invention enable coupling thereof to another moiety. Said one or more cysteines are preferably introduced into an antibody of functional equivalent thereof according to the invention at a position where it does not influence folding of said antibody or functional equivalent, and does not alter antigen binding or effector function. The invention therefore provides an antibody or functional part thereof or immunoglobulin chain or functional equivalent thereof according to the invention wherein at least one amino acid other than cysteine has been replaced by a cysteine. Preferably at least two amino acids other than cysteine have been replaced by cysteine. In a preferred embodiment, said at least one amino acid other than cysteine is valine at light chain position 15, and/or alanine at light chain position 144, and/or serine at light chain position 168, and/or valine at light chain position 205 and/or valine at light chain position 110, and/or alanine at heavy chain position 84, and/or alanine at heavy chain position 114, and/or alanine at heavy chain position 168, and/or serine at heavy chain position 172, more preferably valine at light chain position 205 and/or valine at light chain position 110, and/or alanine at heavy chain position 114 (numbering according to Kabat, 1991). A skilled person will understand that, as an alternative or in addition, one or more other amino acids of the heavy and/or light chain can be replaced by cysteine if the replacement does not influence folding of said antibody or functional equivalent, and does not alter antigen binding or effector function.

In international patent applications WO2006/034488, WO2008/141044, WO2009/052249, WO2009/012256, WO2009/012268 and WO2009/099728 methods for engineering antibodies with reactive cysteine residues are described as well as amino acid positions suitable for cysteine engineering.

An antibody or functional part or immunoglobulin chain or functional equivalent according to the invention preferably comprises a variable heavy chain sequence and/or a variable light chain sequence which is at least 75%, more preferably at least 80%, more preferably at least 85%, more preferably at least 90%, most preferably at least 95% identical to a heavy chain sequence and/or the light chain sequence as depicted in FIG. 1, or a light chain sequence as depicted in FIG. 1 in which the isoleucine in CDR3 is altered to a methionine. The higher the identity, the more closely said binding compound resembles antibody F1. An antibody or functional part or immunoglobulin chain or functional equivalent according to the invention preferably comprises a heavy chain as well as a light chain which resemble the heavy and light chain of F1. Further provided is therefore an antibody or functional part thereof or immunoglobulin chain or functional equivalent thereof comprising a heavy chain sequence and a light chain sequence which are at least 70%, more preferably at least 80%, more preferably at least 85%, more preferably at least 90%, most preferably at least 95% identical to the heavy chain sequence and the light chain sequence as depicted in FIG. 1, or a light chain sequence as depicted in FIG. 1 in which the isoleucine in CDR3 is altered to a methionine. In one embodiment an antibody or functional part is provided which has a heavy chain sequence as depicted in FIG. 1 and a light chain sequence as depicted in FIG. 1 or a light chain sequence as depicted in FIG. 1 in which the isoleucine in CDR3 is altered to a methionine.

One embodiment provides an antibody or functional part thereof or immunoglobulin chain or functional equivalent thereof comprising a heavy chain sequence consisting of the heavy chain sequence as depicted in FIG. 1, and/or comprising a light chain sequence consisting of the light chain sequence as depicted in FIG. 1 or a light chain sequence as depicted in FIG. 1 in which the isoleucine in CDR3 is altered to a methionine. Alternatively, as is well known by the skilled person, it is possible to generate a shortened heavy chain or light chain sequence while maintaining a binding property of interest. Preferably, such a shortened heavy chain or light chain is generated which has a shorter constant region, as compared to the original heavy or light chain. The variable domain is preferably maintained. For instance, a Fab fragment or F(ab')₂ fragment or a single domain antibody or a single chain antibody or a nanobody or an unibody or a scFv fragment based on a heavy chain sequence or light chain sequence depicted in FIG. 1 is produced. A functional part of an antibody comprising at least a functional part of a sequence as depicted in FIG. 1, or a light chain sequence as depicted in FIG. 1 in which the isoleucine in CDR3 is altered to a methionine, is therefore also provided. Said functional part has a length of at least 20 amino acids and comprises at least one sequence selected from the group consisting of a sequence which is at least 70% identical to the heavy chain CDR1 sequence depicted in FIG. 1 and a sequence which is at least 70% identical to the heavy chain CDR2 sequence depicted in FIG. 1 and a sequence which is at least 70% identical to the heavy chain CDR3 sequence depicted in FIG. 1 and a sequence which is at least 70% identical to the light chain CDR1 sequence depicted in FIG. 1 and a sequence which is at least 70% identical to the light chain CDR2 sequence depicted in FIG. 1 and a sequence which is at least 70% identical to the light chain CDR3 sequence depicted in FIG. 1, or a light chain CDR3 sequence as depicted in FIG. 1 in which the isoleucine is altered to a methionine.

The invention further provides an isolated, synthetic or recombinant nucleic acid sequence or a functional equivalent thereof with a length of at least 15 nucleotides, preferably at least 30 nucleotides, more preferably at least 50 nucleotides, more preferably at least 75 nucleotides, encoding a binding compound according to the invention. Such nucleic acid is for instance isolated from a B-cell which is capable of producing an antibody according to the invention. A preferred embodiment provides a nucleic acid sequence comprising a sequence which has at least 70% sequence identity to at least 15 nucleotides of a nucleic acid sequence as depicted in FIG. 1. A nucleic acid sequence according to the invention preferably comprises a sequence which has at least 75%, more preferably at least 80%, more preferably at least 85%, more preferably at least 90%, most preferably at least 95% sequence identity to at least 15 nucleotides of a nucleic acid sequence as depicted in FIG. 1. Preferably, said nucleic acid sequence as depicted in FIG. 1 comprises at least one CDR encoding sequence.

One preferred embodiment provides an isolated, synthetic or recombinant nucleic acid sequence with a length of at least 15 nucleotides, or a functional equivalent thereof, encoding at least one CDR sequence of an antibody or immunoglobulin chain according to the invention. Said nucleic acid sequence preferably encodes at least one CDR sequence which has at least 70% sequence identity to a CDR region of antibody F1. Nucleic acid sequences encoding F1 CDR regions are depicted in FIG. 1. Further provided is therefore an isolated, synthetic or recombinant nucleic acid sequence, or a functional equivalent thereof, comprising a sequence which has at least 70% sequence identity to a sequence selected from the group consisting of cgctttgccatgagc (SEQ ID NO:12), tcgatcaataatgggaataacccatactacgcacggtcggtacaatac (SEQ ID NO:13), gatcaccctagtagtggctggcccacctttgactcc (SEQ ID NO:14), cggccagtgaaaacgttggtgactggttggcc (SEQ ID NO:15), aagacatctattctagaaagt (SEQ ID NO:16) and caaactatatacgtttcccgtacact (SEQ ID NO:17).

Said nucleic acid sequence or functional equivalent preferably comprises a sequence which has at least 75%, more preferably at least 80%, more preferably at least 85%, more preferably at least 90% sequence identity to any of the above mentioned sequences. Further provided is a nucleic acid sequence or functional equivalent thereof comprising a sequence which has at least 70% sequence identity to at least part of a nucleotide sequence as depicted in FIG. 1, said part having at least 15 nucleotides and encoding at least one CDR region.

A nucleic acid sequence or functional equivalent thereof according to the present invention preferably encodes a region which has at least 70% sequence identity to an F1 CDR region, an F1 heavy chain and/or an F1 light chain. One embodiment thus provides an isolated, synthetic or recombinant nucleic acid sequence, or a functional equivalent thereof, comprising a sequence encoding an amino acid sequence which has at least 70% sequence identity to the sequence RFAMS (SEQ ID NO:1), and/or at least 70% sequence identity to the sequence SINNGNNPYYARSVQY (SEQ ID NO:2), and/or at least 70% sequence identity to the sequence DHPSSGWPTFDS (SEQ ID NO:3), and/or at least 70% sequence identity to the sequence RASENVGDWLA (SEQ ID NO:4), and/or at least 70% sequence identity to the sequence KTSILES (SEQ ID NO:5), and/or at least 70% sequence identity to the sequence QHYXRFPYT, wherein X is I or M (SEQ ID NO:6), and/or at least 70% sequence identity to the sequence EVQLLESGGGLVQPGGSLRLSCAASGFTLSRFAMSWVRQAPGRGLEWVASINNGNNPYYARSVQYRFTVSRDVSQNTVSLQMNNLRAEDSATYFCAKDHPSSGWPTFDSWGPGTLVTVSS (SEQ ID NO:7), and/or at least 70% sequence identity to the sequence DIQLTQSPSALPASVGDRVSITCRASENVGDWLAWYRQKPGKAPNLLIYKTSILESGVPSRFSGSGSGTEFTLTISSLQPDDFATYYCQHYXRFPYTFGQGTKLEIKRTV, wherein X is I or M (SEQ ID NO:8). Also provided are nucleic acid sequences or functional equivalents thereof encoding variants of the F1 antibody according to the invention. Provided by the invention are, for example, nucleic acid sequences encoding a heavy chain sequence comprising the sequence EVQLVESGGGLVQPGGSLRLSCAASGFTLSRFAMSWVRQAPGRGLEWVASINNGNNPYYARSVQYRFTVSRDVSQNTVSLQMNNLRAEDSATYFCAKDHPSSGWPTFDSWGPGTLVTVSS (SEQ ID NO:9), and/or the sequence EVQLLESGGGLVQPGGSLRLSCAASGFTLSRFAMSWVRQAPGRGLEWVASINNGNNPYYARSVQYRFTVSRDVSQNTVSLQMNNLRAEDSATYFCAKDHPSSGWPTFDSWGPGTLVTVSS (SEQ ID NO:7), and encoding a light chain sequence comprising the sequence DIQLTQSPSALPASVGDRVSITCRASENVGDWLAWYRQKPGKAPNLLIYKTSILESGVPSRFSGSGSGTEFTLTISSLQPDDFATYYCQHYXRFPYTFGQGTKLEIKRA, wherein X is I of M (SEQ ID NO:10), and/or the sequence DIQLTQSPSALPASVGDRVSITCRASENVGDWLAWYRQKPGKAPNLLIYKTSILESGVPSRFSGSGSGTEFTLTISSLQPDDFATYYCQHYXRFPYTFGQGTKVEIKRTV, wherein X is I of M (SEQ ID NO:11), and/or the sequence DIQLTQSPSALPASVGDRVSITCRASENVGDWLAWYRQKPGKAPNLLIYKTSILESGVPSRFSGSGSGTEFTLTISSLQPDDFATYYCQHYXRFPYTFGQGTKLEIKRTV, wherein X is I of M (SEQ ID NO:8).

In one embodiment an asparagine at position 53 of the heavy chain (numbering according to Kabat, 1991) is replaced by another amino acid other than glutamine, in order to prevent deamidation of the asparagine at said position. Preferably said asparagine is replaced by a serine.

The term "% sequence identity" is defined herein as the percentage of residues in a candidate amino acid of nucleic acid sequence that is identical with the residues in a reference sequence after aligning the two sequences and introducing gaps, if necessary, to achieve the maximum percent identity. Methods and computer programs for the alignment are well known in the art.

As used herein, a nucleic acid molecule or nucleic acid sequence of the invention preferably comprises a chain of nucleotides, more preferably DNA and/or RNA. In other embodiments a nucleic acid molecule or nucleic acid sequence of the invention comprises other kinds of nucleic acid structures such as for instance a DNA/RNA helix, peptide nucleic acid (PNA), locked nucleic acid (LNA) and/or a ribozyme. Such other nucleic acid structures are referred to as functional equivalents of a nucleic acid sequence. The term "functional equivalent of a nucleic acid sequence" also encompasses a chain comprising non-natural nucleotides, modified nucleotides and/or non-nucleotide building blocks which exhibit the same function as natural nucleotides.

A nucleic acid sequence according to the present invention is particularly useful for generating binding compounds which are specific for *S. aureus* and/or *S. epidermidis*. This is for instance done by introducing such nucleic acid sequence into a cell so that the cell's nucleic acid translation machinery will produce the encoded binding compound. In one embodiment, genes encoding a heavy and/or light chain according to the invention are expressed in so called producer cells, such as for instance cells of a Chinese hamster ovary (CHO), NSO (a mouse myeloma) or 293(T) cell line, some of which are adapted to commercial antibody production. Proliferation of said producer cells results in a producer cell line capable of producing antibodies or functional parts thereof according to the present invention. Preferably, said producer cell line is suitable for producing compounds for use in humans. Hence, said producer cell line is preferably free of pathogenic agents such as pathogenic micro-organisms. Most preferably, binding compounds consisting of human sequences are generated using a nucleic acid sequence according to the invention.

An isolated or recombinant antibody producing cell capable of producing an antibody or functional part or immunoglobulin chain or functional equivalent according to the invention is therefore also provided, as well as a method for producing an antibody or functional part or immunoglobulin chain or functional equivalent according to the invention, comprising providing a cell with a nucleic acid sequence or functional equivalent according to the invention and allowing said cell to translate said nucleic acid sequence or functional equivalent according to the invention, thereby producing said antibody or functional part or immunoglobulin chain or functional equivalent according to the invention.

An antibody producing cell is defined herein as a cell which is capable of producing and/or secreting an antibody or a functional part thereof, and/or which is capable of developing into a cell which is capable of producing and/or secreting antibody or a functional part thereof. An antibody producing cell according to the invention is preferably a producer cell which is adapted to commercial antibody production. Preferably, said producer cell is suitable for producing compounds for use in humans.

A method according to the invention preferably further comprises a step of harvesting, purifying and/or isolating said antibody or functional part or immunoglobulin chain or functional equivalent according to the invention. The thus obtained binding compounds according to the invention are preferably used in diagnosis of *Staphylococcus* infection, isolation or detection of *Staphylococcus* bacteria, distinguishing between *Staphylococcus* species and other gram-positive bacteria and human therapy, optionally after additional purification, isolation and/or other processing steps.

An antibody or functional part thereof or immunoglobulin chain or functional equivalent thereof according to the present invention is particularly suitable for diagnostic uses. For instance, a sample, such as a tissue or blood sample, can be obtained from an individual or from any other source suspected to be infected with a *Staphylococcus* bacteria, preferably *S. aureus* and/or *S. epidermidis*, more preferably MRSA. Subsequently, said sample can be mixed with an antibody or immunoglobulin chain or functional equivalent or part thereof according to the invention. Said antibody, immunoglobulin chain or functional equivalent or part will specifically bind to *Staphylococcus* bacteria, preferably *S. aureus* and/or *S. epidermidis*. Bacteria bound to an antibody, immunoglobulin chain or functional equivalent or part can be isolated from the sample using any method known in the art, for example, but not limited to, isolation using magnetic beads, streptavidin-coated beads, or isolation through the use of secondary antibodies immobilized on a column. After washing of the bound bacteria and antibody, immunoglobulin chain or functional equivalent or part thereof, bacteria can be eluted from said antibody, immunoglobulin chain or functional equivalent or part by any method known in the art. For instance, binding between bacteria and antibody, immunoglobulin chain or functional equivalent or part can be disrupted by increasing the concentration of salts and/or reducing or increasing pH, and/or by addition of excess epitope.

Isolation of *Staphylococcus* bacteria, preferably *S. aureus* and/or *S. epidermidis*, may be used for various applications. For instance, infection with several different gram-positive bacteria may result in overlapping symptoms in an individual. In such cases, it can be difficult to discriminate between *S. aureus* and/or *S. epidermidis* and other gram-positive bacteria. An antibody, immunoglobulin chain or functional equivalent or part thereof according to the present invention can then be used to detect the presence of *S. aureus* and/or *S. epidermidis*, or for distinguishing between *S. aureus* and/or *S. epidermidis* and other bacteria. Isolation of bacteria from a sample of an individual suspected of suffering from an infection with *S. aureus* and/or *S. epidermidis* or from any other source, such as a bacterial culture, can facilitate detection of said *Staphylococcus* bacteria, because isolation results in an increased concentration and/or a higher purity of said *Staphylococcus* bacteria.

Isolation of *Staphylococcus* species, preferably *S. aureus* and/or *S. epidermidis*, more preferably MRSA, can for instance further be used to identify the specific *S. aureus* and/or *S. epidermidis* strain, preferably the MRSA strain in a sample. Identification of said strain can for instance be performed by determining the sequence of the bacterial DNA. In such case it is preferred to first obtain an isolated *S. aureus* and/or *S. epidermidis*.

In one embodiment of the invention, an antibody, immunoglobulin chain or functional equivalent or part thereof according to the present invention is labeled in order to be able to detect said antibody, immunoglobulin chain, or functional equivalent or part, for instance, but not limited to, fluorescently labeled, or radioactively labeled. Alternatively, an antibody or functional part thereof or immunoglobulin chain or functional equivalent thereof according to the invention is detected using a labeled secondary antibody which is directed against said antibody, immunoglobulin chain or functional equivalent or part thereof according to the invention. If binding of said antibody, immunoglobulin chain or functional equivalent or part thereof is detected, *S. aureus* and/or *S. epidermidis* is present.

Provided by the invention is therefore a use of an antibody or functional part thereof or immunoglobulin chain or functional equivalent thereof according to the invention for diagnosis of a *Staphylococcus* infection, preferably *S. aureus* infection, more preferably MRSA infection, for detecting *S. aureus* and/or *S. epidermidis*, preferably MRSA, and for distinguishing between *S. aureus* and/or *S. epidermidis*, preferably MRSA and other gram-positive bacteria. Also provided is an antibody or functional part thereof or an immunoglobulin chain or functional equivalent thereof according to the invention for use in the diagnosis of a *Staphylococcus* infection, preferably *S. aureus* infection, more preferably MRSA infection.

Further provided is a method for isolating *S. aureus* and/or *S. epidermidis* bacteria from a solution using an antibody or functional part or an immunoglobulin chain or functional equivalent thereof according to the invention. Said method preferably comprises providing a sample of an individual suspected of suffering from an infection with *S. aureus* and/or *S. epidermidis*, preferably MRSA, or from any other source, such as a bacterial culture, adding an antibody or functional part or an immunoglobulin chain or functional equivalent thereof according to the invention to said sample, allowing binding of said antibody or functional part or an immunoglobulin chain or functional equivalent thereof according to the invention to *S. aureus* and/or *S. epidermidis* bacteria, when present, and isolating *S. aureus* and/or *S. epidermidis* bacteria bound to an antibody or functional part or an immunoglobulin chain or functional equivalent thereof according to the invention from said sample.

Now that Gram-positive bacteria-specific binding compounds according to the invention and nucleic acid sequences coding therefore have been provided, including human binding compounds, improved therapeutic applications have become available. Gram-positive bacteria such as *S. aureus* and/or *S. epidermidis* are counteracted by binding compounds according to the invention. A binding compound according to the invention is therefore particularly suitable for use as a medicine or prophylactic agent. Preferably, binding compounds are used which consist of human sequences, or which have at most 5% of non-human sequences, in order to reduce the chance of adverse side effects when human individuals are treated. An antibody or functional part or an immunoglobulin chain or functional equivalent thereof or a nucleic acid sequence or functional equivalent thereof according to the invention for use as a medicament and/or prophylactic agent is therefore also herewith provided. When a nucleic acid or functional equivalent according to the invention is administered, it will be translated in situ into a binding compound according to the invention. In a particularly preferred embodiment said antibody comprises antibody F1, or a functional part thereof. Said medicament or prophylactic agent is preferably used for counteracting or at least in part preventing an infection by *S. aureus* and/or *S. epidermidis* or for counteracting or at least in part preventing adverse effects of an infection by *S. aureus* and/or *S. epidermidis*. Further provided is therefore an antibody or functional part or an immunoglobulin chain or functional equivalent thereof or a nucleic acid sequence or functional equivalent thereof according to the invention for use as a medicament and/or prophylactic agent for at least in part treating and/or preventing a condition related to *S. aureus* and/or *S. epidermidis*. Non-limiting examples of such conditions are skin infections, pimples, impetigo, boils, cellulitis folliculitis, furuncles, carbuncles, scalded skin syndrome, abscesses, pneumonia, meningitis, osteomyelitis, endocarditis, toxic shock syndrome and septicemia. Preferably, *S. aureus* infection is counteracted or at least in part prevented. Most preferably, an MRSA-related condition is counteracted, diminished and/or at least in part prevented. A use of an antibody or functional part or an immunoglobulin chain or functional equivalent thereof or a nucleic acid sequence or functional equivalent thereof according to the invention for the preparation of a medicament and/or prophylactic agent for at least in part treating and/or preventing *S. aureus* and/or *S. epidermidis* is therefore also provided, as well as a method for at least in part treating or preventing a condition related to *S. aureus* and/or *S. epidermidis*, the method comprising administering to an individual in need thereof a therapeutically effective amount of an antibody or functional part or an immunoglobulin chain or functional equivalent according to the invention, preferably after said individual has been diagnosed to be infected by *S. aureus* and/or *S. epidermidis*. Said condition preferably comprises at least one of the *S. aureus*-related conditions listed above, most preferably an MRSA-related condition.

Said antibody preferably comprises antibody F1, or a functional part thereof.

In order to counteract Gram-positive bacteria, a binding compound according to the invention is preferably administered to an individual before an infection has taken place. Alternatively, a binding compound according to the invention is administered when an individual is already infected. Said binding compound is preferably administered to individuals with an increased risk of complications, such as for instance hospitalized individuals and/or individuals with compromised immunity. Also elderly people have an increased risk of bacterial conditions. Binding compounds according to the invention are preferably administered via one or more injections. Dose ranges of binding compounds according to the invention to be used in the therapeutic applications as described herein before are designed on the basis of rising dose studies in the clinic in clinical trials for which rigorous protocol requirements exist. Typical doses are between 0.1 and 10 mg per kg body weight. For therapeutic application binding compounds according to the invention are typically combined with a pharmaceutically acceptable carrier, diluent and/or excipient. Examples of suitable carriers for instance comprise keyhole limpet haemocyanin (KLH), serum albumin (e.g. BSA or RSA) and ovalbumin. In one preferred embodiment said suitable carrier comprises a solution like for example saline.

In yet another embodiment a nucleic acid encoding a binding compound according to the invention is used. As already described, upon administration of such nucleic acid, binding compounds are produced by the host's machinery. Produced binding compounds are capable of preventing and/or counteracting Gram-positive bacterial infection and/or the adverse effects of such infection. A nucleic acid sequence or functional equivalent according to the invention for use as a medicament and/or prophylactic agent is therefore also herewith provided. Said nucleic acid is preferably used for counteracting *S. aureus* and/or *S. epidermidis*, more preferably *S. aureus*, most preferably MRSA. Further provided is therefore a use of a nucleic acid sequence or functional equivalent according to the invention for the preparation of a medicament and/or prophylactic agent for at least in part treating and/or preventing a Gram-positive bacterium-related condition. Said Gram-positive bacterium-related condition preferably comprises an infection by *S. aureus* or *S. epidermidis*, more preferably an *S. aureus* infection, most preferably an MRSA infection.

Further provided is a pharmaceutical composition comprising an antibody or functional part or an immunoglobulin chain or functional equivalent thereof or a nucleic acid sequence or functional equivalent thereof according to the invention and a pharmaceutical acceptable carrier, diluent or excipient. Said pharmaceutical composition is preferably suitable for human use.

The invention is further explained in the following examples. These examples do not limit the scope of the invention, but merely serve to clarify the invention.

All patent documents and other publications that are referred to in the detailed description are incorporated herein by reference in their entirety.

EXAMPLES

Example 1

Methods
B Cell Isolation

B-cells were obtained from fresh blood of adults by Ficoll separation and CD4/CD8 negative selection with MACS microbeads as described by the manufacturer (Miltenyi Biotech). To obtain memory B cells, cells were sorted for $CD19^+CD3^-CD27^+IgD^-IgA^-$ on a FACSaria (Becton Dickinson). The use of these tissues was approved by the medical ethical committees of the institution and was contingent on informed consent. Donors were selected based on carrying hospital acquired MRSA strains with genotype cluster 109 and 16.

Cell Culture

B-cells maintained in standard culture medium containing IMDM (Gibco), 8% FBS (HyClone) and penicillin/streptomycin (Roche) were co-cultured on γ-irradiated (50Gy) mouse L cell fibroblasts stably expressing CD40L (CD40L-L cells, $10^5$ cells/ml) and recombinant mouse IL-21 (25 ng/ml, R&D systems). rhIL-4 (R&D) was used at 50 ng/ml. Cells were routinely tested by PCR and were found negative for the presence of mycoplasma and EBV (data not shown).

Bulk transduced human memory B cells double positive for NGFR and GFP were purified by FACS cell sorting and cultured in 96 well plates at a cell density of 500 cell per well. Culture supernatants were tested in ELISAs using bacterial lysates of the Newman and SH1000 strains. Positive cultures were subcloned at 10 cell/well cell density in 96 well plates and again tested by ELISA. Subsequently positive cultures were seeded at 1 cell per well and tested again by ELISA for reactivity against S. aureus strains Newman and SH1000.

Retroviral Transduction

The BCL6 retroviral construct has been described before (Shvarts A. et al. Genes Dev 16, 681-686 (2002)). cDNA encoding human Bcl-xL was kindly provided by Dr. Stanley Korsmeyer. BCL6 and Bcl-xL were separately cloned into a BCL6-NGFR and a BclxL-GFP construct. These constructs were transfected into the LZRS retroviral packaging cells, phoenix as described before (Jaleco A. C. et al. Blood 94, 2637-2646 (1999); Scheeren F. A. et al. Nat Immunol 6, 303-313 (2005)). Memory B-cells were double transduced by the BCL6 and Bcl-xL containing retroviruses after activation on CD40L-L cells in the presence of rmIL-21 for 36 hrs as described before (Diehl S. A. et al. J Immunol 180, 4805-4815 (2008); Kwakkenbos M. et al. Nat Med in press (2009)). Transduced cells were maintained on CD40L-L cells with rmIL-21.

Elisa

To determine antibody content ELISA plates were coated with anti-human IgG (Jackson ImmunoResearch Laboratories) at 5 μg/ml in PBS for 1 hr at 37° C. or o/n at 4° C. and washed in ELISA wash buffer (PBS, 0.5% Tween-20). 4% milk in PBS was used as blocking agent, before serial dilution of cell culture supernatants and an enzyme-conjugated detection antibody was added (dilution 1:2500 for HRP-conjugated anti-IgG (Jackson)). TMB substrate/stop solution (Biosource) was used for development of the ELISAs.

For screening purposes we used lysates from the Newman and SH1000 strains. Both were made in PBS and directly coated at 5 to 10 μg ml$^{-1}$ before B cell culture supernatants were tested un- or 1:2 diluted.

To explore the antigen specificity of the human IgG1 clone F1, an LTA detection ELISA was developed. Purified LTA preparations from S. aureus, B. subtilis, S. faecalis and S. pyogenes (Sigma) was added to ELISA plates coated with polyclonal IgG purified mouse anti-LTA (1/200 stock 1 mg ml$^{-1}$, QED Bioscience), before secondary antibodies were added.

In addition, we tested several LTA preparations derived from a library developed by W. Fischer (Institut fur Biochemie, Univ of Erlangen, Germany) and kindly provided by B. Appelmelk (VU, Amsterdam, Netherlands) (see for more details (Keller R. et al. Infect Immun 60, 3664-3672 (1992), Polotsky V. Y. et al. Infection and Immunity 64, 380-383 (1996) and Greenberg J. W. et al. Infection and Immunity 64, 3318-3325 (1996)) and reviewed in (Weidenmaier C. et al. Nat Rev Microbiol 6, 276-287 (2008))) in direct ELISA's. LTA preparations were coated at 1 μg ml$^{-1}$ before rF1 (10 μg ml$^{-1}$) or control antibodies (1:5 dilution of hybridoma supernatant) were added and further detected with conjugated anti-human or mouse antibodies. The panel of purified LTA preparations included: B. subtilis, S. aureus, L. lactis, L. garvieae, B. bifidum, M. luteus, L. casei, L. mesenteroides, B. licheniformis, L. welshimeri, E. hirae, L. raffinolactis, S. mutans, S. pneumoniae. Several variants contain or lack alanine residues and/or lipid anchors (not depicted here).

Binding of the F1 Antibody to Bacterial Cultures

The Newman S. aureus and the S. pneumoniae strain (serotype 3) were used. Newman was cultured in TSH 50 ml O/N, then 1 ml was resuspendend in 100 ml for 2 to 2.5 hrs till OD:1 and bacteria were collected. S. pneumoniae was cultured in Todd Hewitt medium mixed with yeast medium. Before, bacteria were incubated with F1 antibody, a control IgG (D25, a human anti-RSV antibody) or only with the secondary antibody (IgG-PE only), cells were pretreated with 100% total mouse serum to prevent background staining. After washing the secondary antibody was added (IgG-PE). Antibody incubations were performed for 20 min on ice.

F1 Sequence Determination and Expression Cloning

We isolated total RNA using Trizol (Invitrogen), generated cDNA by using superscript RT, performed PCR and cloned the heavy and light chain variable regions into the pCR2.1 TA cloning vector (Invitrogen). To rule out reverse transcriptase or DNA polymerase induced mutations, we performed several independent cloning experiments. To produce recombinant F1 mAb we cloned F1 heavy and light variable regions in frame with human IgG1 and Kappa constant regions into a pcDNA3.1 (Invitrogen) based vector and transiently transfected 293T cells. We purified recombinant F1 from the culture supernatant with Protein A.

Results

Generation of the F1 Clone

From three subjects who were tested positive for MRSA but were not sick, 50-60 ml of heparin blood was collected and peripheral B-cells were isolated after a ficoll purification step. B-cells from several B-cell populations were double transduced with retroviruses containing BCL6-NGFR and Bcl-xL-GFP (Diehl et al and Kwakkenbos et al). From the IgG, CD27 positive population, polyclonal mini-cultures B-cell cultures were started in 96 wells plate with a cell density of 500 cells/well. Supernatant of these mini-cultures was collected and used in ELISAs to screen for the presence of *S. aureus*-specific IgG antibodies (in these ELISAs the coating was cell lysates of two *S. aureus* strains, SH1000 and Newman). Mini-cultures that were screened positive in both the SH1000 as well as the Newman *S. aureus* were seeded in new mini-cultures at a density of 10 cells/well. Again, supernatant of these mini-cultures was collected and screened in the SH1000 and Newman ELISAs. Clones that were screened positive in both ELISAs were seeded into monoclonal cultures (i.e. 1 cell/well). After testing the supernatant of these monoclonal cultures, one clone (named F1) was found to produce *S. aureus* specific monoclonal IgG antibodies.

Antibodies in the Supernatant of the F1 Clone Bind to LTA Preparations from *S. aureus*

Generating the F1 clone, we already found that supernatant of F1 bound to the bacterial cell lysates of two *S. aureus* strains, SH1000 and Newman. The major cell wall compound of Gram-positive bacteria is LTA, and therefore we decided to test binding of F1 supernatant to *S. aureus* LTA preparations in an ELISA. As shown in Table 1, supernatant of the F1 clone binds to bacterial cell lysates of the SH1000 and Newman *S. aureus* strain but also to commercially purchased purified *S. aureus* LTA preparations. We noted, however, that the binding to the LTA preparations was significantly lower than that observed with whole bacteria.

TABLE 1

Supernatant of the F1 clone binds to *S. aureus* LTA preparations.

|  | F1 clone | mouse anti-LTA | anti-flu control |
|---|---|---|---|
| SH1000 | 1.004 | −0.010 | −0.007 |
| Newman | 0.753 | −0.007 | 0.007 |
| SA LTA (sigma) | 0.176 | −0.005 | −0.009 |
| Flu H3 | 0.003 | −0.002 | 1.523 |
| No coat | −0.013 | −0.014 | −0.015 |

As a negative control an anti-mouse-HRP conjugated secondary antibody was used. Another control was an anti-influenza virus antibody that only detected influenza H3 protein.

Figure 2B:
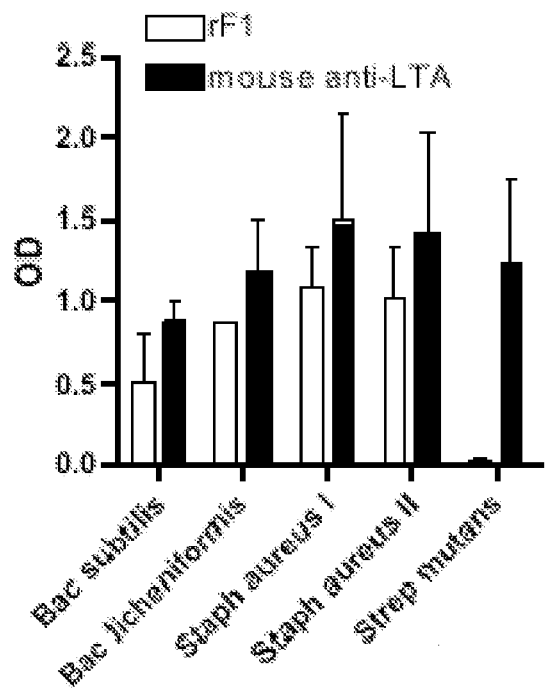

The Recombinant Produced F1 Antibody Binds to LTA Preparations from Multiple Sources After cloning the antibody genes into expression vectors and producing recombinant F1 (rF1) antibody in an expression system, the rF1 antibody was tested on purified LTA preparations from several bacteria. As shown in FIG. 2A, the rF1 antibody binds well to commercial LTA samples obtained from *S. aureus* and *B. subtilis*, and a bit less profoundly to LTA samples from *S. faecalis* and *S. pyogenes*. The rF1 antibody did not bind to an LTA sample from *S. pneumoniae* (data not shown). In addition rF1 recognized highly purified LTA samples from *B. subtilis, B. licheniformis* and two isolates of *S. aureus* (FIG. 2b). rF1 did not bind to LTA preparations from *S. mutans* (FIG. 2b) or from *L. lactis, L. garvieae, B. bifidum, M. luteus, L. casei, L. mesenteroides, L. welshimeri, E. hirae, L. raffinolactis, S. mutans* and *S. pneumoniae* (results not shown).

Recombinant F1 Antibody Binds to Living *S. aureus* Bacteria

Figure 3A:
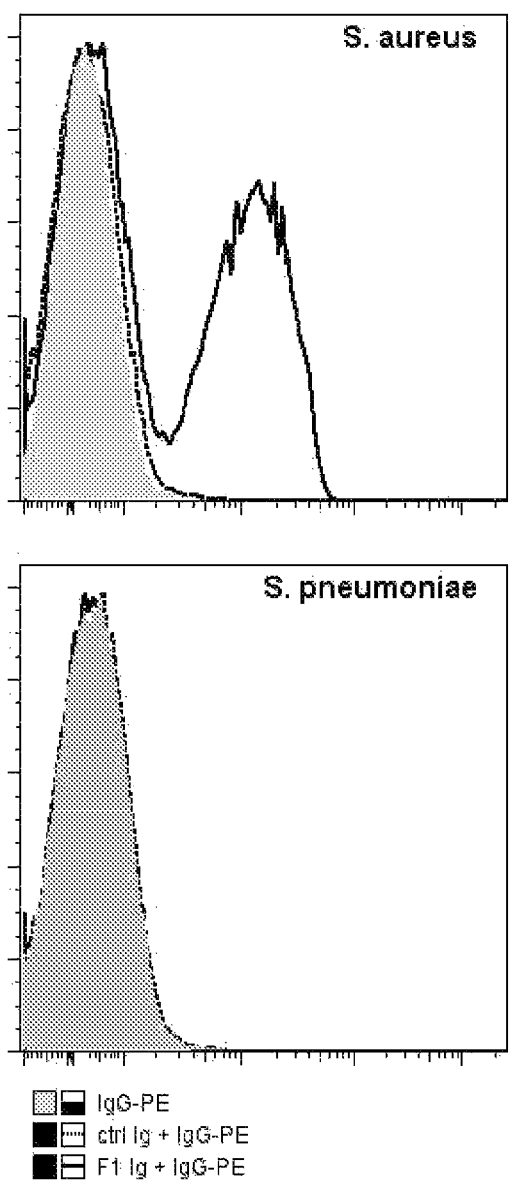
FIG. 3: Recombinant F1 antibody binds to *S. aureus* but not to *S. pneumoniae*. (a) Bacteria were incubated with F1 antibody, or a control IgG (D25, a human anti-RSV antibody) or without first antibody (IgG-PE only). After washing the secondary antibody was added (IgG-PE). (b) 6 clinical isolates were tested in two separate experiments for the binding of F1. Tested were a PVL+ strain (SA-1), 3 regular (SA-2 SA-3 and SA-4), and 2 MRSA strains (SA-5 and SA-6).
Figure 3B:
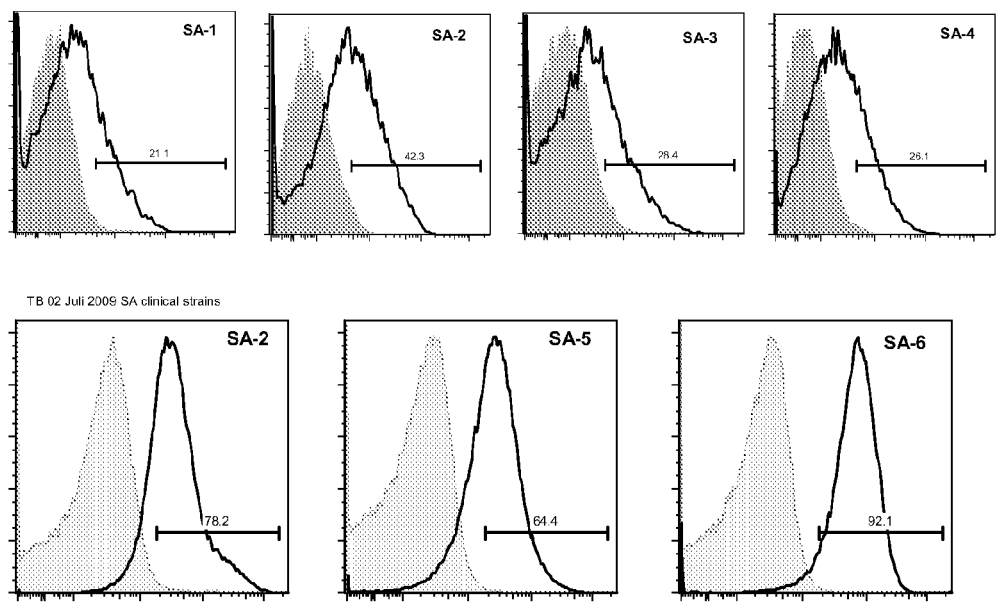

In order to study whether the rF1 antibody would also recognize living Gram-positive bacteria, binding of the rF1 antibody to *S. aureus* and *S. pneumoniae* was tested by using flow cytometry. As shown in FIG. 3A, the rF1 antibody binds to living *S. aureus* bacteria (Newman strain), but not to *S. pneumoniae*. In addition we show that rF1 recognized 6 clinical *S. aureus* isolates; one is a pathogenic strain which is PVL positive, 3 regular strains and 2 MRSA strain (FIG. 3b).

Example 2

Methods
Bacterial Strains and Culture.

Methicillin-resistant *S. aureus* (MRSA) strains USA300 (1114), USA400, N315, USA100, USA1000, COL, MRSA252, as well as methicillin-sensitive *S. aureus* (MSSA) strains Reynolds, Becker, Smith Diffuse, MN8, and vancomycin intermediate sensitive (VISA) strain Mu50, were all obtained from the Network on Antibiotic Resistance in *Staphylococcus aureus* (NARSA); MSSA strains Newman and Rosenbach were from ATCC. *Staphylococcus epidermidis, Bacillus subtilis, Enterococcus faecalis*, and *Streptococcus pyogenes* were obtained from Ward's Natural Science; *Listeria monocytogenes* was from ATCC. Bacteria were grown on tryptic soy agar (TSA) plates supplemented with 5% sheep blood for 18 h at 37° C. For liquid cultures, single colonies from TSA plates were inoculated into tryptic soy broth (TSB) and incubated at 37° C. while shaking at 200 rpm for 18 h. Fresh 100-fold dilutions of these cultures in fresh TSB were further subcultured for various times.

FACS Analysis of rF1 Binding to Whole Bacteria Grown in vitro.

For antibody staining of whole cells, bacteria were harvested from TSA plates or TSB cultures, and washed with Hank's Buffered Salt Solution (HBSS) without phenol red supplemented with 0.1% BSA (IgG free; Sigma) and 10 mM Hepes, pH 7.4 (HB buffer), by centrifugation at 1700×g for 20 min. Bacterial concentrations were estimated by reading optical density at 630 nm. Bacterial suspensions of 20×10$^8$ CFU/mL in HB buffer were mixed with equal volumes of 300 µg/mL of rabbit IgG (Sigma), and incubated for 1 h at room temperature (RT) to block nonspecific IgG binding. Primary antibodies, including rF1 and a human IgG1 isotype control, were added to a final concentration of 2 µg/mL, and these mixtures were incubated for 15 min at RT. After two washes with HB, bacterial pellets were resuspended in a solution of fluorescent anti-human IgG secondary antibodies (Jackson Immunoresearch) and incubated for 15 min at RT. The bacteria were washed twice with PBS, resuspended in PBS with 1% paraformaldehyde, and analyzed by flow cytometry.

FACS Analysis of rF1 Binding to Whole Bacteria from Infected Tissues.

For analysis of antibody binding to bacteria from infected tissue, 4 h subcultures of USA300 in TSB were washed with PBS. Mice were injected intravenously with a 100 µL of a suspension of USA300 in PBS with an estimated concentration of 10×10$^8$ CFU/mL. Three days later, kidneys, livers, and lungs were harvested and homogenized using conical tissue grinder tubes (VWR). When indicated, organs were harvested at different time points of infection. To lyse mouse cells, the homogenates were incubated for 10 min at RT in PBS containing 0.1% Triton-X100 (Thermo), 10 µg/mL of DNAseI (Roche) and Complete Mini protease inhibitor cocktail (Roche), and passed through a 40 µm filter (Falcon). The cell suspensions were washed twice with PBS and resuspended in HB buffer, mixed with equal volumes of 600 µg/mL of human IgG (Sigma), and incubated for 1 h at RT. Primary Abs, including rF1 and a human IgG1 isotype control, were added to a final concentration of 2 µg/mL. To differentiate bacteria from mouse organ debris, rabbit IgG anti-*S. aureus* (Abcam) was added to a concentration of 20 µg/mL. After incubation for 15 min at RT, cells were washed twice with HB buffer, and resuspended in a mixture of anti-human IgG and anti-rabbit IgG secondary antibodies, each labeled with a different fluorochrome (Jackson Immunoresearch). After two washes with PBS, cells were resuspended in PBS with 2% paraformaldehyde and analyzed by flow cytometry. After selecting bacteria from double fluorescence plots by gating for positive staining with rabbit IgG anti-S. aureus, overlay histogram plots of fluorescence intensities of rF1 and isotype control were generated.

Results rF1 Binds Strongly to 14 S. aureus Strains and S. epidermidis

Figure 4A:
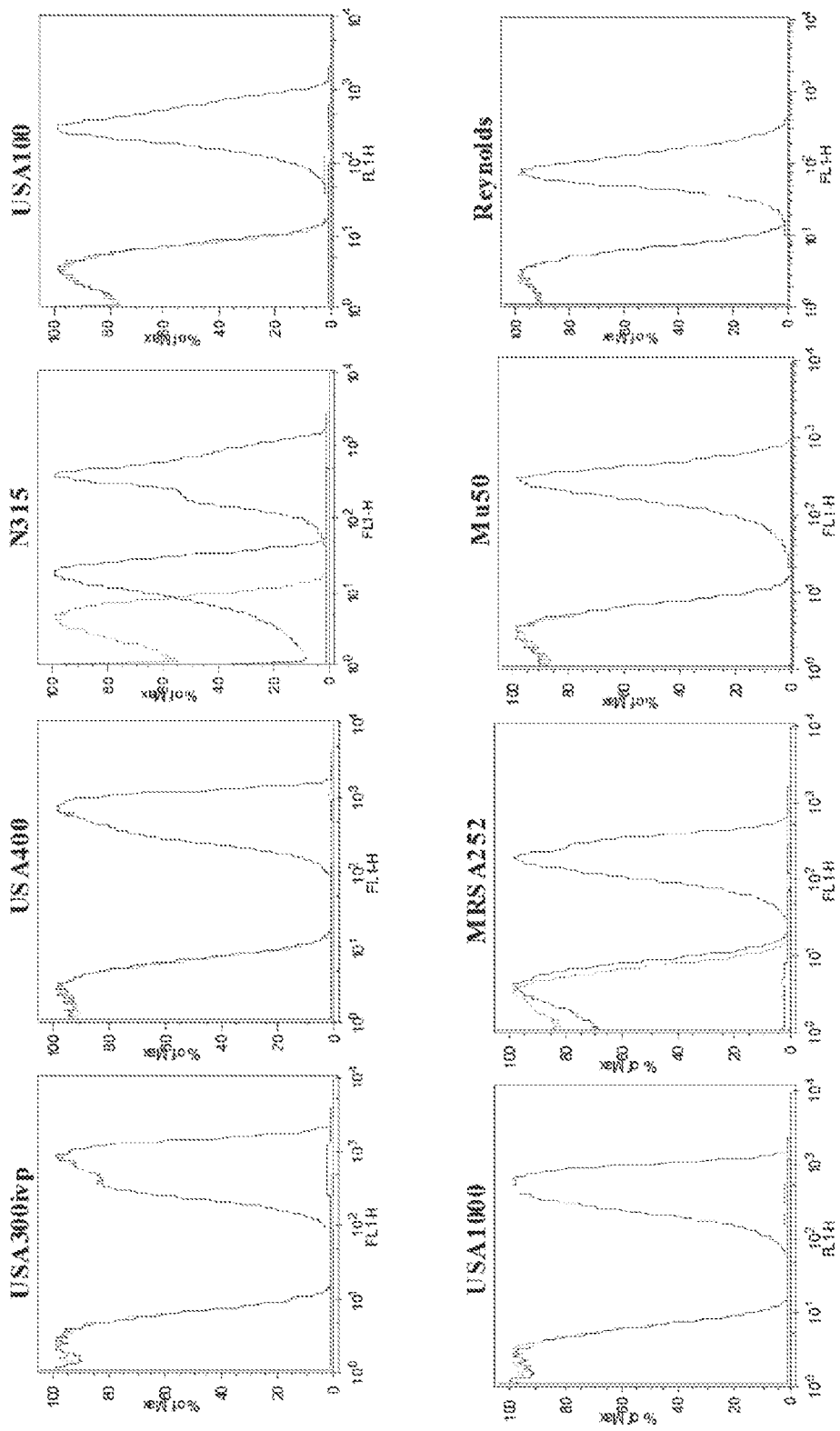
FIG. 4: (a) Binding of rF1 antibody to 14 *S. aureus* strains. (b) rF1 antibody binds to *S. epidermidis* but not to *Bacillus subtilis, Enterococcus faecalis, Listeria monocytogenes* and *Streptococcus pyogenes*.
Figure 4A:
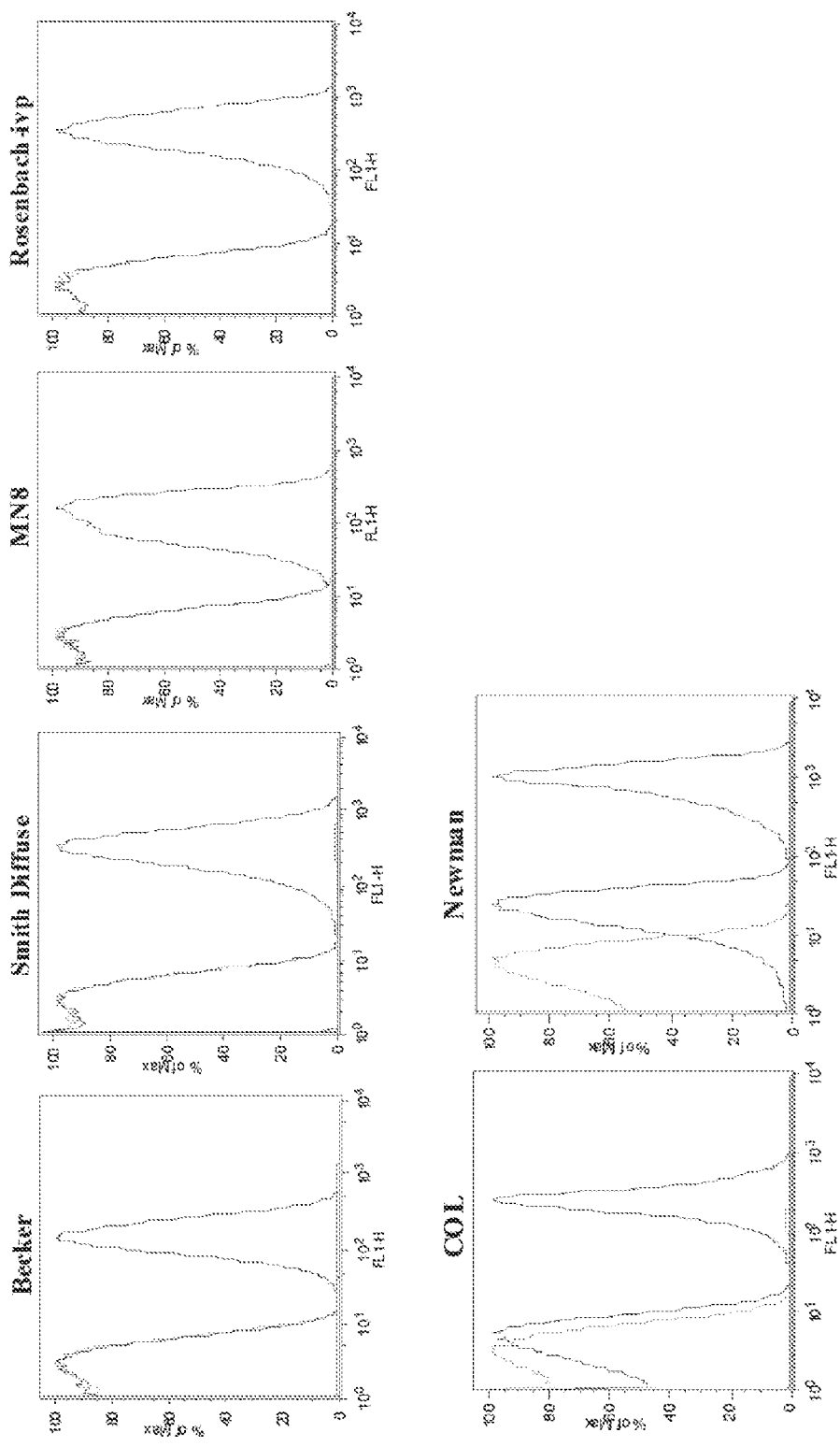
Figure 4B:
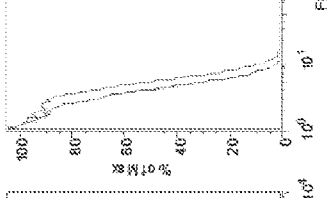
Figure 4B:
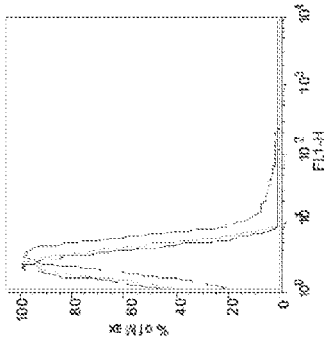
Figure 4B:
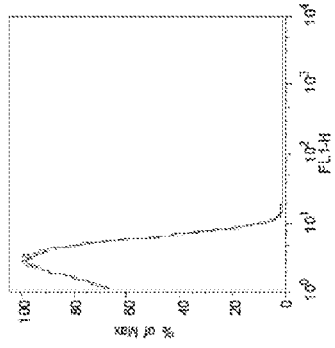
Figure 4B:
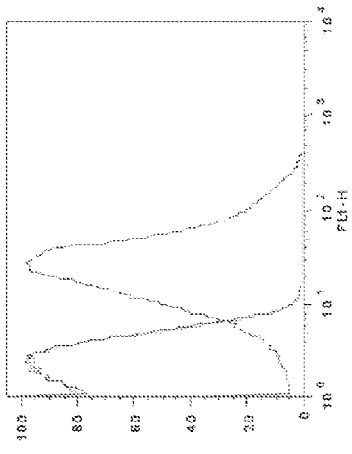

Seven Methicillin-resistant S. aureus (MRSA) strains, six methicillin-sensitive S. aureus (MSSA) strains, one vancomycin intermediate sensitive S. aureus (VISA) strain, S. epidermidis and several other gram-positive species were tested for binding to rF1 antibody. As shown in FIG. 4, rF1 strongly binds to all 14 S. aureus strains (FIG. 4A) and to S. epidermidis (FIG. 4B), but not to the other tested gram-positive species (FIG. 4B).

rF1 Binds to MRSA from Different Growth Stages and from in vivo Infection

We tested the ability of mAb rF1 to bind to bacteria both in different tissues and over the course of infection. We found that rF1 bound to bacteria isolated from murine kidney, liver and lung tissue two days after infection and that the binding to bacteria isolated from infected kidneys was stable, binding bacteria 2, 3 and 8 days after infection.

Figure 5:
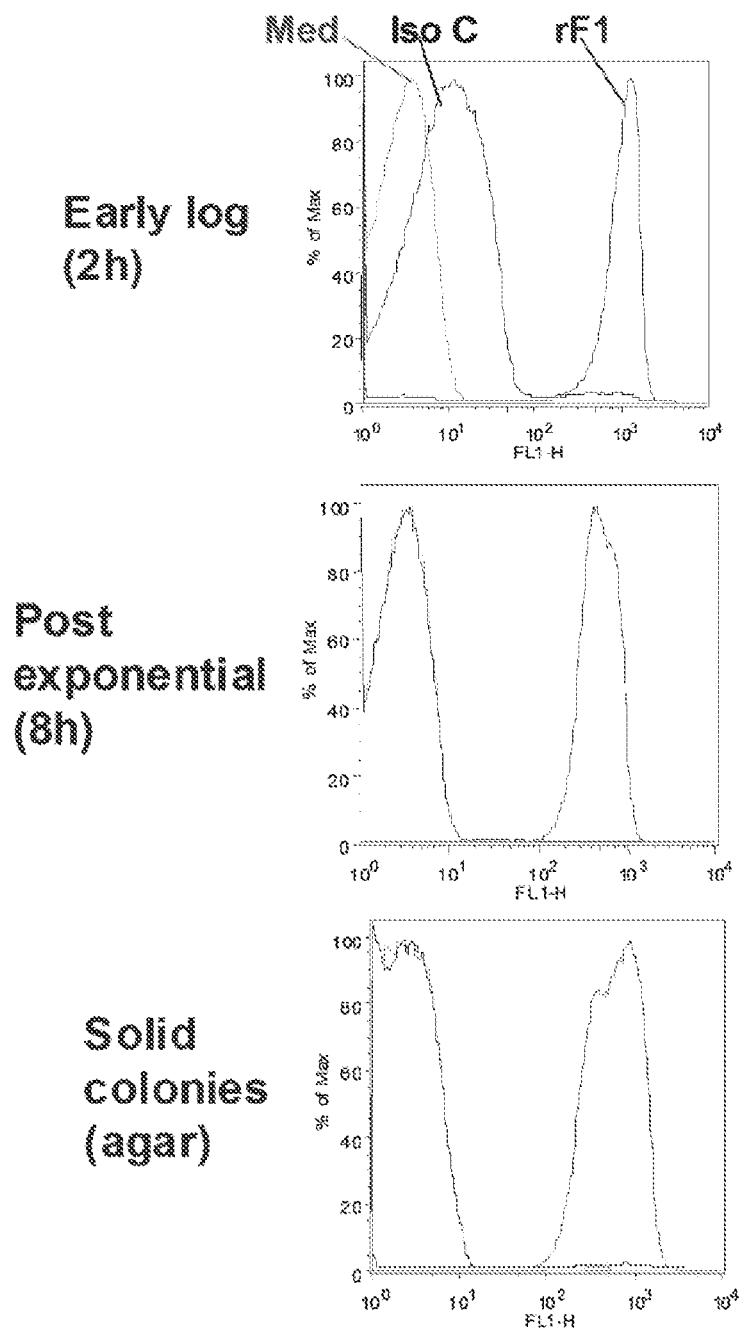
FIG. 5: (a) rF1 antibody binds to MRSA in different growth stages, Iso C: isotype control, Med: media control (b) rF1 antibody binds to MRSA isolated from infected tissue.
Figure 5:
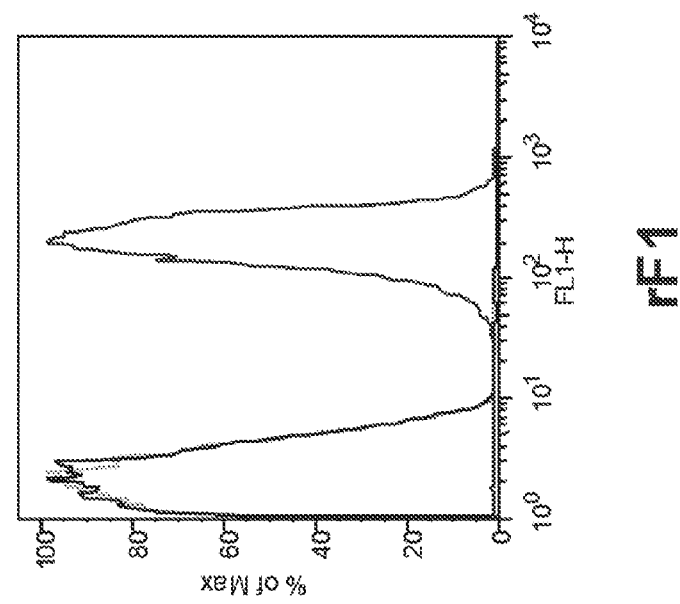

Binding of rF1 antibody to different growth stages of MRSA (strain USA300), namely early logarithmical growth (2 hours) and post exponential growth (8 hours) in TSB cultures, and growth of solid colonies on TSA plates was tested. rF1 strongly binds to all growth stages tested (FIG. 5A).

Binding of rF1 antibody to MRSA (strain USA300) to whole bacteria from infected tissue was tested in homogenized kidneys from mice three day after the mice were systemically infected with MRSA. As shown in FIG. 5B rF1 binds to MRSA obtained from infected tissue.

Example 3

Further experiments were performed to identify the epitope bound by antibody rF1. Although binding to LTA preparations had been observed (see, e.g., Example 1), that binding was not as robust as binding to whole bacteria suggesting that another epitope may be involved in rF1 binding.

Methods

Immunoprecipitation, Western Blotting and Mass Spectrometry of Cell Wall Lysates of S. aureus and S. epidermidis and Commercial WTA Cell Wall Preparation 40 micrograms of a commercial wall teichoic acid (WTA) preparation from Wood46 S. aureus strain (Biodesign/Meridian Life Sciences, Maine) was split into two parts and immunoprecipitated with 1 ug/ml of rF1 or isotype control human antibody. Antibodies were captured with Protein A/G Ultralink Resin (Pierce). The samples were then treated with 50 mM dithiothreitol, 10 mM 2-Iodoacetamide and run on an 8% Tris-glycine gel and subsequently Western blotted with rF1.

A cell wall preparation of a 20 ml overnight culture of USA300 S. aureus strain was prepared by treatment of the culture (40 mg cell pellet/ml) with 100 mg/ml of lysostaphin in 30% raffinose buffer at 37° C. for 30 minutes. The entire cell wall prep was filtered, diluted up to 10 ml with NP40 Lysis buffer and incubated twice with anti-Flag M2 Agarose (Sigma) to deplete as much protein-A from the cell wall prep as possible. Final cell wall preparation was split into two parts and immunoprecipitated with 1 ug/ml of rF1 or isotype control human antibody. Antibodies were captured with Protein A/G Ultralink Resin (Pierce). The samples were then treated with 50 mM dithiothreitol, 10 mM 2-Iodoacetamide and run on an 8% Tris-glycine gel and subsequently silver stained or Western blotted with rF1.

Lysates from a 20 ml overnight culture of Staphylococcus epidermidis was prepared by bead beating in NP40 Lysis Buffer. The resulting lysate preparation was diluted to 10 ml with NP40 Lysis Buffer, split into two parts and immunoprecipitated with 1 ug/ml of rF1 or control antibody. Antibodies were captured with Protein A/G Ultralink Resin (Pierce). The samples were then treated with 50 mM dithiothreitol, 10 mM 2-Iodoacetamide and run on an 8% Tris-glycine gel and subsequently silver stained or Western blotted with rF1.

For proteomic analysis, samples were applied to a precast SDS PAGE mini gel and the resolved proteins stained with Coomassie Blue. Gel slices from the region of the gel corresponding to bands visualized by rF1 western blot were excised and reduced, alkylated with iodoacetamide, and digested in situ with trypsin. Resulting tryptic peptides were analyzed by microcapillary reverse-phase liquid chromatography- nano electrospray tandem mass spectrometry on a hybrid linear ion trap Fourier transform ion cyclotron resonance mass spectrometer (LTQ-FT; Thermo Fisher) in a data-dependent experiment. Tandem mass spectral results were submitted for database searching using Mascot software (Matrix Science).

Expression of Exogenous ClfA Expressed in S. aureus and E. coli

S. aureus expression of His-tagged ClfA: The Clumping factor-A (ClfA) gene was PCR amplified from the sequence encoding the signal sequence to the sequence encoding the glycine in the LPXTG motif from USA300 genomic DNA. A c-terminal His Tag was engineered at the end of the LPXTG motif and ligated into the pTet S. aureus expression vector (pSAS10 from Genentech). The resulting construct was then electroporated into S. aureus WT RN4220. A 20 ml culture of either the electroporated RN4220 or RN4220 empty (not carrying a pTet expression vector) was inoculated from an overnight culture (starting $OD_{600}$ of 0.15), grown for 1 hr in trypticase soy broth (TSB) and then induced protein expression for 2 hrs with anhydrotetracycline (200 ng/ml). At the end of the induction period, the S. aureus culture was pre-lysed with lysostaphin (50 ug/ml) and then further lysed by bead beating in lysis buffer (150 mM NaCl, 20 mM Tris pH 7.5, 1% triton-X, and Roche protease inhibitor EDTA-free tablets). Cleared lysates were then incubated with NiNta resin (Qiagen) in the presence of 10 mM Imidazole for 1 hr at 4° C. to pull-down the recombinant ClfA protein.

E. coli expression of His-tagged Clfa: The Clumping factor-A (ClfA) gene was PCR amplified from the sequence encoding the N-term signal sequence (with the start methionine) to the sequence encoding the glycine in the C-term LPXTG motif from USA300 genomic DNA. The amplified PCR product was then ligated in frame with a c-terminal His tag into the pET 21b(+) E. coli expression vector (Novagen). The resulting construct was transformed into E. coli BL21-gold (DE3) Competent Cells (Stratagene) and induced for protein expression for 3.5 hrs with IPTG according to the manufacturer's instructions. The induced E. coli culture was lysed by bead beating in Lysis Buffer (150 mM NaCl, 20 mM Tris pH 7.5, 1% triton-X, and Roche protease inhibitor EDTA-free tablets). Cleared lysates were then incubated with NiNta resin (Qiagen) in the presence of 10 mM Imidazole for 1 hr at 4° C. to pull-down the recombinant ClfA protein.

Expression of Exogenous ClfA Expressed in *E. coli* and Incubation with *S. aureus* Lysate Expression and Purification of *S. aureus* cell surface SDR proteins ClfA, ClfB, SdrC, SdrD, SdrE in *E.coli*: The ClfA, ClfB, SdrC, SdrD and SdrE genes were PCR amplified from the sequence encoding the mature start of the protein to the sequence encoding the glycine in the LPXTG motif from USA300 genomic DNA and ligated in-frame with an N-terminal Unizyme tag into the ST239 Vector (Genentech). The constructs were transformed into *E. coli* 58F3 (Genentech), induced for protein expression and subsequently purified.

NiNta capture of NT Unizyme tagged SDR proteins: 500 ug of purified N-terminal Unizyme tagged SDR proteins (ClfA, ClfB, SdrC, SdrD, SdrE) were diluted in PBS containing protease inhibitors (EDTA-free) and incubated with NiNta resin (Qiagen) for 1.5 hr at 4° C. NiNta resin with the captured Unizyme tagged SDR protein was then washed once with wash buffer (50 mM $NaH_2PO_4$, 300 mM NaCl; pH 8.0).

Modification of *E. coli* produced SDR proteins by *S. aureus* lysate: A 25 ml culture was started from an overnight culture of ΔPan Sdr mutant (ClfA-ClfB-SdrCDE-null; gift of Tim Foster, Trinity College Dublin) Newman *S. aureus* (starting $0D_{600}$ of 0.15) and grown in TSB for 3 hrs (exponential phase) 37° C., 200 rpm. The exponential phase culture was then resuspended in 1 ml of PBS and lysed with 200 ug/ml lysostaphin in the presence of 250 units of Benzonase Nuclease (Novagen) at 37° C. for 30 minutes. The lysates were cleared of debris by spinning down at maximum speed in a micro-centrifuge for 10 minutes at 4° C. Modification of NiNta captured *E. coli* SDR protein was carried out by incubation with cleared ΔPan Sdr mutant *S. aureus* lysates for 1 hr at 37° C.

Western Blotting of modified *E. coli* SDR protein: Non-modified or modified NiNta captured *E. coli* SDR protein samples were then washed 3× with wash buffer (50 mM $NaH_2PO_4$, 300 mM NaCl, 10 mM Imidazole; pH 8.0), prepared for Western Blotting and run on an 8% Tris Glycine Gel (Invitrogen). Western blots were blotted with either the rF1 antibody or an anti-Unizyme antibody (Genentech).

Identification of SDR Domain as Antigen for rF1

*S. aureus* expression of MBP-SD Constructs: The maltose binding protein (MBP) gene was PCR amplified from the pMAL-c5x vector (New England BioLabs [NEB], Ipswich, Mass., USA) from the sequence encoding the start of the mature protein until the sequence encoding the end of the Factor Xa cleavage site. The varying lengths of c-terminal His tagged SD (SD, SDS, DSD, SDSD, SDSDS, SDSDSD) were synthesized as single stranded oligonucleotides and annealed together to make double stranded dna. The Sdr region of the ClfA gene was PCR amplified from the sequence encoding the beginning (560D) of the Sdr region and included up to either the sequence encoding 618A or 709S of the SD region followed by the dna sequence coding for a His Tag from the respective plasmids pTet.ClfA.SD618A or pTet.ClfA.SD709S (Genentech). As a control, the sequence encoding the A domain of the ClfA gene from the beginning of the mature protein until the sequence encoding the end of the A domain (538G) followed by the sequence coding for a His Tag was PCR amplified from the plasmid pTet.ClfA.Adom.538G (Genentech). The MBP insert along with one of the various SD inserts or ClfA A domain were ligated into the pTet *S. aureus* expression vector (pSAS10 from Genentech). The resulting constructs were then electroporated into the *S. aureus* RN4220 Δ sortase (sortase deletion mutant strain in the RN4220 background).

A 20 ml culture of either the electroporated RN4220 Δ sortase or RN4220 Δ sortase empty (not carrying a pTet expression vector) was inoculated from an overnight culture (starting $OD_{600}$ of 0.15), grown for 1 hr in trypticase soy broth (TSB) supplemented with glucose (2 g/L) and then induced for protein expression for 2 hrs with anhydrotetracycline (200 ng/ml). At the end of the induction period, the *S. aureus* culture was resuspended in Column Buffer (150 mM NaCl, 20 mM Tris pH 7.5 and Roche protease inhibitor EDTA-free tablets) and lysed with 200 ug/ml lysostaphin in the presence of 250 units of Benzonase Nuclease (Novagen) at 37° C. for 30 minutes. The lysates were cleared of debris by spinning down at maximum speed in a micro-centrifuge for 10 minutes at 4° C. The cleared lysates were then incubated with amylose resin (NEB) along with a final EDTA concentration of 1 mM for 1.5 hrs at 4° C. to capture the expressed MBP-SD proteins.

Western Blotting of *S. aureus* expressed MBP-SD Constructs: Amylose resin with the captured MBP-SD proteins were washed three times with Column Buffer, further prepared for Western blotting analysis and run on an 8% Tris-glycine gel. Western blots were blotted with either the rF1 antibody, an anti-penta His antibody (Qiagen) or an anti-MBP antibody (NEB).

Results rF1 Reacts to a Unique Family of SDR (Ser-Asp-repeat) Proteins in *S. aureus* and *S. epidermidis*

Figure 6A:
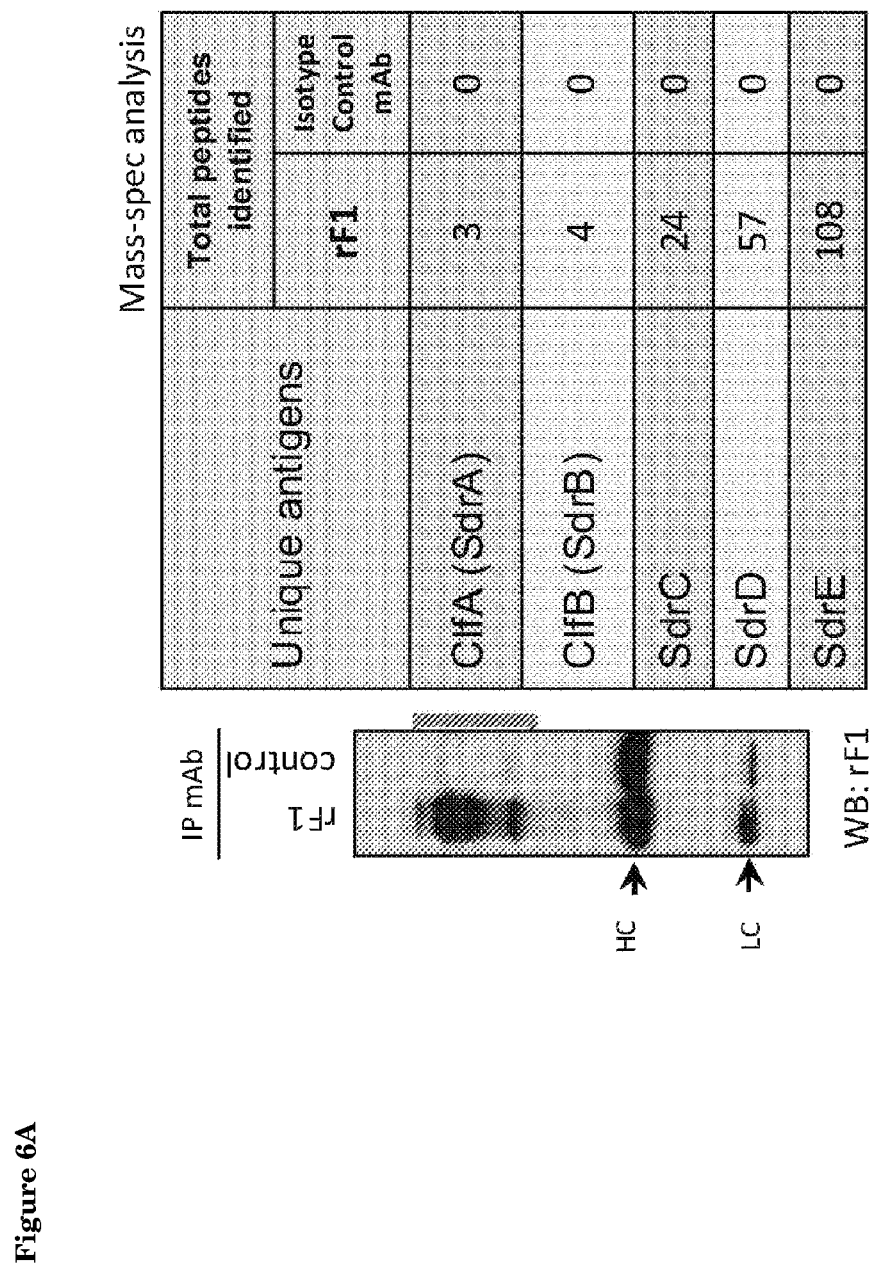
FIG. 6: rF1 antibody binds to SDR proteins. (a) Immunoprecipitation (IP) of a commercial teichoic acid preparation of *S. aureus* (Wood 46 strain) with rF1 or isotype control antibody, followed by Western blotting with rF1 antibody (left) and mass spectrometry analysis of fragments from the WTA preparation bound by rF1 antibody (right), (b) Immunoprecipitation (IP) of cell wall lysate of *S. aureus* (USA300 strain) with rF1 or control antibody, followed by Western blotting (WB) with rF1 antibody (left) and mass spectrometry analysis of cell wall fragments (USA300 strain) bound by rF1 antibody (right) (c) Immunoprecipitation of cell wall lysate of *S. epidermidis* with rF1 or isotype control antibody, followed by Western blotting with rF1 antibody (left), mass spectrometry analysis of cell wall fragments bound by rF1 antibody (right).
Figure 6B:
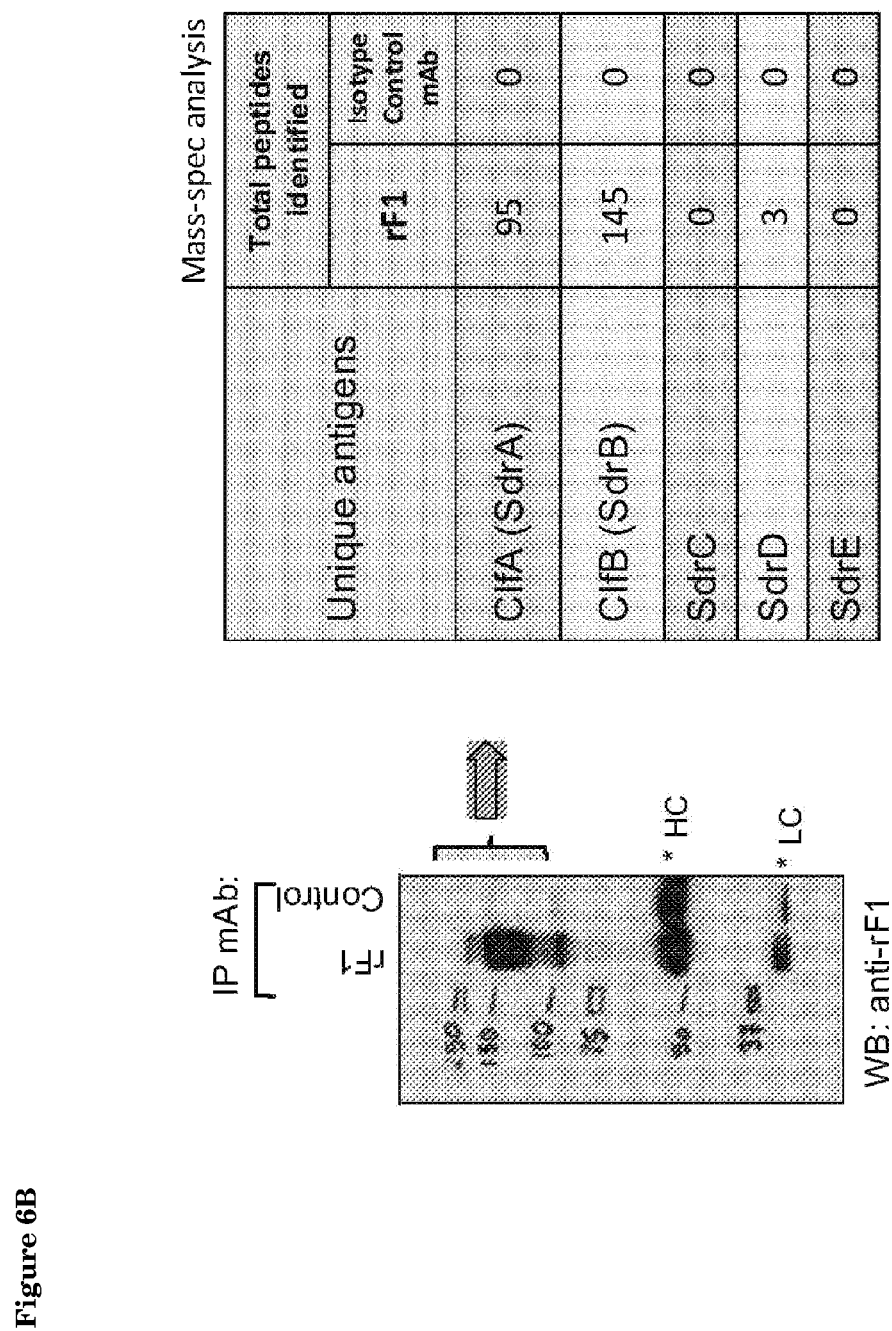

A commercial teichoic acid preparation and cell wall lysate (WTA) of *S. aureus* (USA300 strain) was tested for binding to rF1 after immunoprecipitation. rF1 binds to several components of the commercial teichoic acid preparation (FIG. 6A, left panel) and of the cell wall lysate of *S. aureus* (FIG. 6B, left panel). Using mass spectrometry these components of the WTA preparation and cell wall lysate were identified as ClfA (SdrA), ClfB (SdrB), SdrC, SdrD and SdrE (FIG. 6A, right panel and FIG. 6B, right panel)

Figure 6C:
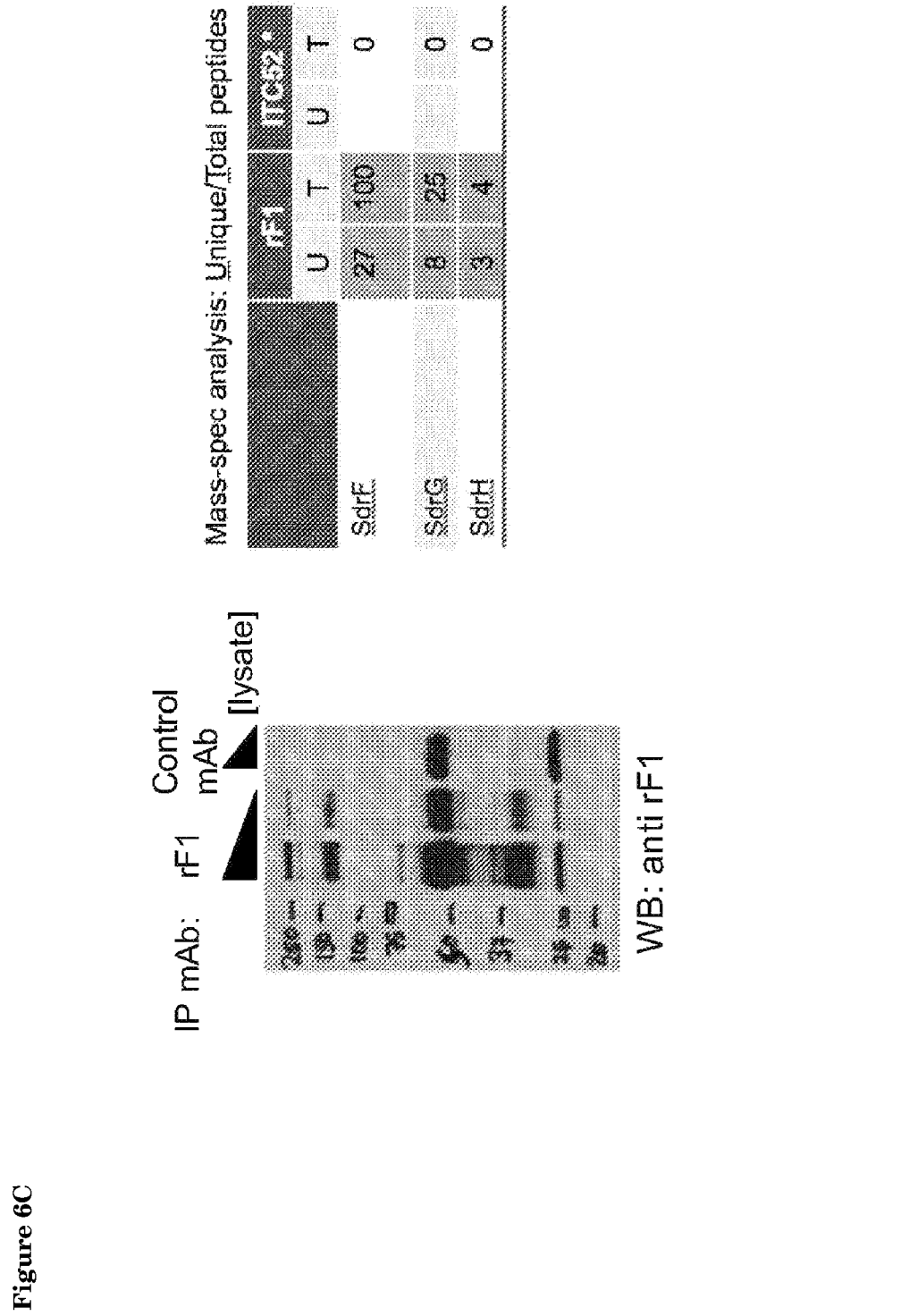

A cell wall lysate of *S. epidermidis* was tested for binding to rF1 after immunoprecipitation. FIG. 6C (left panel) shows binding of rF1 to several components of a cell wall lysate of *S. epidermidis*. These components were not identified with a control antibody. Using mass spectrometry these cell wall components were identified as SdrF, SdrG and SdrH (FIG. 6C right panel).

Exogenous ClfA Expression in *S. aureus* and *E. coli*

Figure 7A:
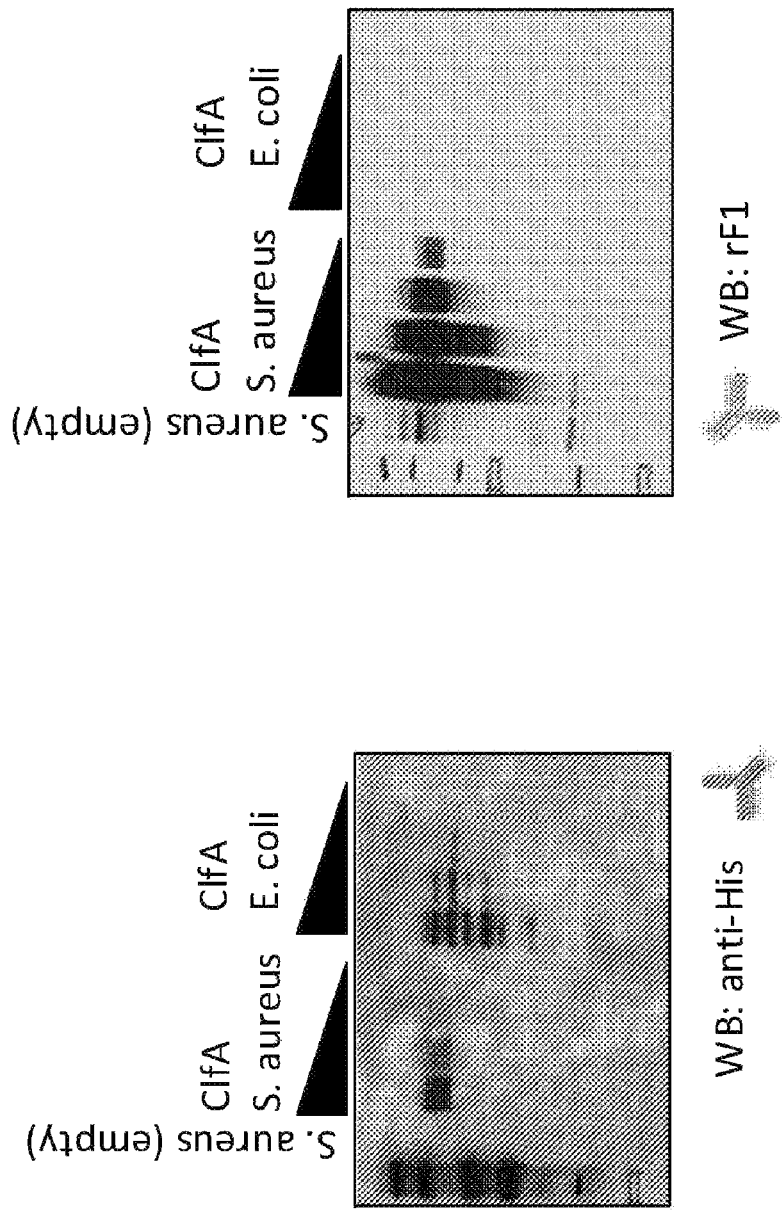
FIG. 7: Binding of rF1 to SDR proteins expressed in *S. aureus* and *E. coli*. (a) Western blotting of *S. aureus* and *E. coli* lysates containing overexpressed His-tagged ClfA using anti-His (left) and rF1 (right) antibody. (b) Western Bloting of *E. coli* cell lysates containing his-tagged ClfA, ClfB, SdrC, SdrD and SdrE following incubation with *S. aureus* lysate with rF1 (top) or anti-His (bottom) antibody.
Figure 7B:
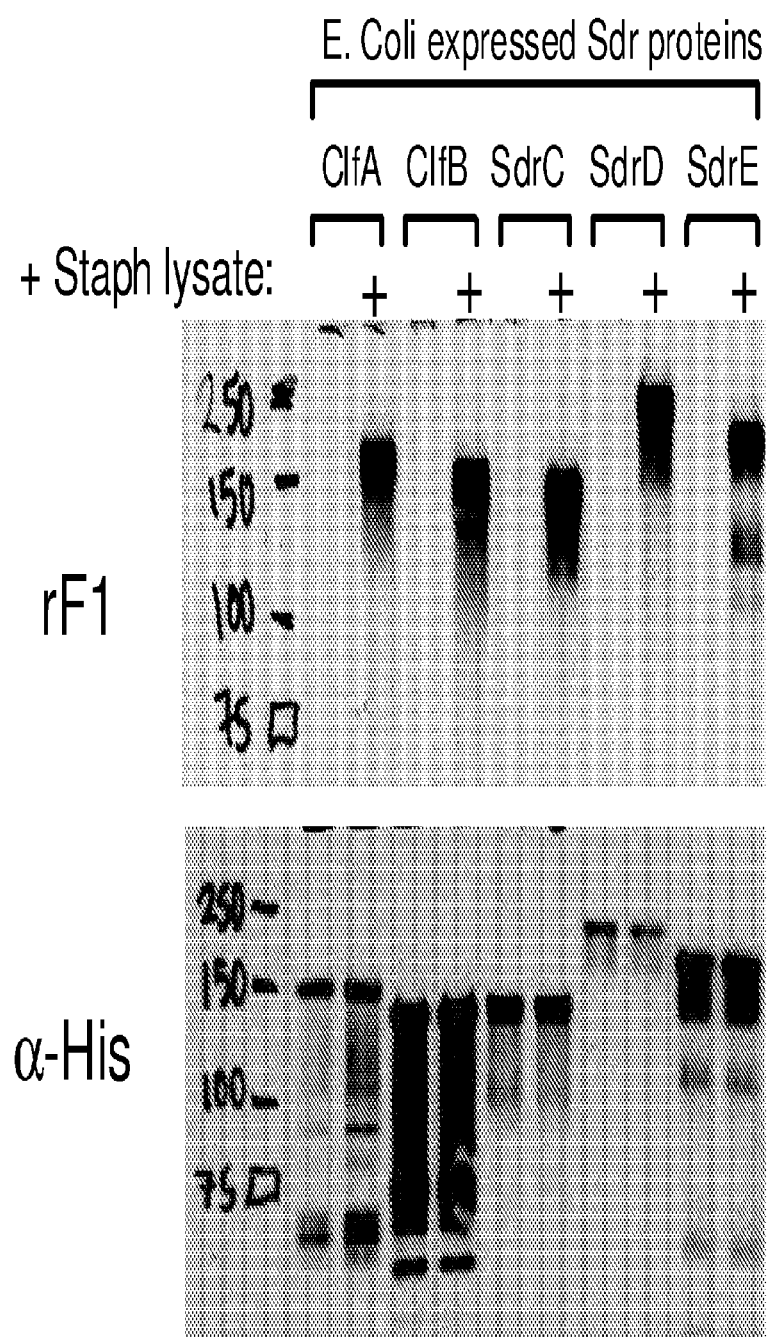
Figure 8:
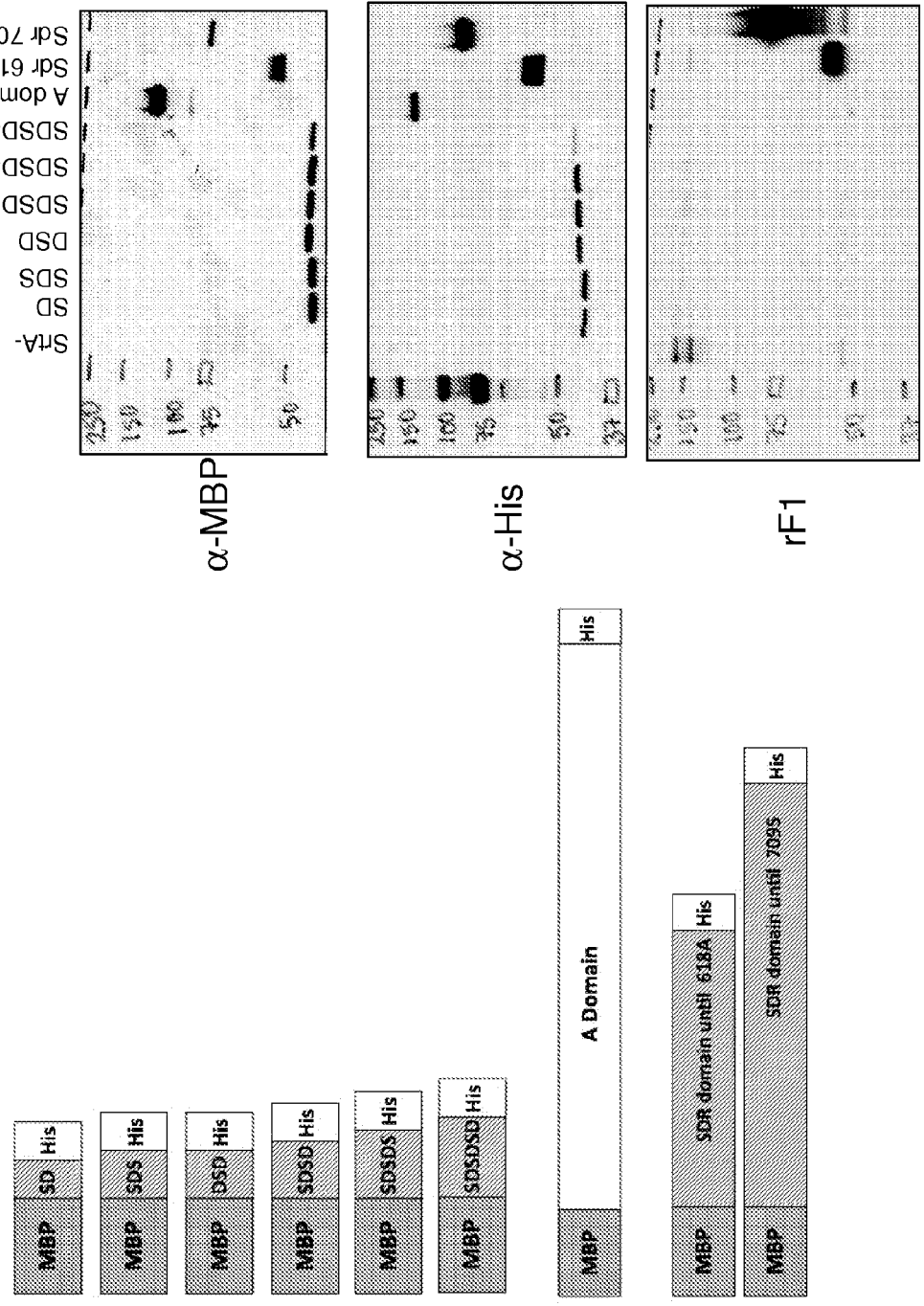
FIG. 8: rF1 binds to SDR domains expressed by *S. aureus*. Constructs expressed by *S. aureus* and tested for binding to rF1 (left), Western blots of *S. aureus* lysates containing the expressed constructs with anti-MBP (maltose binding protein), anti-His and rF1 antibody (right).

Exogenous ClfA expressed in *S. aureus* is reactive to rF1, whereas ClfA expressed in *E. coli* was not (FIG. 7A). However, incubation of *E. coli* expressed Sdr proteins ClfA (SdrA), ClfB (SdrB), SdrC, SdrD and SdrE with *S. aureus* lysate regained rF1 reactivity (FIG. 7B).

rF1 Binds to SDR Domains Expressed in *S. aureus* rF1 antibody binds to ClfA Sdr regions consisting of the ClfA 560D-618S and ClfA 560D-709S (FIG. 8) expressed in *S. aureus*. rF1 does not bind to the A-domain of ClfA or to small peptide sequences consisting of up to three SD repeats.

Example 4

Methods

Cloning of the Variable Regions of rF1 into pRK Vector

Phusion DNA polymerase, restriction enzymes EcoRV, KpnI, PvuII, ApaI, AgeI, and AhdI, T4 DNA ligase were purchased from New England BioLabs, Ipswich, Mass., USA. Pfu DNA polymerase, Quick change II Site-Directed Mutagenesis Kit were purchased from Stratagene/Agilent Technologies, Santa Clara, Calif., USA. 2% agarose gel was purchased from Invitrogen, Carlsbad, Calif., USA. pRK vectors pRK.LPG3.HuKappa and pRK.LPG4.HumanHC were obtained from Genentech/Roche, South San Francisco, Calif., USA.

The variable domains of heavy and light chains of rF1 Mab from the pCPEO vectors were placed into the pRK mammalian expression vectors. Polymerase chain reaction (PCR) was performed in a total volume of 50 µl using Pfu DNA polymerase according to standard PCR procedures. $V_H$ was amplified with the primers YiHCF) 5'-ATG GCT GAG GTG CAGCTG GTG GAG TCT G-3' (SEQ ID NO:18) and YiHCR2 5'-GAA CAC GCT GGGGCCCTT GGT GCT GGC ACT CGA GAC TGT GAC CAG GGT GCC AGG T*CC CCA G-3' (SEQ ID NO:19) (the restriction sites of PvuII and ApaI are underlined and the * indicates the single nucleotide G to T change to eliminate the internal ApaI site) and $V_L$ was amplified with the primers YiLCF 5'-CGG CTC GAC CGATATCCA GCT GAC CCA GAG-3' (SEQ ID NO:20) and YiLCR 5'-GAT TTC CAG CTT GGTACC CTG GCC G-3' (SEQ ID NO:21) (the EcoRV and KpnI are underlined). Unique PCR products with 393 ($V_H$) and 328 ($V_L$) bp, respectively, were directly digested by PvuII and ApaI for $V_H$, EcoRV and KpnI for $V_L$, followed by Gel purification (Invitrogen, Catalog# K2100-12). $V_H$ and $V_L$ were individually ligated into pRK vector fragments of pRK/PvuII, ApaI for Heavy chain and pRK/EcoRV, KpnI for light chain using T4 DNA ligase. The DNA plasmids were confirmed by restriction enzyme digestion patterns, i.e. rF1 $V_H$ released ~300 by and 5.8 kb bands by AgeI, whereas rF1$V_L$ shown 2.3 and 3.1 kb bands by AhdI on 2% agarose gel.

Chemical Stress Testing

By comparing antibody primary sequence data to experimentally observed degradation events, it has become clear that certain sequence motifs may be prone to degradation (i.e, aspartate isomerization at DD, DG, and DS sequences and asparagine deamidation at NG sequences). If such a degradation "hot spot" appears in the CDR of an antibody, binding and potency may be negatively impacted. For molecules containing hot spots, chemical stress testing provides a way to assess the susceptibility of these motifs to degradation by putting the antibody into a platform formulation buffer and comparing a control sample to one stressed at 40° C. for two weeks. If degradation is observed the primary sequence can be re-engineered to remove the hot spot.

After the sample is stressed for two weeks at 40° C., a variety of analytical assays are performed to assess where and how much degradation occurred. An imaged capillary isoelectric focusing (icIEF) analysis was performed to examine charge variants and the intact and reduced antibody mass was verified using mass spectrometry, and an LC-MS/MS peptide map was performed to obtain site-specific degradation information.

Mutagenesis

The rF1 pRK plasmids underwent a series of site-directed mutagenesis to stabilize the rF1 Mab by N (AAC) 53S (AGC) in heavy chain CDR2 with using FHV 5'-GGT GGC CAG CAT CAA CAGCGG CAA CAA CCC CTA CTA CG-3' (SEQ ID NO:22) and RHV 5'-CGT AGT AGG GGT TGT TGC CGCTGT TGA TGC TGG CCA CC-3' (SEQ ID NO:23) (mutagenesis site is underlined) via Quik change II Site-Directed Kit. The mutagenesis variant was sequenced.

Results

The primary sequence of antibody rF1 contained one potential asparagine deamidation site in light chain CDR2: N NGNN (SEQ ID NO:24). Stress testing revealed an increase of deamidation in stressed samples at N53 (numbering according to Kabat, 1991). Site-directed mutagenesis was performed to stabilize the rF1 Mab by N (AAC, (SEQ ID NO:25)) to 53S (AGC, (SEQ ID NO:26)) substitution in heavy chain CDR2. Sequencing of the mutagenesis variant confirmed an N53S mutation.

Example 5

Development of Cys Variants for Antibody-drug Conjugate (ADC) Applications

The rF1 pRK plasmids underwent a series of site-directed mutagenesis with oligos of rF1pRK.LC(205/210)VCF (468075) 5'-GGG CCT GAG CTC GCC CTGCAC AAA GAG CTT CAA CAG-3' (SEQ ID NO:27) and rF1pRK.LC (205/210)VCR (468076) 5'-CTG TTG AAG CTC TTT G TGCAG GGC GAG CTC AGG CCC-3' (SEQ ID NO:28) (Cys mutant is underlined) to generate the light chain linkers of rF1 thioMab, and rF1pRK.HCN53S.Al21CF (468464) 5'-CTG GTC ACA GTC TCG AGT TGC AGC ACC AAG GGC CCA TC-3' (SEQ ID NO:29) and rF1pRK.HCN53S.A121CR (468465) 5'-GAT GGG CCC TTG GTG CTGCAA CTC GAG ACT GTG ACC AG-3' (SEQ ID NO:30) (Cys mutant is underlined) to make the heavy chain linkers of rF1 thioMab via the Stratagene's Site-Directed method. Light chain V205C and heavy chain A114C were confirmed by sequencing of the variants (FIG. 9).

References

Diehl S. A. et al. *J Immunol* 180, 4805-4815 (2008)
Greenberg J. W. et al. *Infection and Immunity* 64, 3318-3325 (1996)
Jaleco A. C. et al. *Blood* 94, 2637-2646 (1999)
Kabat et al. Sequences of Proteins of Immunological interest, 5th Ed. Public Health Service, National Institute of Health, Bethesda, Md. (1991)
Keller R. et al. *Infect Immun* 60, 3664-3672 (1992)
Kwakkenbos M et al. *Nat Med* accepted for publication (2009)
Moran et al *NEMJ* 355, 666-674 (2006)
Polotsky V. Y. et al. *Infection and Immunity* 64, 380-383 (1996)
Scheeren F. A. et al. *Nat Immunol* 6, 303-313 (2005)
Shvarts A. et al. *Genes Dev* 16, 681-686 (2002)
Weidenmaier C. et al. *Nat Rev Microbiol* 6, 276-287 (2008)
Kwakkenbos M et al. *Nat Med.* 16(1):123-8 (2010)

We claim:

1. An isolated antibody comprising:
   (a) a heavy chain CDR1 sequence RFAMS (SEQ ID NO:1), and
   (b) a heavy chain CDR2 sequence SINNGNNPYYARS-VQY (SEQ ID NO:2) or SINSGNNPYYARSVQY (SEQ ID NO:60), and
   (c) a heavy chain CDR3 sequence DHPSSGWPTFDS (SEQ ID NO:3), and
   (d) a light chain CDR1 sequence RASENVGDWLA (SEQ ID NO:4), and
   (e) a light chain CDR2 sequence KTSILES (SEQ ID NO:5), and
   (f) a light chain CDR3 sequence QHYXRFPYT (SEQ ID NO:6), wherein X is I or M.

2. The antibody of claim 1 wherein the light chain CDR3 sequence is QHYIRFPYT(SEQ ID NO:6).

3. The antibody of claim 1 wherein the light chain CDR3 sequence is QHYMRFPYT(SEQ ID NO:6).

4. The antibody of claim 1 wherein the antibody has a variable heavy chain sequence comprising:
   (a) framework 1 (FW1) which has the sequence of EVQLLESGGGLVQPGGSLRLSCAASGFTLS (SEQ ID NO: 37);
   (b) framework 2 (FW2) which has the sequence of WVRQAPGRGLEWVA (SEQ ID NO: 39);
   (c) framework 3 (FW3) which has the sequence of RFTVS-RDVSQNTVSLQMNNLRAEDSATYFCAK (SEQ ID NO: 41); and
   (d) framework 4 (FW4) which has the sequence of WGPGTLVTVSS (SEQ ID NO: 43).

5. The antibody of claim 1 wherein the antibody has a variable light chain sequence comprising:
   (a) framework 1 (FW1) which has the sequence of DIQLTQSPSALPASVGDRVSITC (SEQ ID NO: 47);

(b) framework 2 (FW2) which has the sequence of WYRQKPGKAPNLLIY (SEQ ID NO: 49);
(c) framework 3 (FW3) which has the sequence of GVPSRFSGSGSGTEFTLTISSLQPDDFATYYC (SEQ ID NO: 51); and
(d) framework 4 (FW4) which has the sequence of FGQGTKVEIKRTV (SEQ ID NO: 59).

6. The antibody of claim 1 wherein the antibody has a variable heavy chain sequence comprising:
(a) framework 1 (FW1) which has the sequence of EVQLLESGGGLVQPGGSLRLSCAASGFTLS (SEQ ID NO: 37);
(b) framework 2 (FW2) which has the sequence of WVRQAPGRGLEWVA (SEQ ID NO: 39);
(c) framework 3 (FW3) which has the sequence of RFTVSRDVSQNTVSLQMNNLRAEDSATYFCAK (SEQ ID NO: 41); and
(d) framework 4 (FW4) which has the sequence of WGPGTLVTVSS (SEQ ID NO: 43)
and wherein the antibody has a variable light chain sequence comprising:
(a) framework 1 (FW1) which has the sequence of DIQLTQSPSALPASVGDRVSITC (SEQ ID NO: 47);
(b) framework 2 (FW2) which has the sequence of WYRQKPGKAPNLLIY (SEQ ID NO: 49);
(c) framework 3 (FW3) which has the sequence of GVPSRFSGSGSGTEFTLTISSLQPDDFATYYC (SEQ ID NO: 51); and
(d) framework 4 (FW4) which has the sequence of framework 4 (FW4) which has the sequence of FGQGTKLEIKRTV (SEQ ID NO: 53) or FGQGTKVEIKRTV (SEQ ID NO: 59).

7. The antibody of claim 1 wherein the antibody comprises a variable light chain having a sequence of DIQLTQSPSALPASVGDRVSITCRASENVGDWLAWYRQKPGKAPNLLIYKTSILESGVPSRFSGSGSGTEFTLTISSLQPDDFATYYCQHYMRFPYTFGQGTKVEIKRTV (SEQ ID NO:11).

8. The antibody of claim 1 wherein antibody comprises:
(a) a variable heavy chain comprising a sequence of EVQLLESGGGLVQPGGSLRLSCAASGFTLSRFAMSWVRQAPGRGLEWVASINNGNNPYYARSVQYRFTVSRDVSQNTVSLQMNNLRAEDSATYFCAKDHPSSGWPTFDSWGPGTLVTVSS (SEQ ID NO:7) and
(b) a variable light chain comprising a sequence of DIQLTQSPSALPASVGDRVSITCRASENVGDWLAWYRQKPGKAPNLLIYKTSILESGVPSRFSGSGSGTEFTLTISSLQPDDFATYYCQHYXRFPYTFGQGTKVEIKRTV, wherein X is I or M (SEQ ID NO:11).

9. The antibody of claim 1 wherein antibody comprises:
(a) a variable heavy chain comprising a sequence of EVQLVESGGGLVQPGGSLRLSCAASGFTLSRFAMSWVRQAPGRGLEWVASINNGNNPYYARSVQYRFTVSRDVSQNTVSLQMNNLRAEDSATYFCAKDHPSSGWPTFDSWGPGTLVTVSS (SEQ ID NO:9)
(b) a variable light chain comprising a sequence of DIQLTQSPSALPASVGDRVSITCRASENVGDWLAWYRQKPGKAPNLLIYKTSILESGVPSRFSGSGSGTEFTLTISSLQPDDFATYYCQHYXRFPYTFGQGTKLEIKRTV, wherein X is I or M (SEQ ID NO:8).

10. The antibody of claim 1 wherein antibody comprises:
(a) a variable heavy chain comprising a sequence of EVQLVESGGGLVQPGGSLRLSCAASGFTLSRFAMSWVRQAPGRGLEWVASINNGNNPYYARSVQYRFTVSRDVSQNTVSLQMNNLRAEDSATYFCAKDHPSSGWPTFDSWGPGTLVTVSS (SEQ ID NO:9)
(b) a variable light chain comprising a sequence of DIQLTQSPSALPASVGDRVSITCRASENVGDWLAWYRQKPGKAPNLLIYKTSILESGVPSRFSGSGSGTEFTLTISSLQPDDFATYYCQHYXRFPYTFGQGTKLEIKRA, wherein X is I or M (SEQ ID NO:10).

11. The antibody of claim 1 wherein antibody comprises:
(a) a variable heavy chain comprising a sequence of EVQLVESGGGLVQPGGSLRLSCAASGFTLSRFAMSWVRQAPGRGLEWVASINNGNNPYYARSVQYRFTVSRDVSQNTVSLQMNNLRAEDSATYFCAKDHPSSGWPTFDSWGPGTLVTVSS (SEQ ID NO:9) and
(b) a variable light chain comprising a sequence of DIQLTQSPSALPASVGDRVSITCRASENVGDWLAWYRQKPGKAPNLLIYKTSILESGVPSRFSGSGSGTEFTLTISSLQPDDFATYYCQHYXRFPYTFGQGTKVEIKRTV, wherein X is I or M (SEQ ID NO:11).

12. The antibody of claim 1 wherein antibody comprises:
(a) a variable heavy chain comprising a sequence of EVQLLESGGGLVQPGGSLRLSCAASGFTLSRFAMSWVRQAPGRGLEWVASINNGNNPYYARSVQYRFTVSRDVSQNTVSLQMNNLRAEDSATYFCAKDHPSSGWPTFDSWGPGTLVTVSS (SEQ ID NO:7) and
(b) a variable light chain comprising a sequence of DIQLTQSPSALPASVGDRVSITCRASENVGDWLAWYRQKPGKAPNLLIYKTSILESGVPSRFSGSGSGTEFTLTISSLQPDDFATYYCQHYXRFPYTFGQGTKLEIKRTV, wherein X is I or M (SEQ ID NO:8).

13. The antibody of claim 1 wherein antibody comprises:
(a) a variable heavy chain comprising a sequence of EVQLLESGGGLVQPGGSLRLSCAASGFTLSRFAMSWVRQAPGRGLEWVASINNGNNPYYARSVQYRFTVSRDVSQNTVSLQMNNLRAEDSATYFCAKDHPSSGWPTFDSWGPGTLVTVSS (SEQ ID NO:7) and
(b) a variable light chain comprising a sequence of DIQLTQSPSALPASVGDRVSITCRASENVGDWLAWYRQKPGKAPNLLIYKTSILESGVPSRFSGSGSGTEFTLTISSLQPDDFATYYCQHYXRFPYTFGQGTKLEIKRA, wherein X is I or M (SEQ ID NO:10).

14. The antibody of claim 1 wherein antibody comprises:
(a) a heavy chain comprising a sequence of SEQ ID NO: 55 and
(b) a light chain comprising a sequence of SEQ ID NO: 57.

15. The antibody of claim 1 wherein antibody comprises:
(a) a heavy chain comprising a sequence of SEQ ID NO: 56 and
(b) a light chain comprising a sequence of SEQ ID NO: 58.

16. The antibody according to claim 1 wherein the light chain CDR3 sequence is optimized to improve binding efficacy or stability, wherein the light chain CDR3 sequence is QHYXRFPYT (SEQ ID NO:6), wherein X is I or M.

17. The antibody of claim 1 wherein the antibody has a variable heavy chain sequence comprising:
(a) framework 1 (FW1) which has the sequence of EVQLVESGGGLVQPGGSLRLSCAASGFTLS (SEQ ID NO: 61);

(b) framework 2 (FW2) which has the sequence of WVRQAPGRGLEWVA (SEQ ID NO: 39);
(c) framework 3 (FW3) which has the sequence of RFTVSRDVSQNTVSLQMNNLRAEDSATYFCAK (SEQ ID NO: 41); and
(d) framework 4 (FW4) which has the sequence of WGPGTLVTVSS (SEQ ID NO: 43).

18. The antibody of claim 1 wherein the antibody has a variable heavy chain sequence comprising:
(a) framework 1 (FW1) which has the sequence of EVQLVESGGGLVQPGGSLRLSCAASGFTLS (SEQ ID NO: 61);
(b) framework 2 (FW2) which has the sequence of WVRQAPGRGLEWVA (SEQ ID NO: 39);
(c) framework 3 (FW3) which has the sequence of RFTVSRDVSQNTVSLQMNNLRAEDSATYFCAK (SEQ ID NO: 41); and
(d) framework 4 (FW4) which has the sequence of WGPGTLVTVSS (SEQ ID NO: 43)
and wherein the antibody has a variable light chain sequence comprising:
(a) framework 1 (FW1) which has the sequence of DIQLTQSPSALPASVGDRVSITC (SEQ ID NO: 47);
(b) framework 2 (FW2) which has the sequence of WYRQKPGKAPNLLIY (SEQ ID NO: 49);
(c) framework 3 (FW3) which has the sequence of GVPSRFSGSGSGTEFTLTISSLQPDDFATYYC (SEQ ID NO: 51); and
(d) framework 4 (FW4) which has the sequence of framework 4 (FW4) which has the sequence of FGQGTKLEIKRTV (SEQ ID NO: 53) or FGQGTKVEIKRTV (SEQ ID NO: 59).

19. The antibody of claim 1 wherein the antibody comprises a variable heavy chain having a sequence of:
EVQLVESGGGLVQPGGSLRLSCAASGFTLSRFAMSWVRQAPGRGLEWVASINSGNNPYYARSVQYRFTVSRDVSQNTVSLQMNNLRAEDSATYFCAKDHPSSGWPTFDSWGPGTLVTVSS (SEQ ID NO:62).

20. The antibody of claim 1 wherein antibody comprises:
(a) a variable heavy chain comprising a sequence of EVQLVESGGGLVQPGGSLRLSCAASGFTLSRFAMSWVRQAPGRGLEWVASINSGNNPYYARSVQYRFTVSRDVSQNTVSLQMNNLRAEDSATYFCAKDHPSSGWPTFDSWGPGTLVTVSS (SEQ ID NO:62) and
(b) a variable light chain comprising a sequence of DIQLTQSPSALPASVGDRVSITCRASENVGDWLAWYRQKPGKAPNLLIYKTSILESGVPSRFSGSGSGTEFTLTISSLQPDDFATYYCQHYXRFPYTFGQGTKVEIKRTV, wherein X is I or M (SEQ ID NO:11).

21. The antibody of claim 20 wherein the variable light chain comprising a sequence of:
DIQLTQSPSALPASVGDRVSITCRASENVGDWLAWYRQKPGKAPNLLIYKTSILESGVPSRFSGSGSGTEFTLTISSLQPDDFATYYCQHYIRFPYTFGQGTKVEIKRTV (SEQ ID NO:11).

22. The antibody of claim 20 wherein the variable light chain comprising a sequence of:
DIQLTQSPSALPASVGDRVSITCRASENVGDWLAWYRQKPGKAPNLLIYKTSILESGVPSRFSGSGSGTEFTLTISSLQPDDFATYYCQHYMRFPYTFGQGTKVEIKRTV (SEQ ID NO:11).

23. The antibody of claim 22, further comprising a heavy chain constant domain comprising the sequence of:
ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCP (SEQ ID NO:63).

24. The antibody of claim 22, further comprising a light chain constant domain comprising the sequence of:
AAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO:64).

25. The antibody of claim 22, further comprising
(a) a heavy chain constant domain comprising the sequence of:
ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCP (SEQ ID NO:63) and;
(b) a light chain constant domain comprising the sequence of:
AAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO:64).

26. A pharmaceutical composition comprising the antibody of claim 1.

27. A pharmaceutical composition comprising the antibody of claim 25.

28. The antibody of claim 1 wherein the antibody is coupled to a cytotoxic agent.

29. The antibody of claim 28 wherein the cytotoxic agent is an antibiotic.

30. The antibody of claim 25 wherein the antibody is coupled to a cytotoxic agent.

31. The antibody of claim 30 wherein the cytotoxic agent is an antibiotic.

32. The antibody of claim 1 wherein the antibody binds to a gram positive bacterium.

33. The antibody of claim 32 wherein the gram positive bacterium is a *Staphylococcus* species.

34. The antibody of claim 33 wherein the Staphylococcus species is *S. aureus, S. epidermidis, S. caprae, S. saprophyticus, S. capitis*, or methicillin-resistant *S. aureus* (MRSA).

35. The antibody of claim 25 wherein the antibody binds to a gram positive bacterium.

36. The antibody of claim 35 wherein the gram positive bacterium is a *Staphylococcus* species.

37. The antibody of claim 36 wherein the Staphylococcus species is *S. aureus, S. epidermidis, S. caprae, S. saprophyticus, S. capitis*, or methicillin-resistant *S. aureus* (MRSA).

38. A method of treating a gram-positive bacterium-related disorder comprising administering to an individual in need thereof a therapeutically effective amount of an antibody comprising:
(a) a heavy chain CDR1 sequence RFAMS (SEQ ID NO:1), and
(b) a heavy chain CDR2 sequence SINNGNNPYYARSVQY (SEQ ID NO:2) or SINSGNNPYYARSVQY (SEQ ID NO:60), and
(c) a heavy chain CDR3 sequence DHPSSGWPTFDS (SEQ ID NO:3), and
(d) a light chain CDR1 sequence RASENVGDWLA (SEQ ID NO:4), and (e) a light chain CDR2 sequence KTSILES (SEQ ID NO:5), and
(f) a light chain CDR3 sequence QHYXRFPYT (SEQ ID NO:6), wherein X is I or M.

39. The method of claim 38 wherein the light chain CDR3 sequence is QHYIRFPYT (SEQ ID NO:6).

40. The method of claim 38 wherein the light chain CDR3 sequence is QHYMRFPYT (SEQ ID NO:6).

41. The method of claim 38 wherein the antibody has a variable heavy chain sequence comprising:
(a) framework 1 (FW1) which has the sequence of EVQLLESGGGLVQPGGSLRLSCAASGFTLS (SEQ ID NO: 37) or EVQLVESGGGLVQPGGSLRLSCAASGFTLS (SEQ ID NO: 61);
(b) framework 2 (FW2) which has the sequence of WVRQAPGRGLEWVA (SEQ ID NO: 39);
(c) framework 3 (FW3) which has the sequence of RFTVSRDVSQNTVSLQMNNLRAEDSATYFCAK (SEQ ID NO: 41); and
(d) framework 4 (FW4) which has the sequence of WGPGTLVTVSS (SEQ ID NO: 43).

42. The method of claim 38 wherein the antibody has a variable light chain sequence comprising:
(a) framework 1 (FW1) which has the sequence of DIQLTQSPSALPASVGDRVSITC (SEQ ID NO: 47);
(b) framework 2 (FW2) which has the sequence of WYRQKPGKAPNLLIY (SEQ ID NO: 49);
(c) framework 3 (FW3) which has the sequence of GVPSRFSGSGSGTEFTLTISSLQPDDFATYYC (SEQ ID NO: 51); and
(d) framework 4 (FW4) which has the sequence of FGQGTKVEIKRTV (SEQ ID NO: 59).

43. The method of claim 38 wherein the antibody has a variable heavy chain sequence comprising:
a) framework 1 (FW1) which has the sequence of EVQLLESGGGLVQPGGSLRLSCAASGFTLS (SEQ ID NO: 37) or EVQLVESGGGLVQPGGSLRLSCAASGFTLS (SEQ ID NO: 61);
(b) framework 2 (FW2) which has the sequence of WVRQAPGRGLEWVA (SEQ ID NO: 39);
(c) framework 3 (FW3) which has the sequence of RFTVSRDVSQNTVSLQMNNLRAEDSATYFCAK (SEQ ID NO: 41); and
(d) framework 4 (FW4) which has the sequence of WGPGTLVTVSS (SEQ ID NO: 43)
and wherein the antibody has a variable light chain sequence comprising:
(a) framework 1 (FW1) which has the sequence of DIQLTQSPSALPASVGDRVSITC (SEQ ID NO: 47);
(b) framework 2 (FW2) which has the sequence of WYRQKPGKAPNLLIY (SEQ ID NO: 49);
(c) framework 3 (FW3) which has the sequence of GVPSRFSGSGSGTEFTLTISSLQPDDFATYYC (SEQ ID NO: 51); and
(d) framework 4 (FW4) which has the sequence of framework 4 (FW4) which has the sequence of FGQGTKLEIKRTV (SEQ ID NO: 53) or FGQGTKVEIKRTV (SEQ ID NO: 59).

44. The method of claim 38 wherein the antibody comprises a variable light chain having a sequence of DIQLTQSPSALPASVGDRVSITCRASENVGDWLAWYRQKPGKAPNLLIYKTSILESGVPSRFSGSGSGTEFTLTISSLQPDDFATYYCQHYMRFPYTFGQGTKVEIKRTV (SEQ ID NO:11).

45. The method of claim 38 wherein the antibody comprises:

(a) a variable heavy chain comprising a sequence of EVQLLESGGGLVQPGGSLRLSCAASGFTLSRFAMSWVRQAPGRGLEWVASINNGNNPYYARSVQYRFTVSRDVSQNTVSLQMNNLRAEDSATYFCAKDHPSSGWPTFDSWGPGTLVTVSS (SEQ ID NO:7) and
(b) a variable light chain comprising a sequence of DIQLTQSPSALPASVGDRVSITCRASENVGDWLAWYRQKPGKAPNLLIYKTSILESGVPSRFSGSGSGTEFTLTISSLQPDDFATYYCQHYXRFPYTFGQGTKVEIKRTV, wherein X is I or M (SEQ ID NO:11).

46. The method of claim 38 wherein the antibody comprises:
(a) a variable heavy chain comprising a sequence of EVQLVESGGGLVQPGGSLRLSCAASGFTLSRFAMSWVRQAPGRGLEWVASINNGNNPYYARSVQYRFTVSRDVSQNTVSLQMNNLRAEDSATYFCAKDHPSSGWPTFDSWGPGTLVTVSS (SEQ ID NO:9)
(b) a variable light chain comprising a sequence of DIQLTQSPSALPASVGDRVSITCRASENVGDWLAWYRQKPGKAPNLLIYKTSILESGVPSRFSGSGSGTEFTLTISSLQPDDFATYYCQHYXRFPYTFGQGTKLEIKRTV, wherein X is I or M (SEQ ID NO:8).

47. The method of claim 38 wherein the antibody comprises:
(a) a variable heavy chain comprising a sequence of EVQLVESGGGLVQPGGSLRLSCAASGFTLSRFAMSWVRQAPGRGLEWVASINNGNNPYYARSVQYRFTVSRDVSQNTVSLQMNNLRAEDSATYFCAKDHPSSGWPTFDSWGPGTLVTVSS (SEQ ID NO:9)
(b) a variable light chain comprising a sequence of DIQLTQSPSALPASVGDRVSITCRASENVGDWLAWYRQKPGKAPNLLIYKTSILESGVPSRFSGSGSGTEFTLTISSLQPDDFATYYCQHYXRFPYTFGQGTKLEIKRA, wherein X is I or M (SEQ ID NO:10).

48. The method of claim 38 wherein the antibody comprises:
(a) a variable heavy chain comprising a sequence of EVQLVESGGGLVQPGGSLRLSCAASGFTLSRFAMSWVRQAPGRGLEWVASINNGNNPYYARSVQYRFTVSRDVSQNTVSLQMNNLRAEDSATYFCAKDHPSSGWPTFDSWGPGTLVTVSS (SEQ ID NO:9) and
(b) a variable light chain comprising a sequence of DIQLTQSPSALPASVGDRVSITCRASENVGDWLAWYRQKPGKAPNLLIYKTSILESGVPSRFSGSGSGTEFTLTISSLQPDDFATYYCQHYXRFPYTFGQGTKVEIKRTV, wherein X is I or M (SEQ ID NO:11).

49. The method of claim 38 wherein the antibody comprises:
(a) a variable heavy chain comprising a sequence of EVQLLESGGGLVQPGGSLRLSCAASGFTLSRFAMSWVRQAPGRGLEWVASINNGNNPYYARSVQYRFTVSRDVSQNTVSLQMNNLRAEDSATYFCAKDHPSSGWPTFDSWGPGTLVTVSS (SEQ ID NO:7) and
(b) a variable light chain comprising a sequence of DIQLTQSPSALPASVGDRVSITCRASENVGDWLAWYRQKPGKAPNLLIYKTSILES- GVPSRFSGSGSGTEFTLTISSLQPDDFA-TYYCQHYXRFPYTFGQGTKLEIKRTV, wherein X is I or M (SEQ ID NO:8).

50. The method of claim 38 wherein the antibody comprises:
 (a) a variable heavy chain comprising a sequence of EVQLLESGGGLVQPGGSLRLSCAASG-FTLSRFAMSWVRQAPGRGLEWVASIN-NGNNPYYARSVQYRFTVSRDVSQNTVS-LQMNNLRAEDSATYFCAKDHPSSGWPTFDSW-GPGTLVTVSS (SEQ ID NO:7) and
 (b) a variable light chain comprising a sequence of DIQLTQSPSALPASVGDRVSITCRASEN-VGDWLAWYRQKPGKAPNLLIYKTSILES-GVPSRFSGSGSGTEFTLTISSLQPDDFA-TYYCQHYXRFPYTFGQGTKLEIKRA, wherein X is I or M (SEQ ID NO:10).

51. The method of claim 38 wherein the antibody comprises:
 (a) a heavy chain comprising a sequence of SEQ ID NO: 55 and
 (b) a light chain comprising a sequence of SEQ ID NO: 57.

52. The method of claim 38 wherein the antibody comprises:
 (a) a heavy chain comprising a sequence of SEQ ID NO: 56 and
 (b) a light chain comprising a sequence of SEQ ID NO: 58.

53. The method of claim 38 wherein the light chain CDR3 sequence is optimized to improve binding efficacy or stability, wherein the light chain CDR3 sequence is QHYXRFPYT (SEQ ID NO:6), wherein X is I or M.

54. The method of claim 38 wherein the antibody comprises a variable heavy chain having a sequence of: EVQLVESGGGLVQPGGSLRLSCAASG-FTLSRFAMSWVRQAPGRGLEWVASINS-GNNPYYARSVQYRFTVSRDVSQNTVS-LQMNNLRAEDSATYFCAKDHPSSGWPTFDSWGPG-TLVTVSS (SEQ ID NO:62).

55. The method of claim 38 wherein the antibody comprises:
 (a) a variable heavy chain comprising a sequence of EVQLVESGGGLVQPGGSLRLSCAASG-FTLSRFAMSWVRQAPGRGLEWVASINS-GNNPYYARSVQYRFTVSRDVSQNTVS-LQMNNLRAEDSATYFCAKDHPSSGWPTFDSW-GPGTLVTVSS (SEQ ID NO:62) and
 (b) a variable light chain comprising a sequence of DIQLTQSPSALPASVGDRVSITCRASEN-VGDWLAWYRQKPGKAPNLLIYKTSILES-GVPSRFSGSGSGTEFTLTISSLQPDDFA-TYYCQHYXRFPYTFGQGTKVEIKRTV, wherein X is I or M (SEQ ID NO:11).

56. The method of claim 55 wherein the variable light chain comprises a sequence of:
 DIQLTQSPSALPASVGDRVSITCRASEN-VGDWLAWYRQKPGKAPNLLIYKTSILES-GVPSRFSGSGSGTEFTLTISSLQPDDFA-TYYCQHYIRFPYTFGQGTKVEIKRTV (SEQ ID NO:11).

57. The method of claim 55 wherein the variable light chain comprises a sequence of:
 DIQLTQSPSALPASVGDRVSITCRASEN-VGDWLAWYRQKPGKAPNLLIYKTSILES-GVPSRFSGSGSGTEFTLTISSLQPDDFA-TYYCQHYMRFPYTFGQGTKVEIKRTV (SEQ ID NO:11).

58. The method of claim 57 wherein the antibody further comprises a heavy chain constant domain comprising the sequence of:
 ASTKGPSVFPLAPSSKSTSGGTAALG-CLVKDYFPEPVTVSWNSGALTSGVHTF-PAVLQSSGLYSLSSVVTVPSSSLGTQTY-ICNVNHKPSNTKVDKKVEPKSCDKTHTCP (SEQ ID NO:63).

59. The method of claim 57 wherein the antibody further comprises a light chain constant domain comprising the sequence of:
 AAPSVFIFPPSDEQLKSGTASVVCLLNN-FYPREAKVQWKVDNALQSGNSQESVTE-QDSKDSTYSLSSTLTLSKADYEKHKVY-ACEVTHQGLSSPVTKSFNRGEC (SEQ ID NO:64).

60. The method of claim 57 wherein the antibody further comprises
 (a) a heavy chain constant domain comprising the sequence of: ASTKGPSVFPLAPSSKSTSGGTAALG-CLVKDYFPEPVTVSWNSGALTSGVHTF-PAVLQSSGLYSLSSVVTVPSSSLGTQTY-ICNVNHKPSNTKVDKKVEPKSCDKTHTCP (SEQ ID NO:63) and;
 (b) a light chain constant domain comprising the sequence of: AAPSVFIFPPSDEQLKSGTASVVCLLNN-FYPREAKVQWKVDNALQSGNSQESVTE-QDSKDSTYSLSSTLTLSKADYEKHKVY-ACEVTHQGLSSPVTKSFNRGEC (SEQ ID NO:64).

61. The method of claim 38 wherein the antibody is coupled to a cytotoxic agent.

62. The method of claim 61 wherein the cytotoxic agent is an antibiotic.

63. The method of claim 38 wherein the antibody binds to a gram-positive bacterium.

64. The method of claim 63 wherein the gram positive bacterium is a *Staphylococcus* species.

65. The method of claim 64 wherein the *Staphylococcus* species is *S. aureus, S. epidermidis, S. caprae, S. saprophyticus, S. capitis*, or methicillin-resistant *S. aureus* (MRSA).

66. The method of claim 38 wherein said individual has been diagnosed as infected by *S. aureus* and/or *S. epidermidis*.

67. The method of claim 38 wherein said individual has been diagnosed as infected by MRSA.

68. The method of claim 60 wherein the antibody is coupled to a cytotoxic agent.

69. The method of claim 68 wherein the cytotoxic agent is an antibiotic.

70. The method of claim 60 wherein the antibody binds to a gram-positive bacterium.

71. The method of claim 70 wherein the gram positive bacterium is a *Staphylococcus* species.

72. The method of claim 71 wherein the *Staphylococcus* species is *S. aureus, S. epidermidis, S. caprae, S. saprophyticus, S. capitis*, or methicillin-resistant *S. aureus* (MRSA).

73. The method of claim 38 wherein said individual has been diagnosed as infected by *S. aureus* and/or *S. epidermidis*.

74. The method of claim 38 wherein said individual has been diagnosed as infected by MRSA.

* * * * *

SEQUENCE LISTING

<160> NUMBER OF SEQ ID NOS: 64

<210> SEQ ID NO 1
<211> LENGTH: 5
<212> TYPE: PRT
<213> ORGANISM: Artificial Sequence
<220> FEATURE:

```
<223> OTHER INFORMATION: Synthetic construct
<220> FEATURE:
<223> OTHER INFORMATION: CDR1 Heavy Chain

<400> SEQUENCE: 1

Arg Phe Ala Met Ser
1               5

<210> SEQ ID NO 2
<211> LENGTH: 16
<212> TYPE: PRT
<213> ORGANISM: Artificial Sequence
<220> FEATURE:
<223> OTHER INFORMATION: Synthetic construct
<220> FEATURE:
<223> OTHER INFORMATION: CDR2 Heavy Chain

<400> SEQUENCE: 2

Ser Ile Asn Asn Gly Asn Asn Pro Tyr Tyr Ala Arg Ser Val Gln Tyr
1               5                   10                  15

<210> SEQ ID NO 3
<211> LENGTH: 12
<212> TYPE: PRT
<213> ORGANISM: Artificial Sequence
<220> FEATURE:
<223> OTHER INFORMATION: Synthetic construct
<220> FEATURE:
<223> OTHER INFORMATION: CDR3 Heavy Chain

<400> SEQUENCE: 3

Asp His Pro Ser Ser Gly Trp Pro Thr Phe Asp Ser
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic construct
<220> FEATURE:
<223> OTHER INFORMATION: CDR1 Light Chain

<400> SEQUENCE: 4

Arg Ala Ser Glu Asn Val Gly Asp Trp Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic construct
<220> FEATURE:
<223> OTHER INFORMATION: CDR2 Light Chain

<400> SEQUENCE: 5

Lys Thr Ser Ile Leu Glu Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic construct
<220> FEATURE:
<223> OTHER INFORMATION: CDR3 Light Chain
<220> FEATURE:
<221> NAME/KEY: VARIANT
```

```
<222> LOCATION: 4
<223> OTHER INFORMATION: Xaa = M or I

<400> SEQUENCE: 6

Gln His Tyr Xaa Arg Phe Pro Tyr Thr
1               5

<210> SEQ ID NO 7
<211> LENGTH: 120
<212> TYPE: PRT
<213> ORGANISM: Artificial Sequence
<220> FEATURE:
<223> OTHER INFORMATION: Synthetic construct
<220> FEATURE:
<223> OTHER INFORMATION: F1 Anitbody Variant Heavy Chain

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Arg Phe
            20                  25                  30

Ala Met Ser Trp Val Arg Gln Ala Pro Gly Arg Gly Leu Glu Trp Val
        35                  40                  45

Ala Ser Ile Asn Asn Gly Asn Asn Pro Tyr Tyr Ala Arg Ser Val Gln
    50                  55                  60

Tyr Arg Phe Thr Val Ser Arg Asp Val Ser Gln Asn Thr Val Ser Leu
65                  70                  75                  80

Gln Met Asn Asn Leu Arg Ala Glu Asp Ser Ala Thr Tyr Phe Cys Ala
                85                  90                  95

Lys Asp His Pro Ser Ser Gly Trp Pro Thr Phe Asp Ser Trp Gly Pro
            100                 105                 110

Gly Thr Leu Val Thr Val Ser Ser
        115                 120

<210> SEQ ID NO 8
<211> LENGTH: 110
<212> TYPE: PRT
<213> ORGANISM: Artificial Sequence
<220> FEATURE:
<223> OTHER INFORMATION: Synthetic construct
<220> FEATURE:
<223> OTHER INFORMATION: F1 Antibody Variant Light Chain
<220> FEATURE:
<221> NAME/KEY: VARIANT
<222> LOCATION: 92
<223> OTHER INFORMATION: Xaa = M or I

<400> SEQUENCE: 8

Asp Ile Gln Leu Thr Gln Ser Pro Ser Ala Leu Pro Ala Ser Val Gly
1               5                   10                  15

Asp Arg Val Ser Ile Thr Cys Arg Ala Ser Glu Asn Val Gly Asp Trp
            20                  25                  30

Leu Ala Trp Tyr Arg Gln Lys Pro Gly Lys Ala Pro Asn Leu Leu Ile
        35                  40                  45

Tyr Lys Thr Ser Ile Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Tyr Xaa Arg Phe Pro Tyr
                85                  90                  95

Thr Phe Gly Gln Gly Thr Lys Leu Glu Ile Lys Arg Thr Val
            100                 105                 110
```

<210> SEQ ID NO 9
<211> LENGTH: 120
<212> TYPE: PRT
<213> ORGANISM: Artificial Sequence
<220> FEATURE:
<223> OTHER INFORMATION: Synthetic construct
<220> FEATURE:
<223> OTHER INFORMATION: F1 Antibody Variant Heavy Chain

<400> SEQUENCE: 9

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Leu Ser Arg Phe
            20                  25                  30

Ala Met Ser Trp Val Arg Gln Ala Pro Gly Arg Gly Leu Glu Trp Val
        35                  40                  45

Ala Ser Ile Asn Asn Gly Asn Asn Pro Tyr Tyr Ala Arg Ser Val Gln
    50                  55                  60

Tyr Arg Phe Thr Val Ser Arg Asp Val Ser Gln Asn Thr Val Ser Leu
65                  70                  75                  80

Gln Met Asn Asn Leu Arg Ala Glu Asp Ser Ala Thr Tyr Phe Cys Ala
                85                  90                  95

Lys Asp His Pro Ser Ser Gly Trp Pro Thr Phe Asp Ser Trp Gly Pro
            100                 105                 110

Gly Thr Leu Val Thr Val Ser Ser
        115                 120
```

<210> SEQ ID NO 10
<211> LENGTH: 109
<212> TYPE: PRT
<213> ORGANISM: Artificial Sequence
<220> FEATURE:
<223> OTHER INFORMATION: Synthetic construct
<220> FEATURE:
<223> OTHER INFORMATION: F1 Antibody Variant Light Chain
<220> FEATURE:
<221> NAME/KEY: VARIANT
<222> LOCATION: 92
<223> OTHER INFORMATION: Xaa = M or I

<400> SEQUENCE: 10

```
Asp Ile Gln Leu Thr Gln Ser Pro Ser Ala Leu Pro Ala Ser Val Gly
 1               5                  10                  15

Asp Arg Val Ser Ile Thr Cys Arg Ala Ser Glu Asn Val Gly Asp Trp
            20                  25                  30

Leu Ala Trp Tyr Arg Gln Lys Pro Gly Lys Ala Pro Asn Leu Leu Ile
        35                  40                  45

Tyr Lys Thr Ser Ile Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Tyr Xaa Arg Phe Pro Tyr
                85                  90                  95

Thr Phe Gly Gln Gly Thr Lys Leu Glu Ile Lys Arg Ala
            100                 105
```

<210> SEQ ID NO 11
<211> LENGTH: 110
<212> TYPE: PRT
<213> ORGANISM: Artificial Sequence
<220> FEATURE:

<223> OTHER INFORMATION: Synthetic construct
<220> FEATURE:
<223> OTHER INFORMATION: F1 Antibody Variant Light Chain
<220> FEATURE:
<221> NAME/KEY: VARIANT
<222> LOCATION: 92
<223> OTHER INFORMATION: Xaa = M or I

<400> SEQUENCE: 11

Asp Ile Gln Leu Thr Gln Ser Pro Ser Ala Leu Pro Ala Ser Val Gly
 1               5                  10                  15

Asp Arg Val Ser Ile Thr Cys Arg Ala Ser Glu Asn Val Gly Asp Trp
            20                  25                  30

Leu Ala Trp Tyr Arg Gln Lys Pro Gly Lys Ala Pro Asn Leu Leu Ile
        35                  40                  45

Tyr Lys Thr Ser Ile Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Tyr Xaa Arg Phe Pro Tyr
                85                  90                  95

Thr Phe Gly Gln Gly Thr Lys Val Glu Ile Lys Arg Thr Val
            100                 105                 110

<210> SEQ ID NO 12
<211> LENGTH: 15
<212> TYPE: DNA
<213> ORGANISM: Artificial Sequence
<220> FEATURE:
<223> OTHER INFORMATION: Synthetic construct
<220> FEATURE:
<223> OTHER INFORMATION: F1 Heavy Chain CDR1

<400> SEQUENCE: 12
cgctttgcca tgagc                                                      15

<210> SEQ ID NO 13
<211> LENGTH: 48
<212> TYPE: DNA
<213> ORGANISM: Artificial Sequence
<220> FEATURE:
<223> OTHER INFORMATION: Synthetic construct
<220> FEATURE:
<223> OTHER INFORMATION: F1 Heavy Chain CDR2

<400> SEQUENCE: 13
tcgatcaata atgggaataa cccatactac gcacggtcgg tacaatac                  48

<210> SEQ ID NO 14
<211> LENGTH: 36
<212> TYPE: DNA
<213> ORGANISM: Artificial Sequence
<220> FEATURE:
<223> OTHER INFORMATION: Synthetic construct
<220> FEATURE:
<223> OTHER INFORMATION: F1 Heavy Chain CDR3

<400> SEQUENCE: 14
gatcacccta gtagtggctg gcccaccttt gactcc                               36

<210> SEQ ID NO 15
<211> LENGTH: 33
<212> TYPE: DNA
<213> ORGANISM: Artificial Sequence
<220> FEATURE:
<223> OTHER INFORMATION: Synthetic construct

```
<220> FEATURE:
<223> OTHER INFORMATION: F1 Light Chain CDR1

<400> SEQUENCE: 15
cgggccagtg aaaacgttgg tgactggttg gcc                           33

<210> SEQ ID NO 16
<211> LENGTH: 21
<212> TYPE: DNA
<213> ORGANISM: Artificial Sequence
<220> FEATURE:
<223> OTHER INFORMATION: Synthetic construct
<220> FEATURE:
<223> OTHER INFORMATION: F1 Light Chain CDR2

<400> SEQUENCE: 16
aagacatcta ttctagaaag t                                       21

<210> SEQ ID NO 17
<211> LENGTH: 27
<212> TYPE: DNA
<213> ORGANISM: Artificial Sequence
<220> FEATURE:
<223> OTHER INFORMATION: Synthetic construct
<220> FEATURE:
<223> OTHER INFORMATION: F1 Light Chain CDR3

<400> SEQUENCE: 17
caacactata tacgtttccc gtacact                                 27

<210> SEQ ID NO 18
<211> LENGTH: 28
<212> TYPE: DNA
<213> ORGANISM: Artificial Sequence
<220> FEATURE:
<223> OTHER INFORMATION: Synthetic construct
<220> FEATURE:
<223> OTHER INFORMATION: Primer

<400> SEQUENCE: 18
atggctgagg tgcagctggt ggagtctg                                28

<210> SEQ ID NO 19
<211> LENGTH: 61
<212> TYPE: DNA
<213> ORGANISM: Artificial Sequence
<220> FEATURE:
<223> OTHER INFORMATION: Synthetic construct
<220> FEATURE:
<223> OTHER INFORMATION: Primer

<400> SEQUENCE: 19
gaacacgctg gggcccttgg tgctggcact cgagactgtg accagggtgc caggtccccca    60 g                                                                     61

<210> SEQ ID NO 20
<211> LENGTH: 30
<212> TYPE: DNA
<213> ORGANISM: Artificial Sequence
<220> FEATURE:
<223> OTHER INFORMATION: Synthetic construct
<220> FEATURE:
<223> OTHER INFORMATION: Primer

<400> SEQUENCE: 20
cggctcgacc gatatccagc tgacccagag                              30
```

```
<210> SEQ ID NO 21
<211> LENGTH: 25
<212> TYPE: DNA
<213> ORGANISM: Artificial Sequence
<220> FEATURE:
<223> OTHER INFORMATION: Synthetic construct
<220> FEATURE:
<223> OTHER INFORMATION: Primer

<400> SEQUENCE: 21
gatttccagc ttggtaccct ggccg                                               25

<210> SEQ ID NO 22
<211> LENGTH: 38
<212> TYPE: DNA
<213> ORGANISM: Artificial Sequence
<220> FEATURE:
<223> OTHER INFORMATION: Synthetic construct
<220> FEATURE:
<223> OTHER INFORMATION: Primer

<400> SEQUENCE: 22
ggtggccagc atcaacagcg gcaacaaccc ctactacg                                 38

<210> SEQ ID NO 23
<211> LENGTH: 38
<212> TYPE: DNA
<213> ORGANISM: Artificial Sequence
<220> FEATURE:
<223> OTHER INFORMATION: Synthetic construct
<220> FEATURE:
<223> OTHER INFORMATION: Primer

<400> SEQUENCE: 23
cgtagtaggg gttgttgccg ctgttgatgc tggccacc                                 38

<210> SEQ ID NO 24
<211> LENGTH: 5
<212> TYPE: PRT
<213> ORGANISM: Artificial Sequence
<220> FEATURE:
<223> OTHER INFORMATION: Synthetic construct
<220> FEATURE:
<223> OTHER INFORMATION: Part of CDR2 Heavy Chain to Show Amidation
<220> FEATURE:
<221> NAME/KEY: MOD_RES
<222> LOCATION: 2
<223> OTHER INFORMATION: Amidation

<400> SEQUENCE: 24

Asn Asn Gly Asn Asn
 1               5

<210> SEQ ID NO 25
<211> LENGTH: 3
<212> TYPE: DNA
<213> ORGANISM: Artificial Sequence
<220> FEATURE:
<223> OTHER INFORMATION: Synthetic construct
<220> FEATURE:
<223> OTHER INFORMATION: Codon for N

<400> SEQUENCE: 25 aac                                                                        3

<210> SEQ ID NO 26
<211> LENGTH: 3
<212> TYPE: DNA
<213> ORGANISM: Artificial Sequence
<220> FEATURE:
```

<223> OTHER INFORMATION: Synthetic construct
<220> FEATURE:
<223> OTHER INFORMATION: Codon for S

<400> SEQUENCE: 26 agc                                                                  3

<210> SEQ ID NO 27
<211> LENGTH: 36
<212> TYPE: DNA
<213> ORGANISM: Artificial Sequence
<220> FEATURE:
<223> OTHER INFORMATION: Synthetic construct
<220> FEATURE:
<223> OTHER INFORMATION: Oligo

<400> SEQUENCE: 27
gggcctgagc tcgccctgca caaagagctt caacag                             36

<210> SEQ ID NO 28
<211> LENGTH: 36
<212> TYPE: DNA
<213> ORGANISM: Artificial Sequence
<220> FEATURE:
<223> OTHER INFORMATION: Synthetic construct
<220> FEATURE:
<223> OTHER INFORMATION: Oligo

<400> SEQUENCE: 28
ctgttgaagc tctttgtgca gggcgagctc aggccc                             36

<210> SEQ ID NO 29
<211> LENGTH: 38
<212> TYPE: DNA
<213> ORGANISM: Artificial Sequence
<220> FEATURE:
<223> OTHER INFORMATION: Synthetic construct
<220> FEATURE:
<223> OTHER INFORMATION: Oligo

<400> SEQUENCE: 29
ctggtcacag tctcgagttg cagcaccaag ggcccatc                           38

<210> SEQ ID NO 30
<211> LENGTH: 38
<212> TYPE: DNA
<213> ORGANISM: Artificial Sequence
<220> FEATURE:
<223> OTHER INFORMATION: Synthetic construct
<220> FEATURE:
<223> OTHER INFORMATION: Oligo

<400> SEQUENCE: 30
gatgggccct tggtgctgca actcgagact gtgaccag                           38

<210> SEQ ID NO 31
<211> LENGTH: 5
<212> TYPE: PRT
<213> ORGANISM: Artificial Sequence
<220> FEATURE:
<223> OTHER INFORMATION: Synthetic construct
<220> FEATURE:
<223> OTHER INFORMATION: Motif
<220> FEATURE:
<221> NAME/KEY: VARIANT
<222> LOCATION: 3
<223> OTHER INFORMATION: Xaa = Any Amino Acid

<400> SEQUENCE: 31

```
<210> SEQ ID NO 32
<211> LENGTH: 4
<212> TYPE: PRT
<213> ORGANISM: Artificial Sequence
<220> FEATURE:
<223> OTHER INFORMATION: Synthetic construct
<220> FEATURE:
<223> OTHER INFORMATION: His-tagged SD insert

<400> SEQUENCE: 32

Ser Asp Ser Asp
 1

<210> SEQ ID NO 33
<211> LENGTH: 5
<212> TYPE: PRT
<213> ORGANISM: Artificial Sequence
<220> FEATURE:
<223> OTHER INFORMATION: Synthetic construct
<220> FEATURE:
<223> OTHER INFORMATION: His-tagged SD insert

<400> SEQUENCE: 33

Ser Asp Ser Asp Ser
 1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic construct
<220> FEATURE:
<223> OTHER INFORMATION: His-tagged SD insert

<400> SEQUENCE: 34

Ser Asp Ser Asp Ser Asp
 1               5

<210> SEQ ID NO 35
<211> LENGTH: 360
<212> TYPE: DNA
<213> ORGANISM: Artificial Sequence
<220> FEATURE:
<223> OTHER INFORMATION: Synthetic construct
<220> FEATURE:
<223> OTHER INFORMATION: F1 Heavy Chain
<220> FEATURE:
<221> NAME/KEY: CDS
<222> LOCATION: (1)..(360)

<400> SEQUENCE: 35
```

Preceding the SEQ ID NO 32 block:

```
Leu Pro Xaa Thr Gly
 1               5
```

| | | | | | | | | | | | | | | | | |
|---|---|---|---|---|---|---|---|---|---|---|---|---|---|---|---|---|
| gag | gtg | caa | ctg | ttg | gag | tcg | ggg | ggg | ggc | ttg | gtg | cag | ccg | ggg | ggg | 48 |
| Glu | Val | Gln | Leu | Leu | Glu | Ser | Gly | Gly | Gly | Leu | Val | Gln | Pro | Gly | Gly | |
| 1 | | | | 5 | | | | | 10 | | | | | 15 | | |
| tcc | ctg | aga | ctc | tcc | tgt | gca | gcc | tct | gga | ttc | acc | ctt | agc | cgc | ttt | 96 |
| Ser | Leu | Arg | Leu | Ser | Cys | Ala | Ala | Ser | Gly | Phe | Thr | Leu | Ser | Arg | Phe | |
| | | | 20 | | | | | 25 | | | | | 30 | | | |
| gcc | atg | agc | tgg | gtc | cgc | cag | gct | cca | gga | agg | gga | ctg | gaa | tgg | gtc | 144 |
| Ala | Met | Ser | Trp | Val | Arg | Gln | Ala | Pro | Gly | Arg | Gly | Leu | Glu | Trp | Val | |
| | | 35 | | | | | 40 | | | | | 45 | | | | |
| gca | tcg | atc | aat | aat | ggg | aat | aac | cca | tac | tac | gca | cgg | tcg | gta | caa | 192 |
| Ala | Ser | Ile | Asn | Asn | Gly | Asn | Asn | Pro | Tyr | Tyr | Ala | Arg | Ser | Val | Gln | |
| | 50 | | | | | 55 | | | | | 60 | | | | | |
| tac | cgc | ttc | acc | gtc | tcc | cgg | gac | gtc | tcc | cag | aac | act | gtg | tct | ctg | 240 |

```
Tyr Arg Phe Thr Val Ser Arg Asp Val Ser Gln Asn Thr Val Ser Leu
 65                  70                  75                  80 cag atg aac aac ctg aga gcc gaa gac tcg gcc aca tat ttc tgt gct     288
Gln Met Asn Asn Leu Arg Ala Glu Asp Ser Ala Thr Tyr Phe Cys Ala
                 85                  90                  95 aaa gat cac cct agt agt ggc tgg ccc acc ttt gac tcc tgg ggc ccg     336
Lys Asp His Pro Ser Ser Gly Trp Pro Thr Phe Asp Ser Trp Gly Pro
            100                 105                 110 gga acc ctg gtc acc gtc tcc tcg                                     360
Gly Thr Leu Val Thr Val Ser Ser
        115                 120

<210> SEQ ID NO 36
<211> LENGTH: 120
<212> TYPE: PRT
<213> ORGANISM: Artificial Sequence
<220> FEATURE:
<223> OTHER INFORMATION: Synthetic construct

<400> SEQUENCE: 36

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Leu Ser Arg Phe
             20                  25                  30

Ala Met Ser Trp Val Arg Gln Ala Pro Gly Arg Gly Leu Glu Trp Val
         35                  40                  45

Ala Ser Ile Asn Asn Gly Asn Asn Pro Tyr Tyr Ala Arg Ser Val Gln
     50                  55                  60

Tyr Arg Phe Thr Val Ser Arg Asp Val Ser Gln Asn Thr Val Ser Leu
 65                  70                  75                  80

Gln Met Asn Asn Leu Arg Ala Glu Asp Ser Ala Thr Tyr Phe Cys Ala
                 85                  90                  95

Lys Asp His Pro Ser Ser Gly Trp Pro Thr Phe Asp Ser Trp Gly Pro
            100                 105                 110

Gly Thr Leu Val Thr Val Ser Ser
        115                 120

<210> SEQ ID NO 37
<211> LENGTH: 90
<212> TYPE: DNA
<213> ORGANISM: Artificial Sequence
<220> FEATURE:
<223> OTHER INFORMATION: Synthetic construct
<220> FEATURE:
<223> OTHER INFORMATION: F1 Heavy Chain FW1
<220> FEATURE:
<221> NAME/KEY: CDS
<222> LOCATION: (1)..(90)

<400> SEQUENCE: 37 gag gtg caa ctg ttg gag tcg ggg ggg ggc ttg gtg cag ccg ggg ggg      48
Glu Val Gln Leu Leu Glu Ser Gly Gly Gly Leu Val Gln Pro Gly Gly
 1               5                  10                  15 tcc ctg aga ctc tcc tgt gca gcc tct gga ttc acc ctt agc              90
Ser Leu Arg Leu Ser Cys Ala Ala Ser Gly Phe Thr Leu Ser
             20                  25                  30

<210> SEQ ID NO 38
<211> LENGTH: 30
<212> TYPE: PRT
<213> ORGANISM: Artificial Sequence
<220> FEATURE:
<223> OTHER INFORMATION: Synthetic construct
```

<400> SEQUENCE: 38

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser
            20                  25                  30

<210> SEQ ID NO 39
<211> LENGTH: 42
<212> TYPE: DNA
<213> ORGANISM: Artificial Sequence
<220> FEATURE:
<223> OTHER INFORMATION: Synthetic construct
<220> FEATURE:
<223> OTHER INFORMATION: F1 Heavy Chain FW2
<220> FEATURE:
<221> NAME/KEY: CDS
<222> LOCATION: (1)..(42)

<400> SEQUENCE: 39 tgg gtc cgc cag gct cca gga agg gga ctg gaa tgg gtc gca          42
Trp Val Arg Gln Ala Pro Gly Arg Gly Leu Glu Trp Val Ala
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Synthetic construct

<400> SEQUENCE: 40

Trp Val Arg Gln Ala Pro Gly Arg Gly Leu Glu Trp Val Ala
1               5                   10

<210> SEQ ID NO 41
<211> LENGTH: 96
<212> TYPE: DNA
<213> ORGANISM: Artificial Sequence
<220> FEATURE:
<223> OTHER INFORMATION: Synthetic construct
<220> FEATURE:
<223> OTHER INFORMATION: F1 Heavy Chain FW3
<220> FEATURE:
<221> NAME/KEY: CDS
<222> LOCATION: (1)..(96)

<400> SEQUENCE: 41 cgc ttc acc gtc tcc cgg gac gtc tcc cag aac act gtg tct ctg cag    48
Arg Phe Thr Val Ser Arg Asp Val Ser Gln Asn Thr Val Ser Leu Gln
1               5                   10                  15 atg aac aac ctg aga gcc gaa gac tcg gcc aca tat ttc tgt gct aaa    96
Met Asn Asn Leu Arg Ala Glu Asp Ser Ala Thr Tyr Phe Cys Ala Lys
            20                  25                  30

<210> SEQ ID NO 42
<211> LENGTH: 32
<212> TYPE: PRT
<213> ORGANISM: Artificial Sequence
<220> FEATURE:
<223> OTHER INFORMATION: Synthetic construct

<400> SEQUENCE: 42

Arg Phe Thr Val Ser Arg Asp Val Ser Gln Asn Thr Val Ser Leu Gln
1               5                   10                  15

Met Asn Asn Leu Arg Ala Glu Asp Ser Ala Thr Tyr Phe Cys Ala Lys
            20                  25                  30

<210> SEQ ID NO 43
<211> LENGTH: 33
<212> TYPE: DNA
<213> ORGANISM: Artificial Sequence
<220> FEATURE:
<223> OTHER INFORMATION: Synthetic construct
<220> FEATURE:
<223> OTHER INFORMATION: F1 Heavy Chain FW4
<220> FEATURE:
<221> NAME/KEY: CDS
<222> LOCATION: (1)..(33)

<400> SEQUENCE: 43

```
tgg ggc ccg gga acc ctg gtc acc gtc tcc tcg                    33
Trp Gly Pro Gly Thr Leu Val Thr Val Ser Ser
1               5                   10
```

<210> SEQ ID NO 44
<211> LENGTH: 11
<212> TYPE: PRT
<213> ORGANISM: Artificial Sequence
<220> FEATURE:
<223> OTHER INFORMATION: Synthetic construct

<400> SEQUENCE: 44

```
Trp Gly Pro Gly Thr Leu Val Thr Val Ser Ser
1               5                   10
```

<210> SEQ ID NO 45
<211> LENGTH: 330
<212> TYPE: DNA
<213> ORGANISM: Artificial Sequence
<220> FEATURE:
<223> OTHER INFORMATION: Synthetic construct
<220> FEATURE:
<223> OTHER INFORMATION: F1 Light Chain
<220> FEATURE:
<221> NAME/KEY: CDS
<222> LOCATION: (1)..(330)

<400> SEQUENCE: 45

```
gac atc cag ttg acc cag tct cct tcc gcc ctg cct gca tct gtg gga    48
Asp Ile Gln Leu Thr Gln Ser Pro Ser Ala Leu Pro Ala Ser Val Gly
1               5                   10                  15 gac aga gtc agc atc act tgt cgg gcc agt gaa aac gtt ggt gac tgg    96
Asp Arg Val Ser Ile Thr Cys Arg Ala Ser Glu Asn Val Gly Asp Trp
            20                  25                  30 ttg gcc tgg tat cgg cag aaa ccg ggg aaa gcc cct aat ctt ctc atc    144
Leu Ala Trp Tyr Arg Gln Lys Pro Gly Lys Ala Pro Asn Leu Leu Ile
        35                  40                  45 tat aag aca tct att cta gaa agt ggg gtc cca tca agg ttc agc ggc    192
Tyr Lys Thr Ser Ile Leu Glu Ser Gly Val Pro Ser Arg Phe Ser Gly
    50                  55                  60 agt ggg tct ggg aca gaa ttc act ctc acc atc agc agc ctg cag cct    240
Ser Gly Ser Gly Thr Glu Phe Thr Leu Thr Ile Ser Ser Leu Gln Pro
65                  70                  75                  80 gat gat ttt gca act tat tac tgt caa cac tat ata cgt ttc ccg tac    288
Asp Asp Phe Ala Thr Tyr Tyr Cys Gln His Tyr Ile Arg Phe Pro Tyr
                85                  90                  95 act ttt ggc cag ggg acc aag ctg gag atc aaa cga act gtg            330
Thr Phe Gly Gln Gly Thr Lys Leu Glu Ile Lys Arg Thr Val
            100                 105                 110
```

<210> SEQ ID NO 46
<211> LENGTH: 110
<212> TYPE: PRT
<213> ORGANISM: Artificial Sequence
<220> FEATURE:

<223> OTHER INFORMATION: Synthetic construct

<400> SEQUENCE: 46

Asp Ile Gln Leu Thr Gln Ser Pro Ser Ala Leu Pro Ala Ser Val Gly
1               5                   10                  15

Asp Arg Val Ser Ile Thr Cys Arg Ala Ser Glu Asn Val Gly Asp Trp
            20                  25                  30

Leu Ala Trp Tyr Arg Gln Lys Pro Gly Lys Ala Pro Asn Leu Leu Ile
        35                  40                  45

Tyr Lys Thr Ser Ile Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Tyr Ile Arg Phe Pro Tyr
                85                  90                  95

Thr Phe Gly Gln Gly Thr Lys Leu Glu Ile Lys Arg Thr Val
            100                 105                 110

<210> SEQ ID NO 47
<211> LENGTH: 69
<212> TYPE: DNA
<213> ORGANISM: Artificial Sequence
<220> FEATURE:
<223> OTHER INFORMATION: Synthetic construct
<220> FEATURE:
<223> OTHER INFORMATION: F1 Light Chain FW1
<220> FEATURE:
<221> NAME/KEY: CDS
<222> LOCATION: (1)..(69)

<400> SEQUENCE: 47 gac atc cag ttg acc cag tct cct tcc gcc ctg cct gca tct gtg gga      48
Asp Ile Gln Leu Thr Gln Ser Pro Ser Ala Leu Pro Ala Ser Val Gly
1               5                   10                  15 gac aga gtc agc atc act tgt                                          69
Asp Arg Val Ser Ile Thr Cys
            20

<210> SEQ ID NO 48
<211> LENGTH: 23
<212> TYPE: PRT
<213> ORGANISM: Artificial Sequence
<220> FEATURE:
<223> OTHER INFORMATION: Synthetic construct

<400> SEQUENCE: 48

Asp Ile Gln Leu Thr Gln Ser Pro Ser Ala Leu Pro Ala Ser Val Gly
1               5                   10                  15

Asp Arg Val Ser Ile Thr Cys
            20

<210> SEQ ID NO 49
<211> LENGTH: 45
<212> TYPE: DNA
<213> ORGANISM: Artificial Sequence
<220> FEATURE:
<223> OTHER INFORMATION: Synthetic construct
<220> FEATURE:
<223> OTHER INFORMATION: F1 Light Chain FW2
<220> FEATURE:
<221> NAME/KEY: CDS
<222> LOCATION: (1)..(45)

<400> SEQUENCE: 49 tgg tat cgg cag aaa ccg ggg aaa gcc cct aat ctt ctc atc tat          45

Trp Tyr Arg Gln Lys Pro Gly Lys Ala Pro Asn Leu Leu Ile Tyr
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Synthetic construct

<400> SEQUENCE: 50

Trp Tyr Arg Gln Lys Pro Gly Lys Ala Pro Asn Leu Leu Ile Tyr
1               5                   10                  15

<210> SEQ ID NO 51
<211> LENGTH: 96
<212> TYPE: DNA
<213> ORGANISM: Artificial Sequence
<220> FEATURE:
<223> OTHER INFORMATION: Synthetic construct
<220> FEATURE:
<223> OTHER INFORMATION: F1 Light Chain FW3
<220> FEATURE:
<221> NAME/KEY: CDS
<222> LOCATION: (1)..(96)

<400> SEQUENCE: 51 ggg gtc cca tca agg ttc agc ggc agt ggg tct ggg aca gaa ttc act      48
Gly Val Pro Ser Arg Phe Ser Gly Ser Gly Ser Gly Thr Glu Phe Thr
1               5                   10                  15 ctc acc atc agc agc ctg cag cct gat gat ttt gca act tat tac tgt      96
Leu Thr Ile Ser Ser Leu Gln Pro Asp Asp Phe Ala Thr Tyr Tyr Cys
            20                  25                  30

<210> SEQ ID NO 52
<211> LENGTH: 32
<212> TYPE: PRT
<213> ORGANISM: Artificial Sequence
<220> FEATURE:
<223> OTHER INFORMATION: Synthetic construct

<400> SEQUENCE: 52

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

<210> SEQ ID NO 53
<211> LENGTH: 39
<212> TYPE: DNA
<213> ORGANISM: Artificial Sequence
<220> FEATURE:
<223> OTHER INFORMATION: Synthetic construct
<220> FEATURE:
<223> OTHER INFORMATION: F1 Light Chain FW4
<220> FEATURE:
<221> NAME/KEY: CDS
<222> LOCATION: (1)..(39)

<400> SEQUENCE: 53 ttt ggc cag ggg acc aag ctg gag atc aaa cga act gtg                  39
Phe Gly Gln Gly Thr Lys Leu Glu Ile Lys Arg Thr Val
1               5                   10

<210> SEQ ID NO 54
<211> LENGTH: 13
<212> TYPE: PRT
<213> ORGANISM: Artificial Sequence
<220> FEATURE:

<223> OTHER INFORMATION: Synthetic construct

<400> SEQUENCE: 54

Phe Gly Gln Gly Thr Lys Leu Glu Ile Lys Arg Thr Val
1               5                   10

<210> SEQ ID NO 55
<211> LENGTH: 230
<212> TYPE: PRT
<213> ORGANISM: Artificial Sequence
<220> FEATURE:
<223> OTHER INFORMATION: Synthetic construct
<220> FEATURE:
<223> OTHER INFORMATION: rF1 Heavy Chain

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Arg Phe
            20                  25                  30

Ala Met Ser Trp Val Arg Gln Ala Pro Gly Arg Gly Leu Glu Trp Val
        35                  40                  45

Ala Ser Ile Asn Asn Gly Asn Asn Pro Tyr Tyr Ala Arg Ser Val Gln
    50                  55                  60

Tyr Arg Phe Thr Val Ser Arg Asp Val Ser Gln Asn Thr Val Ser Leu
65                  70                  75                  80

Gln Met Asn Asn Leu Arg Ala Glu Asp Ser Ala Thr Tyr Phe Cys Ala
                85                  90                  95

Lys Asp His Pro Ser Ser Gly Trp Pro Thr Phe Asp Ser Trp Gly Pro
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro
225                 230

<210> SEQ ID NO 56
<211> LENGTH: 230
<212> TYPE: PRT
<213> ORGANISM: Artificial Sequence
<220> FEATURE:
<223> OTHER INFORMATION: Synthetic construct
<220> FEATURE:
<223> OTHER INFORMATION: rF1 A114C

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Arg Phe

```
                    20                  25                  30
Ala Met Ser Trp Val Arg Gln Ala Pro Gly Arg Gly Leu Glu Trp Val
            35                  40                  45

Ala Ser Ile Asn Ser Gly Asn Asn Pro Tyr Tyr Ala Arg Ser Val Gln
        50                  55                  60

Tyr Arg Phe Thr Val Ser Arg Asp Val Ser Gln Asn Thr Val Ser Leu
65                  70                  75                  80

Gln Met Asn Asn Leu Arg Ala Glu Asp Ser Ala Thr Tyr Phe Cys Ala
                85                  90                  95

Lys Asp His Pro Ser Ser Gly Trp Pro Thr Phe Asp Ser Trp Gly Pro
            100                 105                 110

Gly Thr Leu Val Thr Val Ser Ser Cys Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro
225                 230

<210> SEQ ID NO 57
<211> LENGTH: 213
<212> TYPE: PRT
<213> ORGANISM: Artificial Sequence
<220> FEATURE:
<223> OTHER INFORMATION: Synthetic construct
<220> FEATURE:
<223> OTHER INFORMATION: rF1 Light Chain

<400> SEQUENCE: 57

Asp Ile Gln Leu Thr Gln Ser Pro Ser Ala Leu Pro Ala Ser Val Gly
1               5                   10                  15

Asp Arg Val Ser Ile Thr Cys Arg Ala Ser Glu Asn Val Gly Asp Trp
            20                  25                  30

Leu Ala Trp Tyr Arg Gln Lys Pro Gly Lys Ala Pro Asn Leu Leu Ile
        35                  40                  45

Tyr Lys Thr Ser Ile Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Tyr Met Arg Phe Pro Tyr
                85                  90                  95

Thr Phe Gly Gln Gly Thr Lys Leu Glu Ile Lys Arg Ala Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140
```

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
210

<210> SEQ ID NO 58
<211> LENGTH: 214
<212> TYPE: PRT
<213> ORGANISM: Artificial Sequence
<220> FEATURE:
<223> OTHER INFORMATION: Synthetic construct
<220> FEATURE:
<223> OTHER INFORMATION: rF1 V205C

<400> SEQUENCE: 58

Asp Ile Gln Leu Thr Gln Ser Pro Ser Ala Leu Pro Ala Ser Val Gly
1               5                   10                  15

Asp Arg Val Ser Ile Thr Cys Arg Ala Ser Glu Asn Val Gly Asp Trp
            20                  25                  30

Leu Ala Trp Tyr Arg Gln Lys Pro Gly Lys Ala Pro Asn Leu Leu Ile
        35                  40                  45

Tyr Lys Thr Ser Ile Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Tyr Met Arg Phe Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Cys Thr Lys Ser
        195                 200                 205

Phe Asn Arg Gly Glu Cys
    210

<210> SEQ ID NO 59
<211> LENGTH: 13
<212> TYPE: PRT
<213> ORGANISM: Artificial Sequence
<220> FEATURE:
<223> OTHER INFORMATION: Synthetic construct

<400> SEQUENCE: 59

Phe Gly Gln Gly Thr Lys Val Glu Ile Lys Arg Thr Val

<210> SEQ ID NO 60
<211> LENGTH: 16
<212> TYPE: PRT
<213> ORGANISM: Artificial Sequence
<220> FEATURE:
<223> OTHER INFORMATION: Synthetic construct
<220> FEATURE:
<223> OTHER INFORMATION: rF1 A114C

<400> SEQUENCE: 60

Ser Ile Asn Ser Gly Asn Asn Pro Tyr Tyr Ala Arg Ser Val Gln Tyr
1               5                   10                  15

<210> SEQ ID NO 61
<211> LENGTH: 30
<212> TYPE: PRT
<213> ORGANISM: Artificial Sequence
<220> FEATURE:
<223> OTHER INFORMATION: Synthetic construct
<220> FEATURE:
<223> OTHER INFORMATION: rF1 Heavy Chain

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser
            20                  25                  30

<210> SEQ ID NO 62
<211> LENGTH: 120
<212> TYPE: PRT
<213> ORGANISM: Artificial Sequence
<220> FEATURE:
<223> OTHER INFORMATION: Synthetic construct
<220> FEATURE:
<223> OTHER INFORMATION: rF1 A114C

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Arg Phe
            20                  25                  30

Ala Met Ser Trp Val Arg Gln Ala Pro Gly Arg Gly Leu Glu Trp Val
        35                  40                  45

Ala Ser Ile Asn Ser Gly Asn Asn Pro Tyr Tyr Ala Arg Ser Val Gln
    50                  55                  60

Tyr Arg Phe Thr Val Ser Arg Asp Val

```
<400> SEQUENCE: 63

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro
            100                 105                 110

<210> SEQ ID NO 64
<211> LENGTH: 104
<212> TYPE: PRT
<213> ORGANISM: Artificial Sequence
<220> FEATURE:
<223> OTHER INFORMATION: Synthetic construct
<220> FEATURE:
<223> OTHER INFORMATION: rF1 Light Chain

<400> SEQUENCE: 64

Ala Ala Pro Ser Val Phe Ile Phe Pro Pro Ser Asp Glu Gln Leu Lys
 1               5                  10                  15

Ser Gly Thr Ala Ser Val Val Cys Leu Leu Asn Asn Phe Tyr Pro Arg
            20                  25                  30

Glu Ala Lys Val Gln Trp Lys Val Asp Asn Ala Leu Gln Ser Gly Asn
        35                  40                  45

Ser Gln Glu Ser Val Thr Glu Gln Asp Ser Lys Asp Ser Thr Tyr Ser
    50                  55                  60

Leu Ser Ser Thr Leu Thr Leu Ser Lys Ala Asp Tyr Glu Lys His Lys
65                  70                  75                  80

Val Tyr Ala Cys Glu Val Thr His Gln Gly Leu Ser Ser Pro Val Thr
                85                  90                  95

Lys Ser Phe Asn Arg Gly Glu Cys
            100
```